(12) United States Patent
Freskos et al.

(10) Patent No.: US 6,716,844 B2
(45) Date of Patent: *Apr. 6, 2004

(54) AROMATIC SULFONYL ALPHA-HYDROXY HYDROXAMIC ACID COMPOUNDS

(75) Inventors: John N. Freskos, Clayton, MO (US); Terri L. Boehm, Ballwin, MO (US); Brent V. Mischke, Defiance, MO (US); Robert M. Heintz, Ballwin, MO (US); Joseph J. McDonald, Ballwin, MO (US); Gary A. DeCrescenzo, St. Charles, MO (US); Susan C. Howard, Fenton, MO (US)

(73) Assignee: Pharmacia Corporation, St. Louis, MO (US)

( * ) Notice: Subject to any disclaimer, the term of this patent is extended or adjusted under 35 U.S.C. 154(b) by 203 days.

This patent is subject to a terminal disclaimer.

(21) Appl. No.: 10/005,437

(22) Filed: Dec. 3, 2001

(65) Prior Publication Data

US 2002/0173508 A1 Nov. 21, 2002

Related U.S. Application Data

(63) Continuation of application No. 09/254,535, filed as application No. PCT/US98/04277 on Mar. 4, 1998, now Pat. No. 6,362,183.
(60) Provisional application No. 60/035,182, filed on Mar. 4, 1997.

(51) Int. Cl.$^7$ ................ C07D 403/02; C07D 403/12; C07D 413/02; C07D 279/12; C07D 333/06
(52) U.S. Cl. ............... 514/238.2; 514/355; 514/575; 544/159; 546/316; 562/621
(58) Field of Search ............... 544/159; 546/316; 562/621; 514/238.2, 355, 575

(56) References Cited

U.S. PATENT DOCUMENTS

| 4,062,973 A | 12/1977 | Nickl et al. | 424/308 |
|---|---|---|---|
| 4,595,700 A | 6/1986 | Donald et al. | 514/616 |
| 5,527,945 A | 6/1996 | Janssen et al. | 558/411 |
| 5,536,837 A | 7/1996 | Urushibata et al. | 544/316 |
| 5,712,300 A | 1/1998 | Jacobsen | 514/389 |
| 6,362,183 B1 | 3/2002 | Freskos et al. | 514/238.2 |

FOREIGN PATENT DOCUMENTS

| EP | 0 780 386 | 6/1997 |
|---|---|---|
| WO | WO 90/05719 | 5/1990 |
| WO | WO 93/20047 | 10/1993 |
| WO | WO 94/02466 | 2/1994 |
| WO | WO 94/24140 | 10/1994 |
| WO | WO 95/09841 | 4/1995 |
| WO | WO 95/13289 | 5/1995 |
| WO | WO 95/29892 | 11/1995 |
| WO | WO 96/06074 | 2/1996 |
| WO | WO 96/11209 | 4/1996 |
| WO | WO 97/20824 | 6/1997 |
| WO | WO 97/24117 | 7/1997 |
| WO | WO 97/49679 | 12/1997 |
| WO | WO 98/13340 | 4/1998 |
| WO | WO 98/34915 | 8/1998 |

OTHER PUBLICATIONS

Dennis et al., "Matrix metalloproteinase inhibitors: Present achievements and future prospects", Investigational New Drugs 15: pp. 175–185, 1997.
Gearing et al., "Processing of tumour necrosis factor–α precursor by metalloproteinases", Nature, vol. 370, Aug. 1994, pp. 555–557.
Knight et al., FEBS Lett., vol. 296, No. 3, pp. 263–266 (1992).
Kenyon et al., "A Model of Angiogenesis in the Mouse Cornea", Investigative Ophthalmology & Visual Science, vol. 37, No. 8 (Jul. 1996).
McGeehan et al., "Regulation of tumour necrosis factor–∂ precursor by metalloproteinases inhibitor", Nature, vol. 370, Aug. 1994, pp. 558–561.
Mitchell et al., "Cloning, Expression, and Type II Collagenolytic Activity of Matrix Metalloproteinase–13 from Human Osteoarthritic Cartilage", J. Clin. Invest., vol. 97, No. 3, Feb. 1996, pp. 761–768.
Rasmussen et al., "Matrix Metalloproteinase Inhibition as a Novel Anticancer Strategy: A Review with Special Focus on Batimastar and Marimastar", Pharmacol. Th., vol. 75, No. 1, pp. 69–75, 1997.
Reboul et al., "The new Collagenese, Collagenese–3, is Expressed and Synthesized by Human Chondrocytes but not by Synoviocytes", J. Clin. Invest., vol. 97, No. 9, May 1996, pp. 2011–2019.
Schwartz et al., "Synthetic Inhibitors of Bacterial and Mammalinan Interstitial Collagenases", Progress in Medicinal Chemistry, vol. 29, pp. 271–334 (1992).

*Primary Examiner*—Deepak Rao
(74) *Attorney, Agent, or Firm*—Philip B. Polster, II; Julie M. Chappel

(57) ABSTRACT

An aromatic sulfonyl aipha-hydroxy hydroxamic acid compound that inter alia inhibits matrix metalloprotease activity is disclosed, as is a treatment process that comprises administering a contemplated aromatic sulfonyl alpha-hydroxy hydroxamic acid compound in an MMP enzyme-inhibiting effective amount to a host having a condition associated with pathological matrix metalloprotease activity.

19 Claims, No Drawings

AROMATIC SULFONYL ALPHA-HYDROXY HYDROXAMIC ACID COMPOUNDS

PRIORITY CLAIM TO RELATED PATENT APPLICATIONS

This patent claims priority as a continuation of U.S. patent application Ser. No. 09/254,535 (filed Jun. 4, 1999), now which U.S. Pat. No. 6,362,183 which is a 371 of International Patent Application No. PCT/US98/04277 (filed on Mar. 4, 1998; and published as International Publication No. WO 98/39326), which, in turn, claims priority to U.S. Provisional Patent Application Ser. No. 60/035,182 (filed Mar. 4, 1997). Each of the above-referenced applications are incorporated by reference into this patent.

DESCRIPTION

1. Technical Field

This invention is directed to proteinase (protease) inhibitors, and more particularly to aromatic sulfonyl alpha-hydroxy hydroxamic acid compounds that are useful, inter alia, as inhibitors for matrix metalloproteinases, compositions of those compounds, intermediates for the syntheses of the compounds, processes for the preparation of the compounds and processes for treating pathological conditions associated with pathological matrix metalloproteinase activity.

2. Background of the Invention

Connective tissue, extracellular matrix constituents and basement membranes are required components of all mammals. These components are the biological materials that provide rigidity, differentiation, attachments and, in some cases, elasticity to biological systems including human beings and other mammals. Connective tissues components include, for example, collagen, elastin, proteoglycans, fibronectin and laminin. These biochemicals make up, or are components of structures, such as skin, bone, teeth, tendon, cartilage, basement membrane, blood vessels, cornea and vitreous humor.

Under normal conditions, connective tissue turnover and/or repair processes are controlled and in equilibrium. The loss of this balance for whatever reason is involved in a number of disease states. Inhibition of the enzymes responsible for a loss of equilibrium provides a control mechanism for this tissue decomposition and, therefore, a treatment for these diseases.

Degradation of connective tissue or connective tissue components is carried out by the action of proteinase enzymes released from resident tissue cells and/or invading inflammatory or tumor cells. A major class of enzymes involved in this function are the zinc metalloproteinases (metalloproteases, or MMPs).

The metalloprotease enzymes are divided into classes with some members having several different names in common use. Examples are: collagenase I (MMP-1, fibroblast collagenase; EC 3.4.24.3); collagenase II (MMP-8, neutrophil collagenase; EC 3.4.24.34), collagenase III (MMP-13), stromelysin 1 (MMP-3; EC 3.4.24.17), stromelysin 2 (MMP-10; EC 3.4.24.22), proteoglycanase, matrilysin (MMP-7), gelatinase A (MMP-2, 72 kDa gelatinase, basement membrane collagenase; EC 3.4.24.24), gelatinase B (MMP-9, 92 kDa gelatinase; EC 3.4.24.35), stroinelysin 3 (MMP-11), metalloelastase (MMP-12, HME, human macrophage elastase) and membrane MMP (MMP-14). MMP is an abbreviation or acronym representing the term Matrix Metalloprotease with the attached numerals providing differentiation between specific members of the MMP group.

The uncontrolled breakdown of connective tissue by metalloproteases is a feature of many pathological conditions. Examples include rheumatoid arthritis, osteoarthritis, septic arthritis; corneal, epidermal or gastric ulceration; tumor metastasis, invasion or angiogenesis; periodontal disease; proteinuria; multiple sclerosis; Alzheimer's Disease; coronary thrombosis and bone disease. Defective injury repair processes can also occur. This can produce improper wound healing leading to weak repairs, adhesions and scarring. These latter defects can lead to disfigurement and/or permanent disabilities as with post-surgical adhesions.

Matrix metalloproteases are also involved in the biosynthesis of tumor necrosis factor (TNF) and inhibition of the production or action of TNF and related compounds is an important clinical disease treatment mechanism. TNF-$\alpha$, for example, is a cytokine that at present is thought to be produced initially as a 28 kD cell-associated molecule. It is released as an active, 17 kD form that can mediate a large number of deleterious effects in vitro and in vivo. For example, TNF can cause and/or contribute to the effects of inflammation, rheumatoid arthritis, autoimmune disease, multiple sclerosis, graft rejection, fibrotic disease, cancer, infectious diseases, malaria, mycobacterial infection, meningitis, fever, psoriasis, cardiovascular/pulmonary effects such as post-ischemic reperfusion injury, congestive heart failure, hemorrhage, coagulation, hyperoxic alveolar injury, radiation damage and acute phase responses like those seen with infections and sepsis and during shock such as septic shock and hemodynamic shock. Chronic release of active TNF can cause cachexia and anorexia. TNF can be lethal.

TNF-$\alpha$ convertase is a metalloproteinase involved in the formation of active TNF-$\alpha$. Inhibition of TNF-$\alpha$ convertase inhibits production of active TNF-$\alpha$. Compounds that inhibit both MMPs activity have been disclosed in WIPO International Publication Nos. WO 94/24140, WO 94/02466 and WO 97/20824. There remains a need for effective MMP and TNF-$\alpha$ convertase inhibiting agents. Compounds that inhibit MMPs such as collagenase, stromelysin and gelatinase have been shown to inhibit the release of TNF (Gearing et al. *Nature* 376, 555–557 (1994), McGeehan et al., *Nature* 376, 558–561 (1994)).

MMPs are involved in other biochemical processes in mammals as well. Included is the control of ovulation, post-partum uterine involution, possibly implantation, cleavage of APP ($\beta$-Amyloid Precursor Protein) to the amyloid plaque and inactivation of $\alpha_1$-protease inhibitor ($\alpha_1$-PI). Inhibition of these metalloproteases permits the control of fertility and the treatment or prevention of Alzheimers Disease. In addition, increasing and maintaining the levels of an endogenous or administered serine protease inhibitor drug or biochemical such as $\alpha_1$-PI supports the treatment and prevention of diseases such as emphysema, pulmonary diseases, inflammatory diseases and diseases of aging such as loss of skin or organ stretch and resiliency.

Inhibition of selected MMPs can also be desirable in other instances. Treatment of cancer and/or inhibition of metastasis and/or inhibition of angiogenesis are examples of approaches to the treatment of diseases wherein the selective inhibition of stromelysin (MMP-3), gelatinase (MMP-2), gelatinase B (MMP-9) or collagenase III (MMP-13) are the relatively most important enzyme or enzymes to inhibit especially when compared with collagenase I (MMP-1). A drug that does not inhibit collagenase I can have a superior therapeutic profile. Osteoarthritis. another prevalent disease wherein it is believed that cartilage degradation in inflamed joints is at least partially caused by MMP-13 released from cells such as stimulated chrondrocytes, may be best treated by administration of drugs one of whose modes of action is inhibition of MMP-13. See, for example, Mitchell et al., *J. Clin. Invest.*, 97:761–768 (1996) and Reboul et al., *J. Clin. Invest.*, 97:2011–2019 (1996).

Inhibitors of metalloproteases are known. Examples include natural biochemicals such as tissue inhibitor of metalloproteinase (TIMP), $\alpha_2$-macroglobulin and their analogs or derivatives. These are high molecular weight protein molecules that form inactive complexes with metalloproteases. A number of smaller peptide-like compounds that inhibit metalloproteases have been described. Mercaptoamide peptidyl derivatives have shown ACE inhibition in vitro and in vivo. Angiotensin converting enzyme (ACE) aids in the production of angiotensin II, a potent pressor substance in mammals and inhibition of this enzyme leads to the lowering of blood pressure.

Thiol group-containing amide or peptidyl amide-based metalloprotease (MMP) inhibitors are known as is shown in, for example, WO95/12389, WO96/11209 and U.S. Pat. No. 4,595,700. Hydroxamate group-containing MMP inhibitors are disclosed in a number of published patent applications such as WO 95/29892, WO 97/24117, WO 97/49679 and EP 0 780 386 that disclose carbon back-boned compounds, and WO 90/05719, WO 93/20047, WO 95/09841 and WO 96/06074 that disclose hydroxamates that have a peptidyl back-bones or peptidomimetic back-bones, as does the article by Schwartz et al., *Progr. Med. Chem.*, 29:271–334 (1992) and those of Rasmussen et al., *Pharmacol. Ther.*, 75 (1): 69–75 (1997) and Denis et al., *Invest. New Drugs*, 15(3): 175–185 (1997).

One possible problem associated with known MMP inhibitors is that such compounds often exhibit the same or similar inhibitory effects against each of the MMP enzymes. For example, the peptidomimetic hydroxamate known as batimastat is reported to exhibit $IC_{50}$ values of about 1 to about 20 nanomolar (nM) against each of MMP-1, MMP-2, MMP-3, MMP-7, and MMP-9. Marimastat, another peptidomimetic hydroxamate was reported to be another broad-spectrum MMP inhibitor with an enzyme inhibitory spectrum very similar to batimastat, except that marimastat exhibited an $IC_{50}$ value against MMP-3 of 230 nM. Rasmussen et al., *Pharmacol. Ther.*, 75(1): 69–75 (1997).

Meta analysis of data from Phase I/II studies using marimastat in patients with advanced, rapidly progressive, treatment-refractory solid tumor cancers (colorectal, pancreatic, ovarian, prostate) indicated a dose-related reduction in the rise of cancer-specific antigens used as surrogate markers for biological activity. Although marimastat exhibited some measure of efficacy via these markers, toxic side effects were noted. The most common drug-related toxicity of marimastat in those clinical trials was musculoskeletal pain and stiffness, often commencing in the small joints in the hands, spreading to the arms and shoulder. A short dosing holiday of 1–3 weeks followed by dosage reduction permits treatment to continue. Rasmussen et al., *Pharmacol. Ther.*, 75(1): 69–75 (1997). It is thought that the lack of specificity of inhibitory effect among the MMPs may be the cause of that effect.

In view of the importance of hydroxamate MMP inhibitor compounds in the treatment of several diseases and the lack of enzyme specificity exhibited by two of the more potent drugs now in clinical trials, it would be a great benefit if hydroxamates of greater enzyme specificity could be found. This would be particularly the case if the hydroxamate inhibitors exhibited strong inhibitory activity against one or more of MMP-2, MMP-9 or MMP-13 that are associated with several pathological conditions, while at the same time exhibiting limited inhibition of MMP-1, an enzyme that is relatively ubiquitous and known to participate in a number of homeostatic processes. The disclosure that follows describes one family of hydroxamate MMP inhibitors that exhibit those desirable activities.

BRIEF SUMMARY OF THE INVENTION

The present invention is directed to a family of molecules that inter alia inhibit matrix metalloprotease (MMP) activity, and particularly inhibit the activity of one or more of MMP-2, MMP-9, or MMP-13, while generally exhibiting little activity against MMP-1, as well as a process for treating a mammal having a condition associated with pathological activity.

Briefly, one embodiment of the present invention is directed to an aromatic sulfonyl alpha-hydroxy hydroxamic acid compound. That compound corresponds in structure to Formula I.

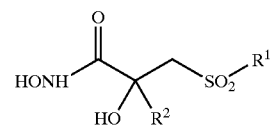

I wherein $R^2$ is a hydrido, $C_1$–$C_4$ hydrocarbyl, hydroxy-$C_1$–$C_4$ hydrocarbyl, $C_1$–$C_4$ hydrocarbyloxy, halo-$C_1$–$C_4$ hydrocarbyl, $C_1$–$C_4$ hydrocarbyloxymethyl, aminomethyl, (N—$C_1$–$C_3$ hydrocarbyl)aminomethyl, (N,N-di-$C_1$–$C_3$ hydrocarbyl)aminomethyl, (N-morpholino)methyl, (N-pyrrolidino)methyl, or (N-thiomorpholino)methyl group. $R^2$ is preferably a hydrido, hydroxy, hydroxymethyl, methoxymethyl or methyl-N-morpholinyl group.

$R^1$ is a substituent that contains a 5- or 6-membered cyclohydrocarbyl, heterocyclo, aryl or heteroaryl radical bonded directly to the depicted $SO_2$-group and having a length greater than about that of a fully extended hexyl group and less than about that of a fully extended eicosyl group. In addition, $R^1$ defines a three-dimensional volume, when rotated about an axis drawn through the $SO_2$-bonded 1-position and the 4-position of a 6-membered ring radical or drawn through the $SO_2$-bonded 1-position and the center of 3,4-bond of a 5-membered ring radical, whose widest dimension in a direction transverse to the axis of rotation is about that of one furanyl ring to about that of two phenyl rings.

$R^1$ preferably contains a single aromatic or heteroaromatic ring that is itself substituted with another substituent, $R^3$. $R^1$ most preferably contains a phenyl ring, Ph, that is itself has a substituent, $R^3$, at the 4-position. $R^3$ is preferably a phenyl, a phenoxy, a phenylazo, a thiophenoxy, an anilino, a benzamido, a nicotinamido, an isonicotinamido, a picolinamido or an ureidophenyl group that can itself be substituted at the meta- or para-position or both by a single atom or a substituent containing a longest chain of up to eight atoms, excluding hydrogen.

A process for treating a host mammal having a condition associated with pathological matrix metalloprotease activity is also contemplated. That process comprises administering a compound described hereinbefore in an enzyme-inhibiting effective amount to a mammalian host having such a condition. The use of repeated administrations is particularly contemplated.

Among the several benefits and advantages of the present invention are the provision of compounds and compositions effective as inhibitors of matrix metalloproteinase activity, and the provision of such compounds and compositions that are effective for the inhibition of metalloproteinases implicated in diseases and disorders involving uncontrolled breakdown of connective tissue.

More particularly, a benefit of this invention is the provision of a compound and composition effective for inhibiting metalloproteinases, particularly MMP-13 and/or MMP-2, associated with pathological conditions such as, for example, rheumatoid arthritis, osteoarthritis, septic arthritis; corneal, epidermal or gastric ulceration; tumor metastasis, invasion or angiogenesis; periodontal disease; proteinuria; multiple sclerosis; Alzheimer's Disease; coronary thrombosis and bone disease.

An advantage of the invention is the provision of a method for preparing such compositions. Another benefit is the provision of a method for treating a pathological condition associated with abnormal matrix metalloproteinase activity.

Another advantage of the invention is the provision of compounds, compositions and methods effective for treating such pathological conditions by selective inhibition of a metalloproteinase such as MMP-13 and MMP-2 associated with such conditions with minimal side effects resulting from inhibition of other proteinases such as MMP-1, whose activity is necessary or desirable for normal body function.

Still further benefits and advantages of the invention will be apparent to the skilled worker from the disclosure that follows.

DETAILED DESCRIPTION OF PREFERRED EMBODIMENTS

In accordance with the present invention, it has been found that certain aromatic sulfonyl alpha-hydroxy hydroxamic acids (hydroxamates) are effective for inhibition of matrix metalloproteinases ("MMPs") believed to be associated with uncontrolled or otherwise pathological breakdown of connective tissue. In particular, it has been found that these certain aromatic sulfonyl alpha-hydroxy hydroxamic acids are effective for inhibition of collagenase III (MMP-13) and also gelatinase A (MMP-2), which can be particularly destructive to tissue if present or generated in abnormal quantities or concentrations, and thus exhibit a pathological activity.

Moreover, it has been discovered that many of these aromatic sulfonyl alpha-hydroxy hydroxamic acids are selective in the inhibition of MMP-13, as well as other MMPs associated with diseased conditions without excessive inhibition of other collagenases essential to normal bodily function such as tissue turnover and repair. More particularly, at has been found that particularly preferred the aromatic sulfonyl alpha-hydroxy hydroxamic acids are particularly active in inhibiting of MMP-13 and MMP-2, while having a limited or minimal effect on MMP-1. This point is discussed in detail hereinafter and is illustrated in the Inhibition Tables hereinafter.

A contemplated compound corresponds to Formula I, below:

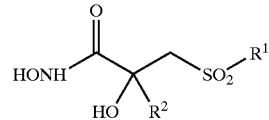

wherein $R^2$ is a hydrido, $C_1$–$C_4$ hydrocarbyl, hydroxy-$C_1$–$C_4$ hydrocarbyl, $C_1$–$C_4$ hydrocarbyloxy, halo-$C_1$–$C_4$ hydrocarbyl, $C_1$–$C_4$ hydrocarbyloxymethyl, aminomethyl ($NH_2CH_2$—), (N-$C_1$–$C_3$ hydrocarbyl) aminomethyl, (N,N-di-$C_1$–$C_3$ hydrocarbyl) aminomethyl [(N-$C_1$–$C_3$ hydrocarbyl) (N-$C_1$–$C_3$ hydrocarbyl) aminomethyl], (N-morpholino)methyl ($OC_4H_8NCH_2$—), (N-pyrrolidino)methyl ($C_4H_8NCH_2$—), or (N-thiomorpholino)methyl ($SC_4H_8NCH_2$—) group. In particularly preferred practice, $R^2$ substituent is a methyl, hydroxymethyl, (N-morpholino)methyl or methoxymethyl group. $R^1$ is a substituent containing a 5- or 6-membered cyclohydrocarbyl, heterocyclo, aryl or heteroaryl radical bonded directly to the depicted $SO_2$-group and having a length equivalent to a length that is greater than about that of a fully extended hexyl group and less than about that of a fully extended eicosyl group. In addition, $R^1$ defines a three-dimensional volume, when rotated about an axis drawn through the $SO_2$-bonded 1-position and the 4-position of a 6-membered ring radical or drawn through the $SO_2$-bonded 1-position and the center of 3,4-bond of a 5-membered ring radical, whose widest dimension in a direction transverse to the axis of rotation is about that of one furanyl ring to about that of two phenyl rings.

As noted above, an $R^1$ substituent contains a 5- or 6-membered cyclohydrocarbyl, heterocyclo, aryl or heteroaryl radical bonded directly to the depicted $SO_2$-group. An $R^1$ substituent also has length, width and substitution requirements that are discussed in detail below. It is noted here, however, that a single-ringed or fused ring cyclohydrocarbyl, heterocyclo, aryl or heteroaryl radical is not itself long enough to fulfill the length requirement. As such, that cyclohydrocarbyl, heterocyclo, aryl or heteroaryl radical must itself be substituted.

Exemplary 5- or 6-membered cyclohydrocarbyl, heterocyclo, aryl or heteroaryl radicals that can constitute a portion of a $R^1$ substituent and are themselves substituted as discussed herein include phenyl, 2-, 3-, or 4-pyridyl, 2-naththyl, 2-pyrazinyl, 2- or 5-pyrimidinyl, 2- or 3-benzo (b)thienyl, 8-purinyl, 2- or 3-furyl, 2- or 3-pyrrolyl, 2-imidazolyl, cyclopentyl, cyclohexyl, 2- or 3-piperidinyl, 2- or 3-morpholinyl, 2- or 3-tetrahydropyranyl, 2-imidazolidinyl, 2- or 3-pyrazolidinyl and the like. A phenyl radical is particularly preferred and is used illustratively herein.

When examined along its longest chain of atoms, an $R^1$ substituent, including its own substituent when present, has a total length that is greater than that of a fully extended saturated chain of six carbon atoms (a hexyl group); i.e., a length of a heptyl chain or longer, and a length that is less than that of a fully extended saturated chain of about 20 carbons (an eicosyl group). Preferably, that length is equivalent to that of a fully extended saturated chain of about 8 to about 18 carbon atoms, even though many more atoms may be present in the actual ring structures or substituents. This length requirement is discussed further below.

Looked at more generally, and aside from specific moieties from which it is constructed, an $R^1$ substituent (radical, group or moiety) has a length that is equivalent to that of a fully extended heptyl group or greater. Such an $R^1$ substituent also has a length that is less than that of a fully extended eicosyl group. That is to say that a $R^1$ is a substituent having a length greater than that of an extended saturated six carbon chain and shorter than that of an extended saturated eighteen carbon chain, and more preferably, a length greater than that of an octyl group and less than that of a palmityl group. The radical chain lengths are measured along the longest linear atom chain in the radical, following the skeletal atoms of a ring where necessary. Each atom in the chain, e.g. carbon, oxygen or nitrogen, is presumed to be carbon for ease in calculation.

Such lengths can be readily determined by using published bond angles, bond lengths and atomic radii, as needed, to draw and measure a chain, or by building models using commercially available kits whose bond angles, lengths and atomic radii are in accord with accepted, published values. Radical (substituent) lengths can also be determined somewhat less exactly by presuming, as is done here, that all atoms have bond lengths of saturated carbon, that unsaturated and aromatic bonds have the same lengths as saturated bonds and that bond angles for unsaturated bonds are the same as those for saturated bonds, although the above-mentioned modes of measurement are preferred. For example, a 4-phenyl or 4-pyridyl group has a length of a four carbon chain, as does a propoxy group, whereas a biphenyl group has a length of about an eight carbon chain using a contemplated measurement mode.

In addition, an $R^1$ substituent, when rotated about an axis drawn through the $SO_2$-bonded 1-position and the 4-position of a 6-membered ring radical or the $SO_2$-bonded 1-position and through the 3,4 bond of a 5-membered ring radical defines a three-dimensional volume whose widest dimension has the width of about one furanyl ring to about the width of two phenyl rings in a direction transverse to that axis to rotation.

When utilizing this width or volume criterion, a fused ring system such as a naphthyl or purinyl radical is considered to be a 6- or 5-membered ring that is substituted at appropriate positions numbered from the $SO_2$-linkage that is deemed to be at the 1-position as discussed before. Thus, a 2-naphthyl substituent or an 8-purinyl substituent is an appropriately sized $R^1$ radical as to width when examined using the above rotational width criterion. On the other hand, a 1-naphthyl group or a 7- or 9-purinyl group is too large upon rotation and is excluded.

As a consequence of these length and width requirements, $R^1$ substituents such as 4-(phenyl)phenyl [biphenyl], 4-(4'-methoxyphenyl)phenyl, 4-(phenoxy)phenyl, 4-(thiophenyl)phenyl [4-(phenylthio)phenyl], 4-(phenylazo)phenyl 4-(ureidophenyl)phenyl, 4-(anilino)phenyl, 4-(nicotinamido)phenyl, 4-(isonicotinamido)phenyl, 4-(picolinamido)phenyl and 4-(benzamido)phenyl are among particularly preferred $R^1$ substituents, with 4-(phenoxy)phenyl and 4-(thiophenyl)phenyl being most preferred.

An $SO_2$-linked cyclohydrocarbyl, heterocyclo, aryl or heteroaryl radical is a 5- or 6-membered single-ring that is itself substituted with one other substituent, $R^3$. The $SO_2$-linked single-ringed cyclohydrocarbyl, heterocyclo, aryl or heteroaryl radical is $R^3$-substituted at its own 4-position when a 6-membered ring and at its own 3-position when a 5-membered ring. The cyclohydrocarbyl, heterocyclo, aryl or heteroaryl radical to which $R^3$ is bonded is preferably a phenyl group, so that $R^1$ is preferably $PhR^3$ in which $R^3$ is bonded at the 4-position of the $SO_2$-linked phenyl (Ph) radical, and in which $R^3$ can itself be optionally substituted as is discussed hereinafter. Substitution at the 2-position of a $SO_2$-linked cyclohydrocarbyl, heterocyclo, aryl or heteroaryl radical appears to greatly lessen inhibitory potency toward MMP enzymes, and is absent from a contemplated compound.

A contemplated $R^3$ substituent can be a single-ringed cyclohydrocarbyl, heterocyclo, aryl or heteroaryl group or another substituent having a chain length of 3 to about 14 carbon atoms such as a hydrocarbyl or hydrocarbyloxy group [e.g., $C_3$–$C_{14}$ hydrocarbyl or O—$C_2$–$C_{14}$ hydrocarbyl], a phenyl group, a phenoxy group [—$OC_6H_5$], a thiophenoxy group [phenylsulfanyl; —$SC_6H_5$], an anilino group [—$NHC_6H_5$], a phenylazo group [—$N_2C_6H_5$], an ureidophenyl group (aniline carbonylamino; —NHC(O)NH—$C_6H_5$], a benzamido group [—NHC(O)$C_6H_5$], a nicotinamido group [3NHC(O)$C_5H_4N$], an isonicotinamido group [4NHC(O)$C_5H_4N$], or a picolinamido group [2NHC(O)$C_5H_4N$]. As noted before in conjunction with the discussion of $R^1$, most preferred $R^3$ substituents are phenoxy and thiophenoxy groups that are preferably themselves free of substitution. Additionally contemplated $R^3$ substituent groups include a heterocyclo, heterocyclohydrocarbyl, arylhydrocarbyl, arylheterocyclohydrocarbyl, heteroarylhydrocarbyl, heteroarylheterocyclohydrocarbyl, arylhydrocarbyloxyhydrocarbyl, aryloxyhydrocarbyl, hydrocarboylhydrocarbyl, arylhydrocarboylhydrocarbyl, arylcarbonylhydrocarbyl, arylazoaryl, arylhydrazinoaryl, hydrocarbylthiohydrocarbyl, hydrocarbylthioaryl, arylthiohydrocarbyl, heteroarylthiohydrocarbyl, hydrocarbylthioarylhydrocarbyl, arylhydrocarbylthiohydrocarbyl, arylhydrocarbylthioaryl, arylhydrocarbylamino, heteroarylhydrocarbylamino, or a heteroarylthio group.

A contemplated $R^3$ substituent can itself also be substituted with one or more substituent radicals at the meta- or para-position or both of a six-membered ring with a single atom or a substituent containing a longest chain of up to ten atoms, excluding hydrogen. Exemplary substituent radicals include a halo, hydrocarbyl, hydrocarbyloxy, nitro, cyano, perfluorohydrocarbyl, trifluoromethylhydrocarbyl, hydroxy, mercapto, hydroxycarbonyl, aryloxy, arylthio, arylamino, arylhydrocarbyl, aryl, heteroaryloxy, heteroarylthio, heteroarylamino, heteroarylhydrocarbyl, hydrocarbyloxycarbonylhydrocarbyl, heterocyclooxy, hydroxycarbonylhydrocarbyl, heterocyclothio, heterocycloamino, cyclohydrocarbyloxy, cyclohydrocarbylthio, cyclohydrocarbylamino, heteroarylhydrocarbyloxy, heteroarylhydrocarbylthio, heteroarylhydrocarbylamino, arylhydrocarbyloxy, arylhydrocarbylthio, arylhydrocarbylamino, heterocyclic, heteroaryl, hydroxycarbonyl-hydrocarbyloxy, alkoxycarbonylalkoxy, hydrocarbyloyl, arylcarbonyl, arylhydrocarbyloyl, hydrocarboyloxy, arylhydrocarboyloxy, hydroxyhydrocarbyl, hydroxyhydrocarbyloxy, hydrocarbylthio, hydrocarbyloxyhydrocarbylthio, hydrocarbyloxycarbonyl, hydroxycarbonylhydrocarbyloxy, hydrocarbyloxycarbonylhydrocarbyl, hydrocarbylhydroxycarbonylhydrocarbylthio, hydrocarbyloxycarbonylhydrocarbyloxy, hydrocarbyloxycarbonylhydrocarbylthio, amino, hydrocarbylcarbonylamino, arylcarbonylamino, cyclohydrocarbylcarbonylamino, heterocyclohydrocarbylcarbonylamino, arylhydrocarbylcarbonylamino, heteroarylcarbonylamino, heteroarylhydrocarbyl-carbonylamino, heterocyclohydrocarbyloxy, hydrocarbylsulfonylamino, arylsulfonylamino, arylhydrocarbylsulfonylamino, heteroarylsulfonylamino, heteroarylhydrocarbyl-sulfonylamino, cyclohydrocarbyl-sulfonylamino, heterocyclohydrocarbylsulfonylamino and N-monosubstituted or N,N-disubstituted aminohydrocarbyl group wherein the substituent(s) on the nitrogen are selected from the group consisting of hydrocarbyl, aryl, arylhydrocarbyl, cyclohydrocarbyl, arylhydrocarbyloxy-carbonyl, hydrocarbyloxycarbonyl, and hydrocarboyl, or wherein the nitrogen and two substituents attached thereto form a 5- to 8-membered heterocyclic or heteroaryl ring group.

Thus, initial studies indicate that so long as the length, substitution and width (volume upon rotation) requirements of an $SO_2$-linked $R^1$ substituent discussed herein are met, an $R^1$ substituent can be extremely varied.

A particularly preferred $R^3$ substituent of an $SO_2$-linked Ph group is a single-ringed aryl or heteroaryl, phenoxy, thiophenoxy, phenylazo, ureidophenyl, nicotinamido, isonicotinamido, picolinamido, anilino or benzamido group that is unsubstituted or is itself substituted (optionally substituted) at the para-position when a 6-membered ring or the 3-position when a 5-membered ring. Here, single atoms such as halogen moieties or substituents that contain one to a chain of about ten atoms other than hydrogen such as $C_1$–$C_{10}$ hydrocarbyl, $C_1$–$C_9$ hydrocarbyloxy or carboxyethyl groups can be used.

Exemplary particularly preferred substituted $PhR^3$ (particularly preferred substituted $R^1$) substituents include biphenyl, 4-phenoxyphenyl, 4-thiophenoxyphenyl, 4-benzamidophenyl, 4-ureidophenyl, 4-anilinophenyl, 4-nicotinamido, 4-isonicotinamido, and 4-picolinamido. Exemplary particularly preferred $R^3$ groups contain a 6-membered aromatic ring and include a phenyl group, a phenoxy group, a thiophenoxy group, a phenylazo group, an ureidophenyl group, an anilino group, a nicotinamido group, an isonicotinamido group, a picolinamido group and a benzamido group.

More specifically, a particularly preferred sulfonyl butanhydroxamate compounds has an $R^3$ substituent that is a phenyl group, a phenoxy group, a thiophenoxy group, a phenylazo group, an ureidophenyl group, an anilino group, a nicotinamido group, an isonicotinamido group, a picolinamido group or a benzamido group that is itself optionally substituted at its own meta or para-position or both with a moiety that is selected from the group consisting of a halogen, a $C_1$–$C_9$ hydrocarbyloxy (—O—$C_1$–$C_9$ hydrocarbyl) group, a $C_1$–$C_{10}$ hydrocarbyl group, a di-$C_1$–$C_9$ hydrocarbylamino [—N($C_1$–$C_9$ hydrocarbyl)($C_1$–$C_9$ hydrocarbyl)] group, a carboxyl $C_1$–$C_8$ hydrocarbyl ($C_1$–$C_8$ hydrocarbyl-$CO_2H$) group, a $C_1$–$C_4$ hydrocarbyloxy carbonyl $C_1$–$C_4$ hydrocarbyl [$C_1$–$C_4$ hydrocarbyl-O—(CO)—$C_1$–$C_4$ hydrocarbyl]group, a $C_1$–$C_4$ hydrocarbyloxycarbonyl $C_1$–$C_4$ hydrocarbyl [$C_1$–$C_4$ hydrocarbyl(CO)—O—$C_1$–$C_4$ hydrocarbyl] group and a $C_1$–$C_8$ hydrocarbyl carboxamido [—NH(CO)-$C_1$–$C_8$ hydrocarbyl] group, or is substituted at the meta- and para-positions by two methyl groups or by a $C_1$–$C_2$ alkylenedioxy group such as a methylenedioxy group.

Inasmuch as a contemplated $SO_2$-linked cyclohydrocarbyl, heterocyclo, aryl or heteroaryl radical is itself preferably substituted with a 6-membered aromatic ring, two nomenclature systems are used together herein for ease in understanding substituent positions. The first system uses position numbers for the ring directly bonded to the $SO_2$-group, whereas the second system uses ortho, meta or para for the position of one or more substituents of a 6-membered ring bonded to a $SO_2$-linked cyclohydrocarbyl, heterocyclo, aryl or heteroaryl radical. When a $R^3$ substituent is other than a 6-membered ring, substituent positions are numbered from the position of linkage to the aromatic or heteroaromatic ring. Formal chemical nomenclature is used in naming particular compounds.

Thus, the 1-position of an above-discussed $SO_2$-linked cyclohydrocarbyl, heterocyclo, aryl or heteroaryl radical is the position at which the $SO_2$-group is bonded to the ring. The 4- and 3-positions of rings discussed here are numbered from the sites of substituent bonding from the $SO_2$-linkage as compared to formalized ring numbering positions used in heteroaryl nomenclature.

In particularly preferred practice, $R^1$ contains a phenyl group (Ph) linked at its own 4-position to another substituent, $R^3$, so that $R^1$ is $PhR^3$, and a contemplated compound has a structure that corresponds to Formula II, below, wherein $R^2$ is as before defined and $R^3$ is as defined below.

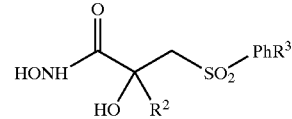

II

A particularly preferred $R^3$ substituent of an $SO_2$-linked Ph group is a single-ringed aryl or heteroaryl, phenoxy, thiophenoxy, phenylazo, ureidophenyl, nicotinamido, isonicotinamido, picolinamido, anilino or benzamido group that is unsubstituted or is itself substituted (optionally substituted) at the para-position when a six-membered ring or the 3-position when a five-membered ring. Here, single atoms such as halogen moieties or substituents that contain one to a chain of about ten atoms other than hydrogen such as $C_1$–$C_{10}$ hydrocarbyl, $C_1$–$C_9$ hydrocarbyloxy or carboxyethyl groups can be used.

Exemplary particularly preferred substituted $R^1$ $PhR^3$ substituents include biphenyl, 4-phenoxyphenyl, 4-thiophenoxyphenyl, 4-benzamidophenyl, 4-ureidophenyl, 4-anilinophenyl, 4-nicotinamido, 4-isonicotinamido, and 4-picolinamido. Exemplary particularly preferred $R^3$ groups contain a six-membered aromatic ring and include a phenyl group, a phenoxy group, a thiophenoxy group, a phenylazo group, an ureidophenyl group, an anilino group, a nicotinamido group, an isonicotinamido group, a picolinamido group and a benzamido group.

In one embodiment of a particularly preferred aromatic sulfonyl alpha-hydroxy hydroxamate compound, an $R^3$ substituent is a phenyl, phenoxy, anilino or thiophenoxy group that is itself optionally substituted at its own meta or para-position or both with a moiety that is selected from the group consisting of a halogen, a $C_1$–$C_9$ hydrocarbyloxy (—O—$C_1$–$C_9$ hydrocarbyl) group, a $C_1$–$C_{10}$ hydrocarbyl group, a di-$C_1$–$C_9$ hydrocarbylamino [—N($C_1$–$C_9$ hydrocarbyl)($C_1$–$C_9$ hydrocarbyl)] group, a carboxyl $C_1$–$C_8$ hydrocarbyl ($C_1$–$C_8$ hydrocarbyl-$CO_2H$) group, a $C_1$–$C_4$ hydrocarbyloxy carbonyl $C_1$–$C_4$ hydrocarbyl [$C_1$–$C_4$ hydrocarbyl-O—(CO)—$C_1$–$C_4$ hydrocarbyl] group, a $C_1$–$C_4$ hydrocarbyloxycarbonyl $C_1$–$C_4$ hydrocarbyl [$C_1$–$C_4$ hydrocarbyl(CO)—O—$C_1$–$C_4$ hydrocarbyl] group and a $C_1$–$C_8$ hydrocarbyl carboxamido [—NH(CO)—$C_1$–$C_8$ hydrocarbyl] group, or is substituted at the meta- and para-positions by two methyl groups or by a $C_1$–$C_2$ alkylenedioxy group such as a methylenedioxy group. These compounds generally exhibit good activities ($IC_{50}$ values of about 0.1–60 nM) against MMP-2, MMP-9 and MMP-13, while exhibiting substantially less activity toward MMP-1 ($IC_{50}$ values of about 1000 to >10,000 nM). An unsubstituted phenoxy or thiophenoxy $R^3$ substituent is presently preferred.

In another embodiment of a particularly preferred aromatic sulfonyl alpha-hydroxy hydroxamate compound, a $R^3$ substituent is benzamido, nicotinamido, isonicotinamido, picolinamido or ureidophenyl in which the substituent ring (benzamido, nicotinamido, isonicotinamido, picolinamido or ureidophenyl group) is unsubstituted or is itself (optionally) substituted at its own metaor para-position. A preferred substituent moiety on the substituent ring is selected from the group consisting of a halogen, a nitro, a $C_1-C_8$ hydrocarbyl, $C_1-C_7$ hydrocarbyloxy, a $C_1-C_2$ alkylenedioxy, an amino, an $N-C_2-C_4$-hydroxyalkylamino [e.g., $-NH(C_4H_8OH)$] and an $N,N-C_2-C_4$-hydroxyalkylamino [e.g., $-N(C_2H_4OH)_2$] group. Some of these compounds exhibit more than a 100,000-fold difference in in vitro inhibitory activity against MMP-2 and MMP-1, and an about 2- to about 100-fold activity enhancement against MMP-2 over MMP-13, while still maintaining nanomolar activity against MMP-2. These compounds exhibited about a 10- to about 100-fold activity difference between MMP-2 and MMP-9. Such compounds illustrate one aspect of the activity and selectivity of inhibition of some of the contemplated compounds.

Inasmuch as a contemplated $SO_2$-linked aryl or heteroaryl radical is itself preferably substituted with a six-membered aromatic ring, two nomenclature systems are used together herein for ease in understanding substituent positions. The first system uses position numbers for the ring directly bonded to the $SO_2$-group, whereas the second system uses ortho, meta or para for the position of one or more substituents of a six-membered ring bonded to a $SO_2$-linked aryl or heteroaryl radical. When a $R^3$ substituent is other than a six-membered ring, substituent positions are numbered from the position of linkage to the aromatic or heteroaromatic ring. Formal chemical nomenclature is used in naming particular compounds.

Thus, the 1-position of an above-discussed $SO_2$-linked aryl or heteroaryl radical is the position at which the $SO_2$-group is bonded to the ring. The 4-and 3-positions of rings discussed here are numbered from the sites of substituent bonding from the $SO_2$-linkage as compared to formalized ring numbering positions used in heteroaryl nomenclature.

The length, width and the number of aromatic rings present in a $R^1$ substituent bonded to the $SO_2$ group is believed to play a role in the overall activity of a contemplated compound against MMP enzymes generally. The identity of the $R^1$ substituent group can also play a role in the activity of a compound against particular MMP enzymes. In addition, substitution at the alpha-position to the hydroxamic acid group; i.e., substitution on the carbon atom between the hydroxamic acid group and the methylene-$SO_2$ group, also appears to play a role in the specificity of a contemplated compound as an inhibitor of specific a MMP enzyme.

For example, the compound of Example 8 [N,2-dihydroxy-3-[(4-methoxyphenyl)sulfonyl]propanamide] whose $SO_2$-bonded aryl group is a 4-methoxyphenyl substituent having a length of about a six carbon chain (a hexyl group) was found to be relatively inactive as an inhibitor of MMP-1 and only slightly better against MMP-13. That lack of activity can be compared to the excellent activity exhibited by the compound of Example 9 [N,2-dihydroxy-3-[(4-phenoxyphenyl)sulfonyl]-propanamide that is substituted similarly at the alpha-position, but has a longer $R^1$ group (an about nine carbon chain). These comparative activities can be seen in Table 51 hereinafter.

The compounds of Examples 14–35 contain $PhR^3$ $R^1$ groups that include an amido [$-C(O)NH-$] functionality as part of the $R^1$ group. Those $R^1$ groups, depending upon the total length of $R^1$, appear to somewhat lessen the activity of the compounds toward MMP-13, while virtually eliminating any activity against MMP-1, and thus provide exquisite specificity in distinguishing between those two enzymes. This phenomenon appears to hold whether the $R^3$ group contains an aromatic moiety or an aliphatic moiety bonded to the amido group and whether the amido group is present as a $-C(O)NH-$ linkage or part of a ureido [$-NHC(O)NH-$] linkage. It thus appears as though compounds that contain an amido group-containing $R^1$ substituent are bound minimally, if at all, by MMP-1. These data are also shown in Table 51 hereinafter.

Those data of Table 51 also show the relative importance of overall length of the $R^1$ substituent as well as the relative benefit of that substituent having two aromatic rings. Thus, the compound of Example 24 [4-(heptyloxy)—N-[4-[[2-hydroxy-3-(hydroxyamino)-2-methyl-3-oxopropyl] sulfonyl]phenyl]benzamide], whose $R^1$ group has a length of about an 18-carbon chain exhibited potencies against MMP-13 and MMP-2 that were greater than could be measured in the assay, and an activity against MMP-1 that was lower than could be measured in the assay. Comparison of the data in Table 51 for the compounds of Examples 16 and 17 {N-[4-[[2-hydroxy-3-(hydroxyamino)-2-methyl-3-oxopropyl]-sulfonyl]phenyl]benzamide and N-[4-[[2-hydroxy-3-(hydroxyamino)-2-methyl-3-oxopropyl] sulfonyl]phenyl]-3-methylbutanamide] for compounds whose $R^1$ groups are almost the same length shows the compound with two aromatic rings to be more active.

It is also preferred that the $R^1$ substituent contain a thioether linkage, as is present in a thiophenoxy $R^3$ group. This preference can be seen by comparison of the activities in Table 51 of similarly substituted compounds whose $R^1$ groups differ in the presence or absence of a thioether group as in the compounds of Examples 2 and 13 or 9 and 12.

A contemplated matrix compound contains an asymmetric carbon atom at the alpha-position so that enantiomeric, d and l or R and S, forms of each compound exist. Particularly preferred stereoconfigurations for a contemplated enantiomeric compound are shown below in Formulas III and IV

III

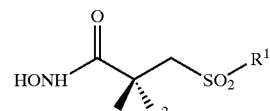

IV

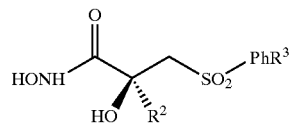

In the above formulas, the dashed line represents a bond that extends beneath the plane of the page, whereas the solid wedge-shaped line represents a bond that extends above the plane of the page, as is usual in stereochemical depictions. Where the $R^2$ group is methyl, a contemplated compound of Formulas III or IV have the S stereoconfiguration.

Examination of X-ray crystallographic data of a complex of a contemplated compound bound to MMP-8, an enzyme which is quite similar to MMP-13, indicates that an intramolecular hydrogen bond is formed between the alpha-hydroxyl group and a sulfonyl group oxygen of an compound having the stereoconfiguration shown in Formulas III or IV. The observation of this hydrogen bond was unexpected. The conformation of the bound inhibitor (Example 1A) appears to allow the intramolecular hydrogen bond for only this stereoisomer. That hydrogen bond cannot form from a compound of the opposite configuration while maintaining (a) the orientation of the hydroxamate group toward the metal ion of the enzyme and (b) the position of the $R^1$ group in the binding pocket of the enzyme. This may account for the better binding of this compound to MMP-13, -2 and -9, compared to a compound of the opposite configuration (compound of Example 1B) (See Table 51 for enzyme data).

Intramolecular hydrogen bonds are well known to those skilled in the art. Although the S stereoisomer of Example 1A is preferred, both configurations permit this favorable intramolecular interaction in solution. The advantages of such intramolecular hydrogen-bonding for medicaments have been reported by several research groups. See, for example, Smith, et al. *J. med. Chem.* (1994) 37(2), 215–218 and Leone-Bay et al. *J. Med. Chem.* (1996) 39(13), 2571–2578.

The data shown in Table 51 illustrate better binding for a compound of the above configuration (compound of Example 1A) to MMP-13, -2 and -9 than a compound of the opposite configuration (compound of Example 1B). Binding of both compounds to MMP-1 was within about a factor of ten. However, because of the better binding of the compound of Example 1A to MMP-13, the ratio of inhibition of MMP-1 to inhibition of MMP-13 was about 2-times greater for the compound of the above stereoconfiguration (Exhibit 1A compound) than for the compound of opposite configuration. The advantages of such intramolecular hydrogen-bonding for medicaments have been reported by several research groups. See, for example, Smith, et al., *J. Med. Chem.* (1994) 37(2), 215–218 and Leone-Bay et al., *J. Med. Chem.* (1996) 39(13), 2571–2578.

The word "hydrocarbyl" is used herein as a short hand term to include straight and branched chain aliphatic as well as alicyclic groups or radicals that contain only carbon and hydrogen. Thus, alkyl, alkenyl and alkynyl groups are contemplated, whereas aromatic hydrocarbons such as phenyl and naphthyl groups, which strictly speaking are also hydrocarbyl groups, are referred to herein as aryl groups or radicals, as discussed hereinafter. Where a specific aliphatic hydrocarbyl substituent group is intended, that group is recited; i.e., $C_1-C_4$ alkyl, methyl or dodecenyl. Exemplary hydrocarbyl groups contain a chain of 1 to about 12 carbon atoms, and preferably one to about 10 carbon atoms. A particularly preferred hydrocarbyl group is an alkyl group.

Usual chemical suffix nomenclature is followed when using the word "hydrocarbyl" except that the usual practice of removing the terminal "yl" and adding an appropriate suffix is not always followed because of the possible similarity of a resulting name to one or more substituents. Thus, a hydrocarbyl ether is referred to as a "hydrocarbyloxy" group rather than a "hydrocarboxy" group as may possibly be more proper when following the usual rules of chemical nomenclature. On the other hand, a hydrocarbyl group containing a —C(O)O — functionality is referred to as a hydrocarboyl group inasmuch as there is no ambiguity in using that suffix. As a skilled worker will understand, a substituent that cannot exist such as a $C_1$ alkenyl group is not intended to be encompassed by the word "hydrocarbyl".

As stated before, a particularly preferred hydrocarbyl group is an alkyl group. As a consequence, a generalized, but more preferred substituent can be recited by replacing the descriptor "hydrocarbyl" with "alkyl" in any of the substituent groups enumerated herein.

Examples of alkyl radicals include methyl, ethyl, n-propyl, isopropyl, n-butyl, isobutyl, sec-butyl, tert-butyl, pentyl, iso-amyl, hexyl, octyl and the like. Examples of suitable alkenyl radicals include ethenyl (vinyl), 2-propenyl, 3-propenyl, 1,4-pentadienyl, 1,4-butadienyl, 1-butenyl, 2-butenyl, 3-butenyl, decenyl and the like. Examples of alkynyl radicals include ethynyl, 2-propynyl, 3-propynyl, decynyl, 1-butynyl, 2-butynyl, 3-butynyl, and the like.

The term "carbonyl", alone or in combination, means a —C(=O)— group wherein the remaining two bonds (valences) are independently substituted. The term "thiol" or "sulfhydryl", alone or in combination, means a —SH group. The term "thio" or "thia", alone or in combination, means a thiaether group; i.e., an ether group wherein the ether oxygen is replaced by a sulfur atom.

The term "amino", alone or in combination, means an amine or —$NH_2$ group, whereas the term mono-substituted amino, alone or in combination, means a substituted amine —N(H) (substituent) group wherein one hydrogen atom is replaced with a substituent, and disubstituted amine means a —N(substituent)$_2$ wherein two hydrogen atoms of the amino group are replaced with independently selected substituent groups. Amines, amino groups and amides are classes that can be designated as primary (I°), secondary (II°) or tertiary (III°) or unsubstituted, mono-substituted or di-substituted depending on the degree of substitution of the amino nitrogen. Quaternary amine (IV°) means a nitrogen with four substituents (—$N^+$(substituent)$_4$) that is positively charged and accompanied by a counter ion or N-oxide means one substituent is oxygen and the group is represented as (—$N^+$(substituent)$_3$—$O^-$); i.e., the charges are internally compensated.

The term "cyano", alone or in combination, means a —C-triple bond-N (—CN) group. The term "azido", alone or in combination, means a —N-double bond-N-double bond-N (—N=N=N) group.

The term "hydroxyl", alone or in combination, means a —OH group. The term "nitro", alone or in combination, means a —$NO_2$ group.

The term "azo", alone or in combination, means a —N=N— group wherein the bonds at the terminal positions are independently substituted. The term "hydrazino", alone or in combination, means a —NH—NH— group wherein the remaining two bonds (valences) are independently substituted. The hydrogen atoms of the hydrazino group can be replaced, independently, with substituents and the nitrogen atoms can form acid addition salts or be quaternized.

The term "sulfonyl", alone or in combination, means a —S(=O)$_2$— group wherein the remaining two bonds (valences) can be independently substituted. The term "sulfoxido", alone or in combination, means a —S(=O)$_1$- group wherein the remaining two bonds (valences) can be independently substituted. The term "sulfonylamide", alone or in combination, means a —S(=O)$_2$—N= group wherein the remaining three bonds (valences) are independently substituted. The term "sulfinamido", alone or in combination, means a —S(=O)$_1$N= group wherein the remaining three bonds (valences) are independently substituted. The term "sulfenamide", alone or in combination, means a —S—N= group wherein the remaining three bonds (valences) are independently substituted.

The term "hydrocarbyloxy", alone or in combination, means an hydrocarbyl ether radical wherein the term hydrocarbyl is as defined above. Examples of suitable hydrocarbyl ether radicals include methoxy, ethoxy, n-propoxy, isopropoxy, allyloxy, n-butoxy, iso-butoxy, sec-butoxy, tert-butoxy and the like. The term "cyclohydrocarbyl", alone or in combination, means a hydrocarbyl radical that contains 3 to about 8 carbon atoms, preferably from about 3 to about 6 carbon atoms, and is cyclic. Examples of such cyclohydrocarbylhydrocarbyl radicals include cyclopropyl, cyclobutyl, cyclopentenyl, cyclohexyl cyclooctynyl and the like. The term "cyclohydrocarbylhydrocarbyl" means an hydrocarbyl radical as defined above which is substituted by a cyciohydrocarbyl as also defined above.

The term "aryl", alone or in combination, means a phenyl or naphthyl radical that optionally carries one or more substituents selected from hydrocarbyl, hydrocarbyloxy, halogen, hydroxy, amino, nitro and the like, such as phenyl, p-tolyl, 4-methoxyphenyl, 4-(tert-butoxy)phenyl, 4-fluorophenyl, 4-chlorophenyl, 4-hydroxyphenyl, and the like. The term "arylhydrocarbyl", alone or in combination, means an hydrocarbyl radical as defined above in which one hydrogen atom is replaced by an aryl radical as defined above, such as benzyl, 2-phenylethyl and the like. The term "arylhydrocarbyloxycarbonyl", alone or in combination, means a radical of the formula —C(O)—O-arylhydrocarbyl in which the term "arylhydrocarbyl" has the significance given above. An example of an arylhydrocarbyloxycarbonyl radical is benzyloxycarbonyl. The term "aryloxy" means a radical of the formula aryl-O— in which the term aryl has the significance given above. The term "aromatic ring" in combinations such as substituted-aromatic ring sulfonamide, substituted-aromatic ring sulfinamide or substituted-aromatic ring sulfenamide means aryl or heteroaryl as defined above.

The terms "hydrocarbyloyl" or "hydrocarbylcarbonyl", alone or in combination, mean an acyl radical derived from an hydrocarbylcarboxylic acid, examples of which include acetyl, propionyl, acryloyl, butyryl, valeryl, 4-methylvaleryl, and the like. The term "cyclohydrocarbylcarbonyl" means an acyl group derived from a monocyclic or bridged cyclohydrocarbylcarboxylic acid such as cyclopropanecarbonyl, cyclohexenecarbonyl, adamantanecarbonyl, and the like, or from a benz-fused monocyclic cyclohydrocarbylcarboxylic acid that is optionally substituted by, for example, a hydrocarbyloylamino group, such as 1,2,3,4-tetrahydro-2-naphthoyl, 2-acetamido-1,2,3,4-tetrahydro-2-naphthoyl. The terms "arylhydrocarbyloyl" or "arylhydrocarbylcarbonyl" mean an acyl radical derived from an aryl-substituted hydrocarbylcarboxylic acid such as phenylacetyl, 3-phenylpropenyl (cinnamoyl), 4-phenylbutyryl, (2-naphthyl)acetyl, 4-chlorohydrocinnamoyl, 4-aminocinnamoyl, 4-methoxycinnamoyl and the like.

The terms "aroyl" or "arylcarbonyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-(benzyloxycarbonyl) benzoyl, 2-naphthoyl, 6-carboxy-2 naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The heterocyclyl (heterocyclo) or heterocyclohydrocarbyl portion of a heterocyclylcarbonyl, heterocyclyloxycarbonyl, heterocyclylhydrocarbyloxycarbonyl, or heterocclohydrocarbyl group or the like is a saturated or partially unsaturated monocyclic, bicyclic or tricyclic heterocycle that contains one to four hetero atoms selected from nitrogen, oxygen and sulphur, which is optionally substituted on one or more carbon atoms by a halogen, alkyl, alkoxy, oxo group, and the like, and/or on a secondary nitrogen atom (i.e., —NH—) by an hydrocarbyl, arylhydrocarbyloxycarbonyl, hydrocarbyloyl, aryl or arylhydrocarbyl or on a tertiary nitrogen atom (i.e. =N—) by oxido and that is attached via a carbon atom. The tertiary nitrogen atom with three substituents can also form a N-oxide [=N(O)—] group. Examples of such heterocyclyl groups are pyrrolidinyl, piperidinyl, piperazinyl, morpholinyl, thiamorpholinyl, and the like.

The heteroaryl portion of a heteroaroyl, heteroaryloxycarbonyl, or a heteroarylhydrocarbyloyl (heteroarylhydrocarbyl carbonyl) group or the like is an aromatic monocyclic, bicyclic, or tricyclic heterocycle that contains the hetero atoms and is optionally substituted as defined above with respect to the definition of heterocyclyl. A "heteroaryl" group is an aromatic heterocyclic ring substituent that can contain one, two, three or four atoms in the ring that are other than carbon. Those heteroatoms can be nitrogen, sulfur or oxygen. A heteroaryl group can contain a single five- or 6-membered ring or a fused ring system that contains two 6-membered rings or a five- and a 6-membered ring. Exemplary heteroaryl groups include 6-membered ring substituents such as pyridyl, pyrazyl, pyrimidinyl, and pyridazinyl; 5-membered ring substituents such as 1,3,5-, 1,2,4- or 1,2,3-triazinyl, imidazyl, furanyl, thiophenyl, pyrazolyl, oxazolyl, isoxazolyl, thiazolyl, 1,2,3-, 1,2,4-, 1,2, 5-, or 1,3,4-oxadiazolyl and isothiazolyl groups; six/5-membered fused ring substituents such as benzothiofuranyl, isobenzothiofuranyl, benzisoxazolyl, benzoxazolyl, purinyl and anthranilyl groups; and six/6-membered fused rings such as 1,2-, 1,4-,2,3- and 2,1-benzopyronyl, quinolinyl, isoquinolinyl, cinnolinyl, quinazolinyl, and 1,4-benzoxazinyl groups.

The term "cyclohydrocarbylhydrocarbyloxycarbonyl" means an acyl group derived from a cyclohydrocarbylhydrocarbyloxycarboxylic acid of the formula cyclohydrocarbylhydrocarbyl-O—COOH wherein cyclohydrocarbylhydrocarbyl has the significance given above. The term "aryloxyhydrocarbyloyl" means an acyl radical of the formula aryl-O-hydrocarbyloyl wherein aryl and hydrocarbyloyl have the significance given above. The term "heterocyclyloxycarbonyl" means an acyl group derived from heterocyclyl-O—COOH wherein heterocyclyl is as defined above. The term "heterocyclylhydrocarbyloyl" is an acyl radical derived from a heterocyclyl-substituted hydrocarbylcarboxylic acid wherein heterocyclyl has the significance given above. The term "heterocyclylhydrocarbyloxycarbonyl" means an acyl radical derived from a heterocyclyl-substituted hydrocarbyl-O—COOH wherein heterocyclyl has the significance given above. The term "heteroaryloxycarbonyl" means an acyl radical derived from a carboxylic acid represented by heteroaryl-O—COOH wherein heteroaryl has the significance given above.

The term "aminocarbonyl" alone or in combination, means an amino-substituted carbonyl (carbamoyl) group derived from an amino-substituted carboxylic acid wherein the amino group can be a primary, secondary or tertiary amino group containing substituents selected from hydrogen, hydrocarbyl, aryl, aralkyl, cyclohydrocarbyl, cyclohydrocarbylhydrocarbyl radicals and the like. The ter, "aminohydrocarbyloyl" means an acyl group derived from an amino-substituted hydrocarbylcarboxylic acid wherein the amino group can be a primary, secondary or tertiary amino group containing substituents independently selected from hydrogen, alkyl, aryl, aralkyl, cyclohydrocarbyl, cyclohydrocarbylhydrocarbyl radicals and the like.

The term "halogen" means fluorine, chlorine, bromine or iodine. The term "halohydrocarbyl" means a hydrocarbyl radical having the significance as defined above wherein one or more hydrogens are replaced with a halogen. Examples of such halohydrocarbyl radicals include chloromethyl, 1-bromoethyl, fluoromethyl, difluoromethyl, trifluoromethyl, 1,1,1-trifluoroethyl and the like. The term perfluorohydrocarbyl means a hydrocarbyl group wherein each hydrogen has been replaced by a fluorine atom. Examples of such perfluorohydrocarbyl groups, in addition to trifluoromethyl above, are perfluorobutyl, perfluoroisopropyl, perfluorododecyl and perfluorodecyl.

Table 1 through Table 50, below, show several contemplated aromatic sulfonyl alpha-hydroxy hydroxamic acid compounds as structural formulas that illustrate substituent groups. Each group of compounds is illustrated by a generic formula, followed by a series of preferred moieties or groups that constitute various substituents that can be attached at the position clearly shown in the generic structure. The substituent symbols, e.g., $R^1$, are as shown in each Table. One bond (straight line) is shown with those substituents to indicate the respective positions of attachment in the illustrated compound. This system is well known in the chemical communication arts and is widely used in scientific papers and presentations.

TABLE 1

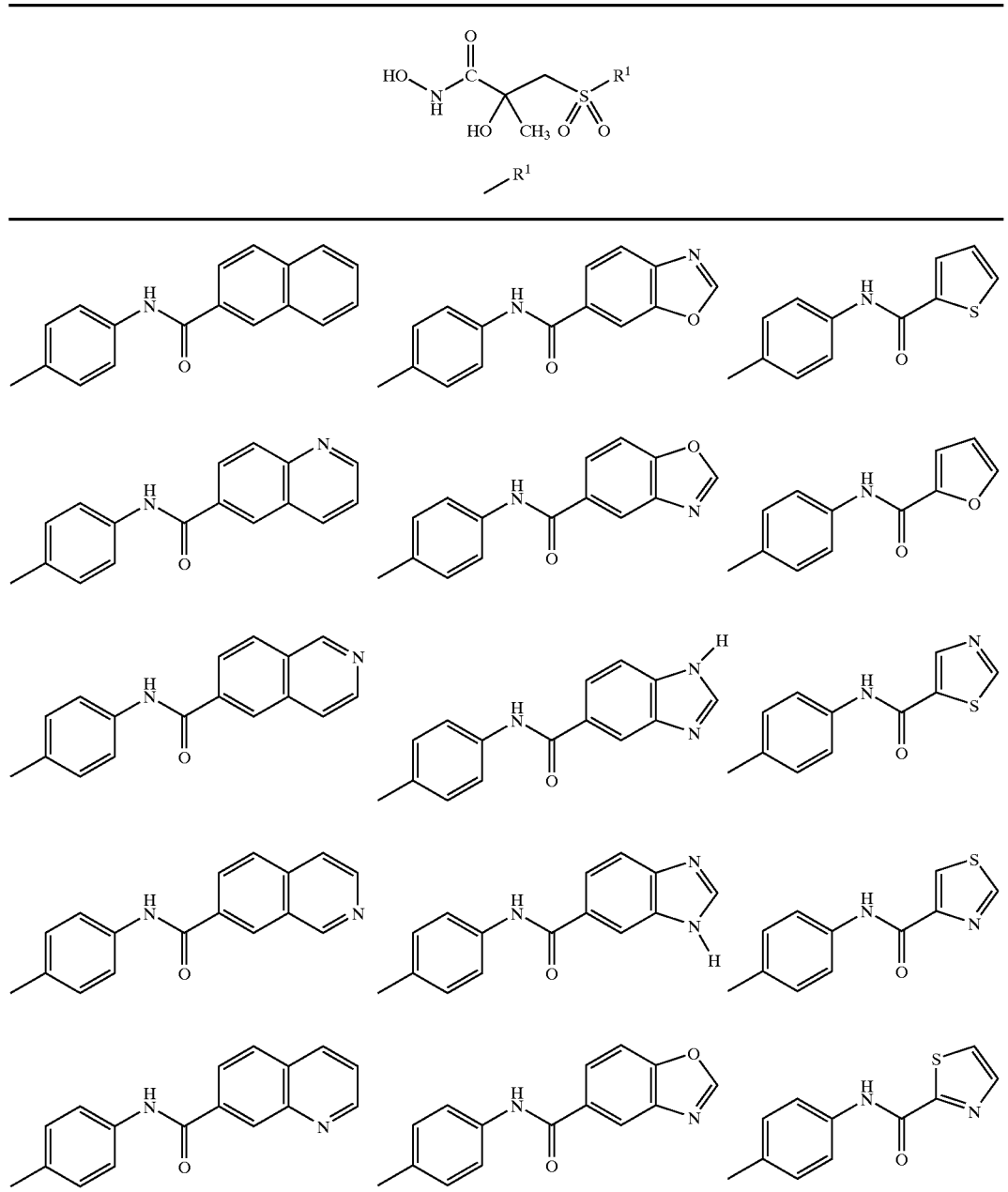

TABLE 1-continued
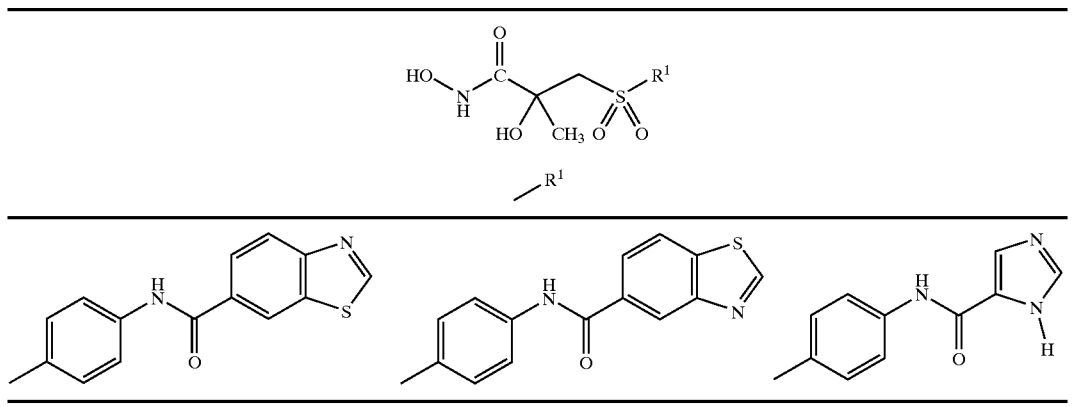
TABLE 2
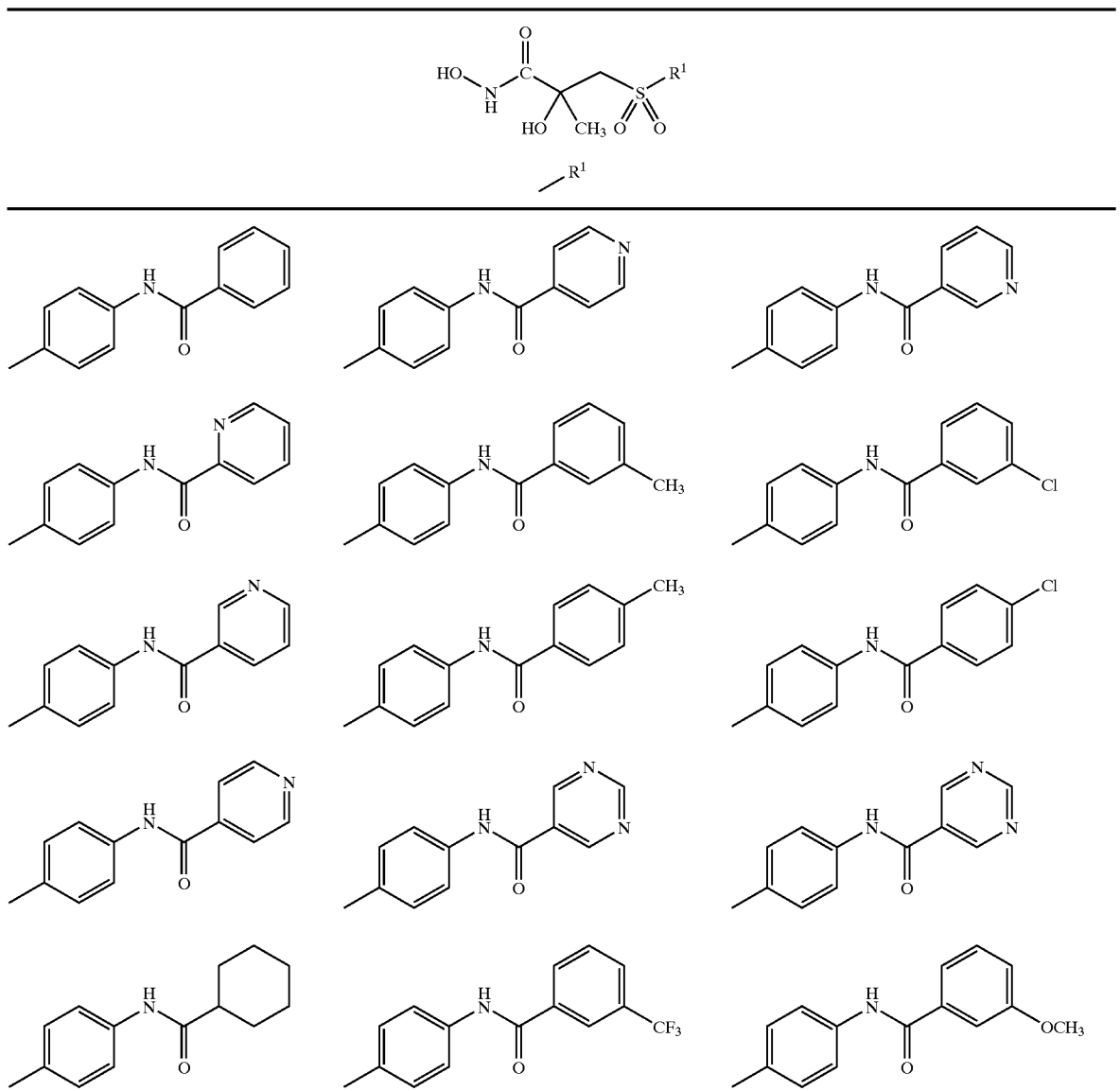

TABLE 2-continued
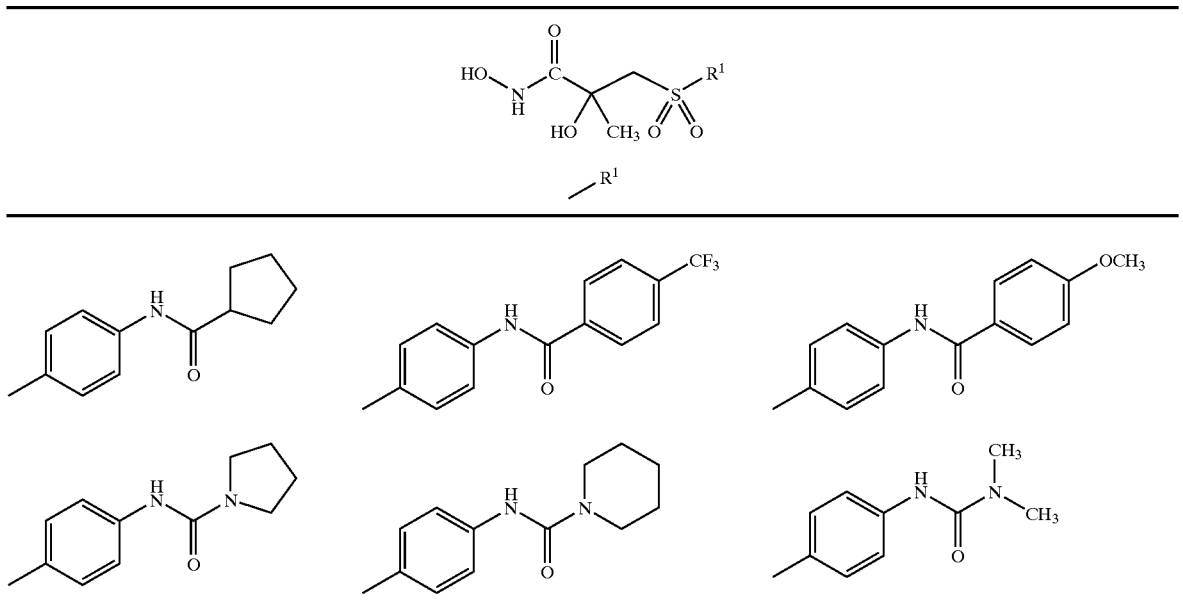
TABLE 3
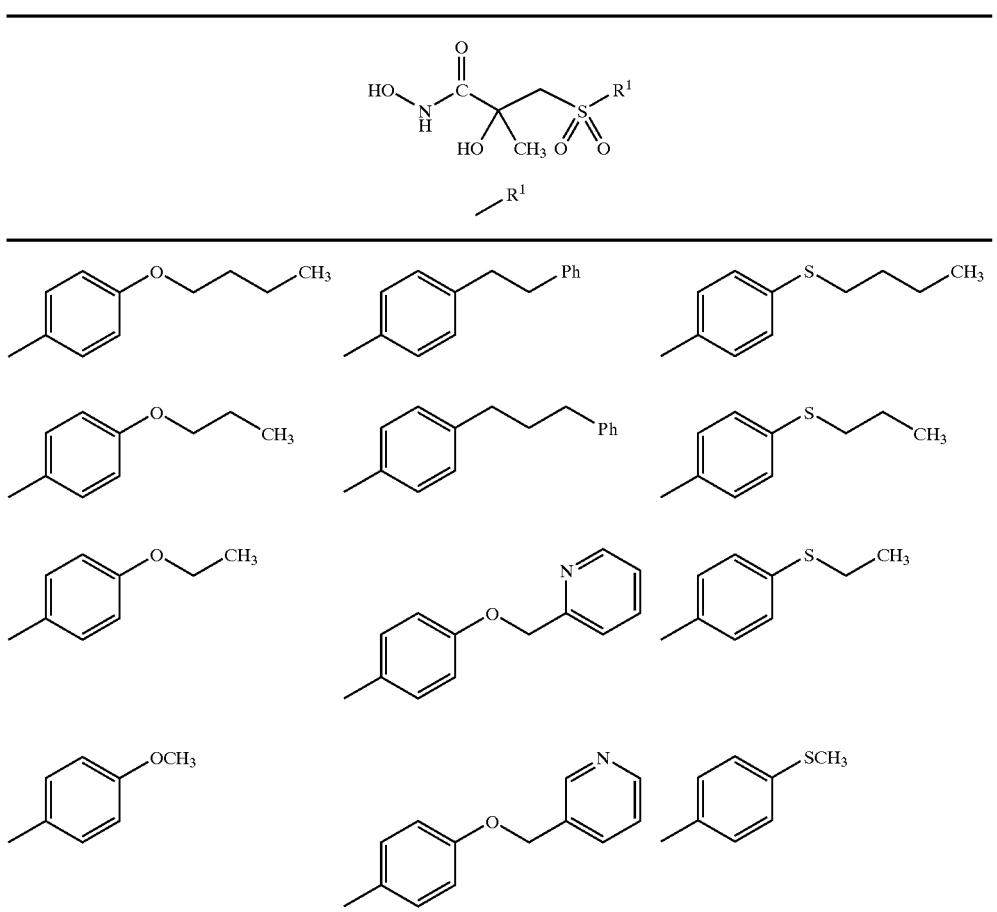

TABLE 3-continued
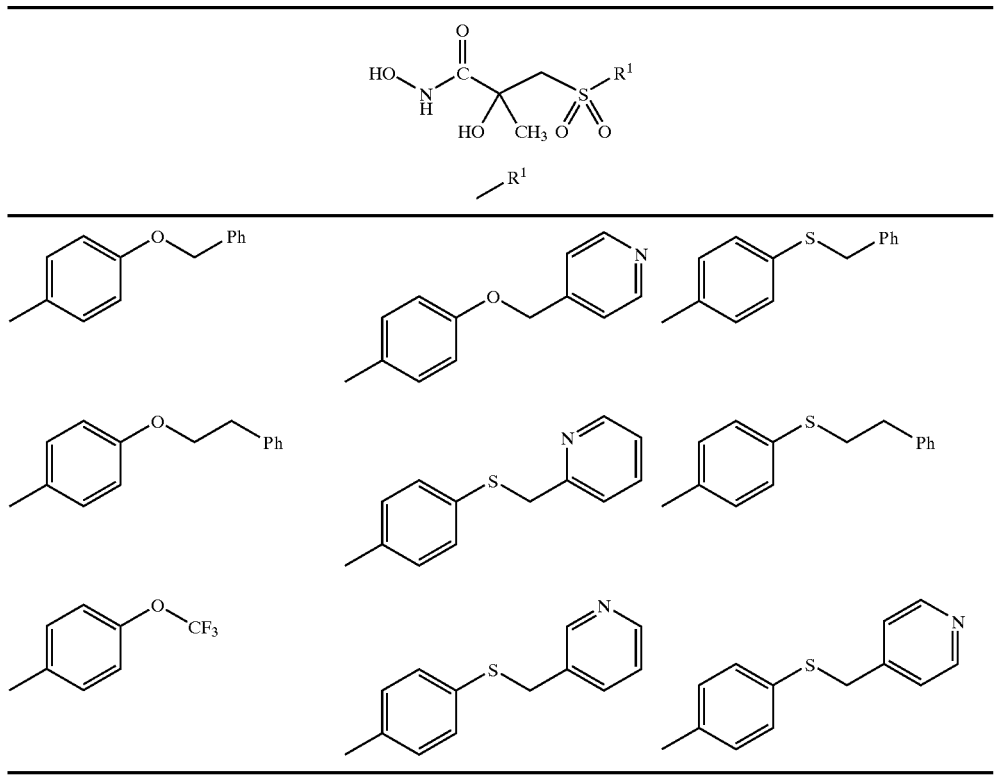
TABLE 4
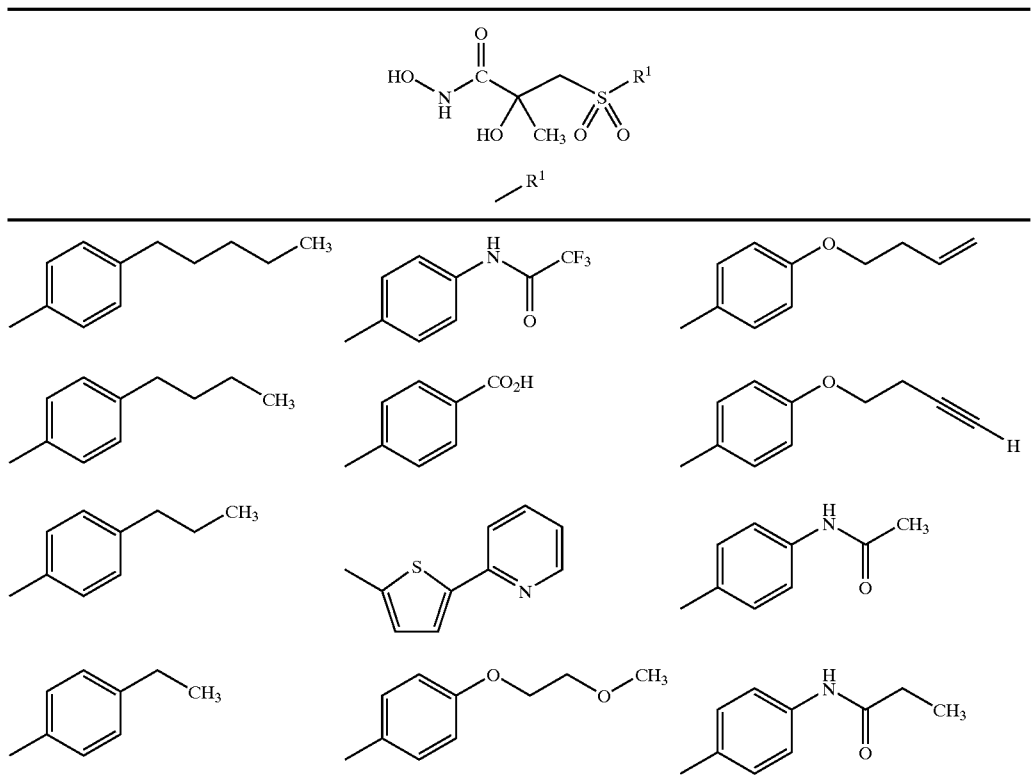

TABLE 4-continued
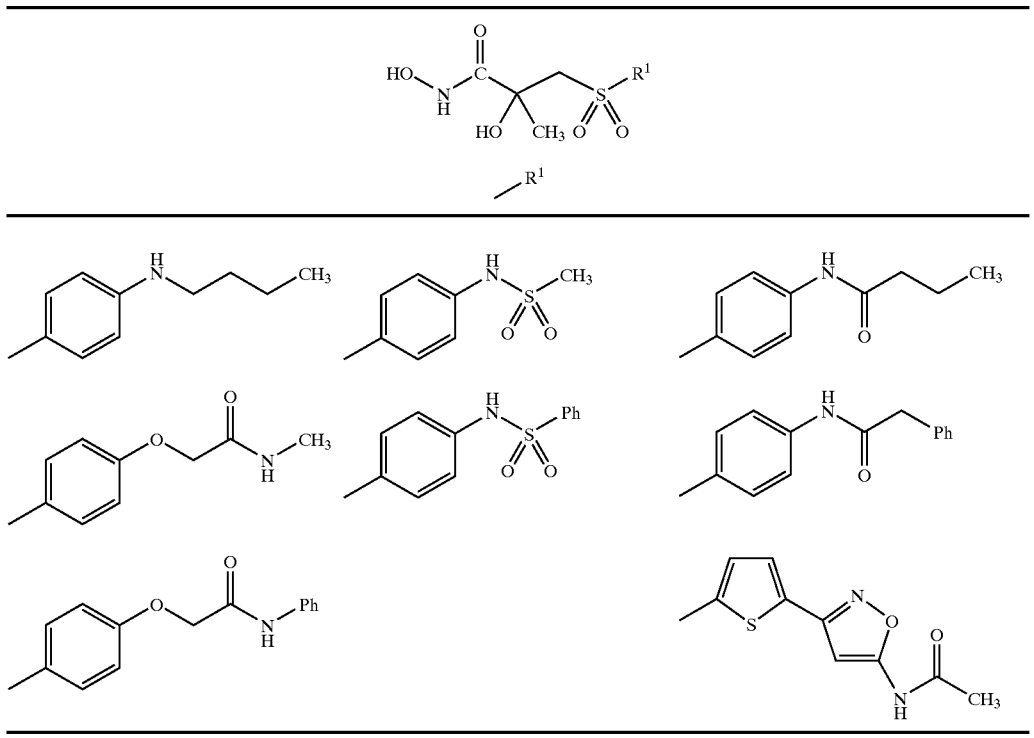
TABLE 5
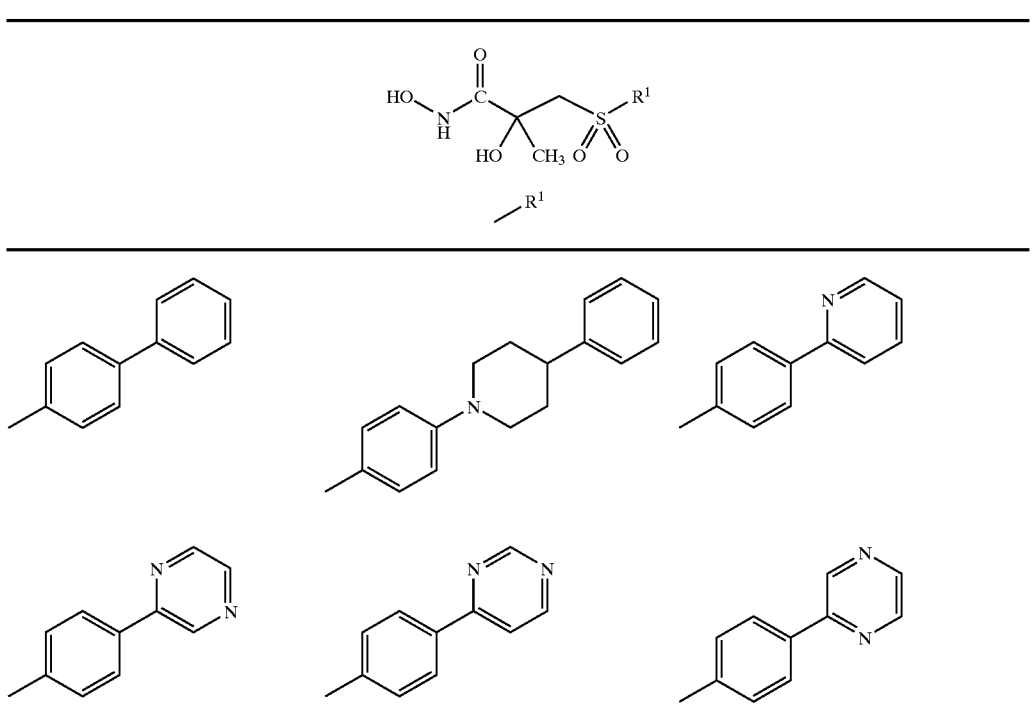

TABLE 5-continued
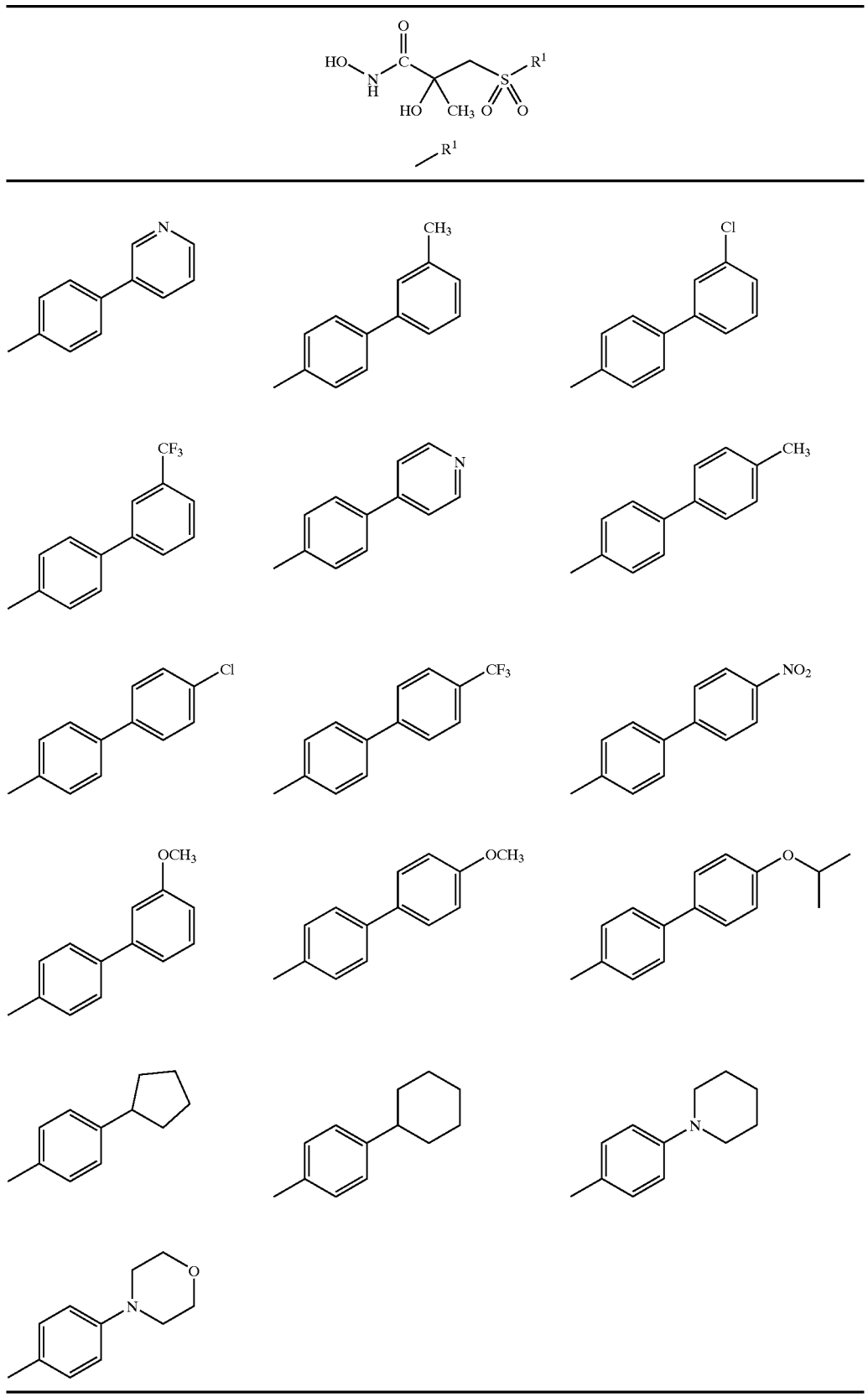

TABLE 6
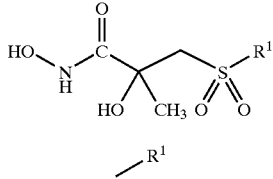
| —R¹ | | |
|---|---|---|
| 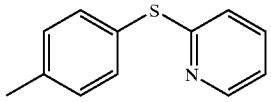 | 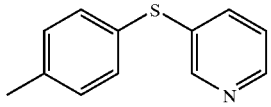 | 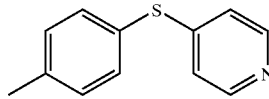 |
| 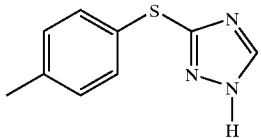 | 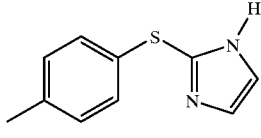 | 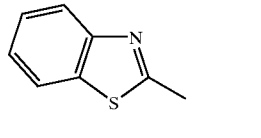 |
| 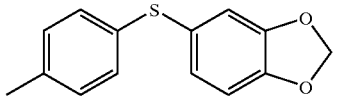 | | 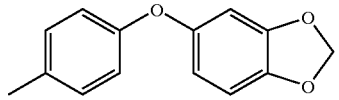 |
| 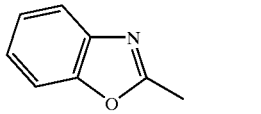 | 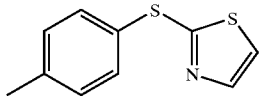 | 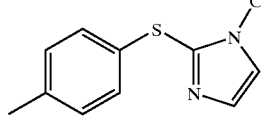 |
| 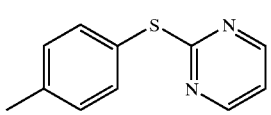 | 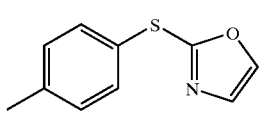 | 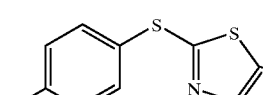 |
| 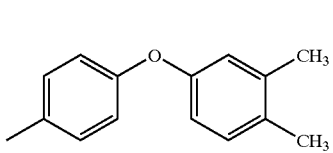 | | 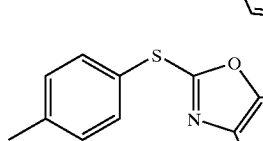 |
TABLE 7
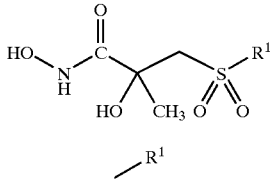
| —R¹ | | |
|---|---|---|
| 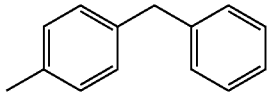 | 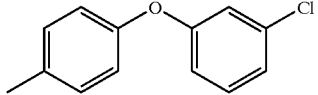 | 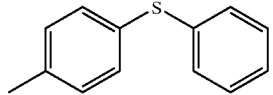 |

TABLE 7-continued
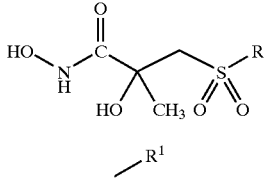
—R¹
| 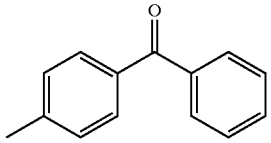 | 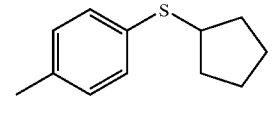 | 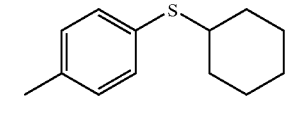 |
| 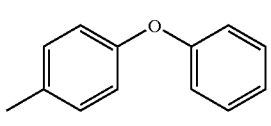 | 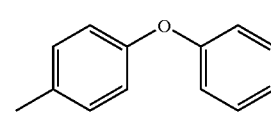 | 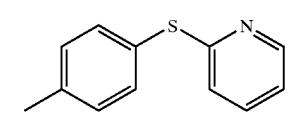 |
| 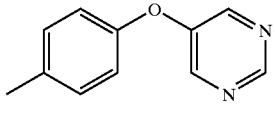 | 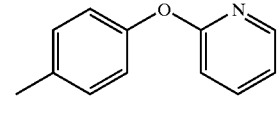 | 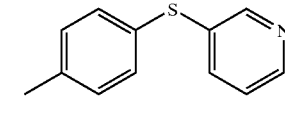 |
| 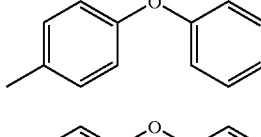 | 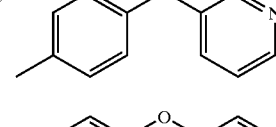 | 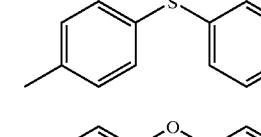 |
| 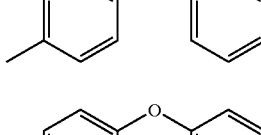 | 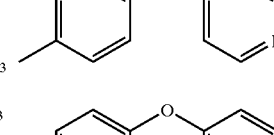 | 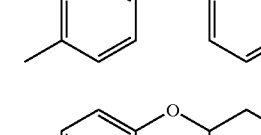 |
| 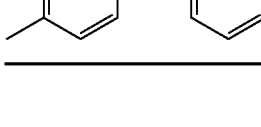 | 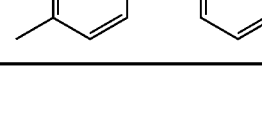 | 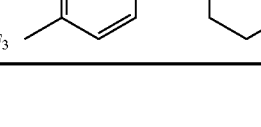 |
TABLE 8
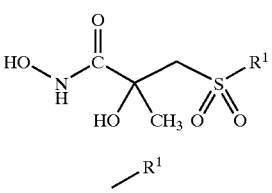
—R¹
| 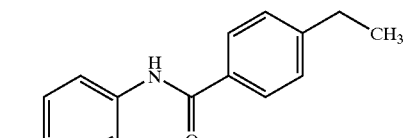 | 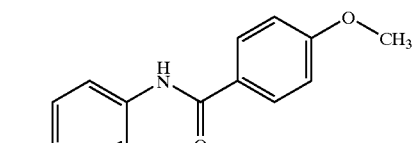 |

TABLE 8-continued
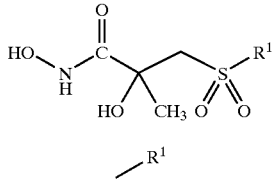
—R[1]
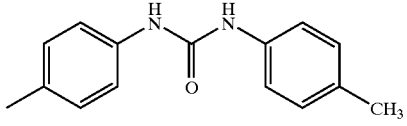 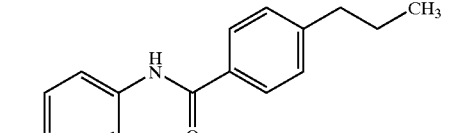
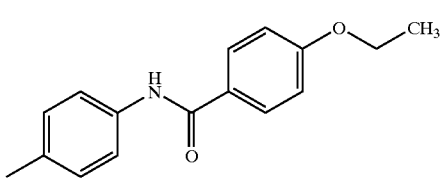 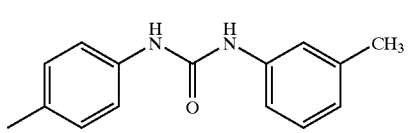
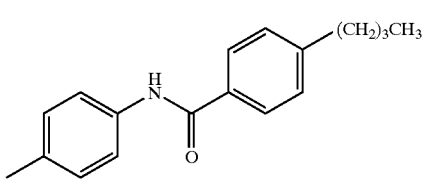 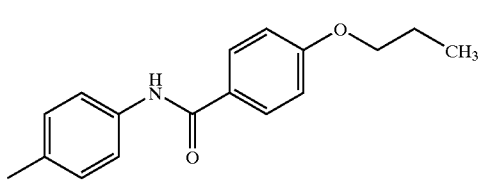
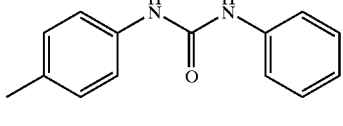 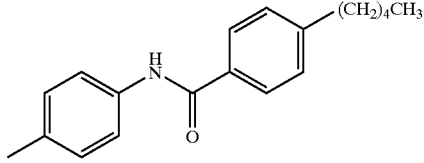
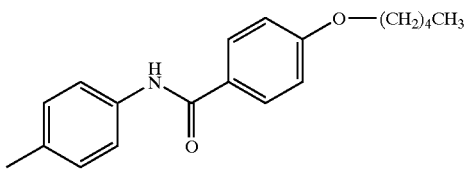 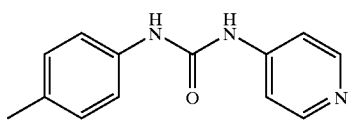
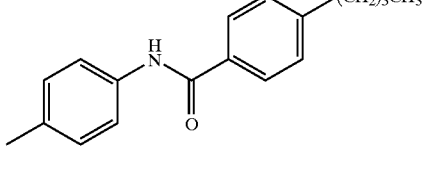 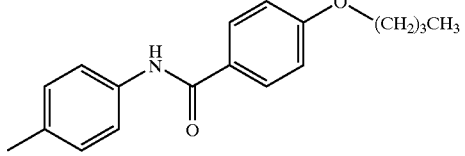
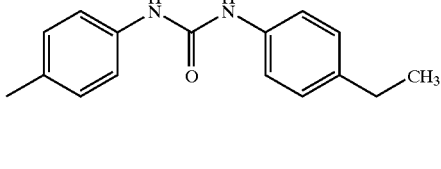 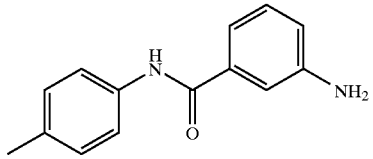
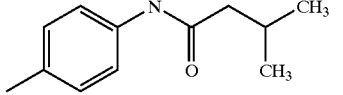 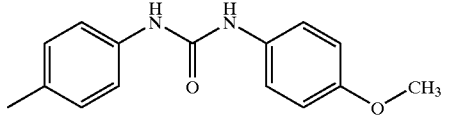

TABLE 8-continued
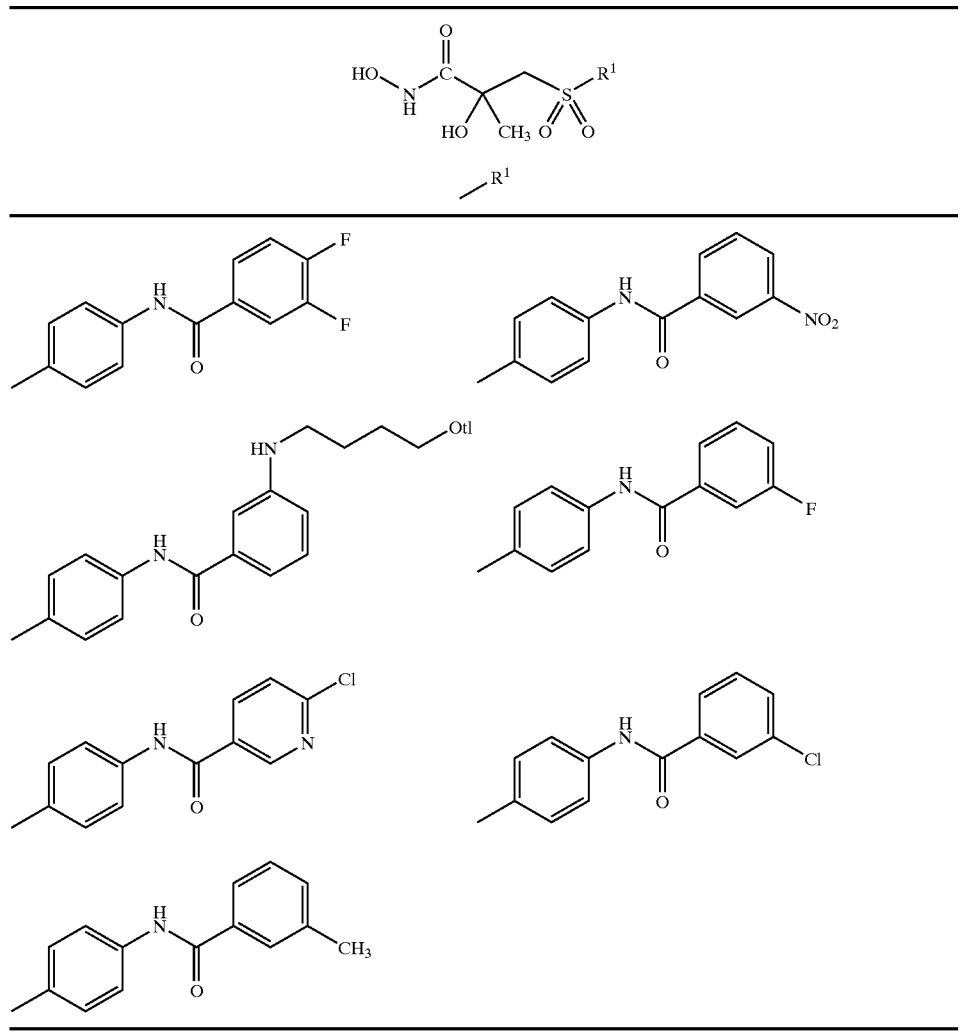
TABLE 9
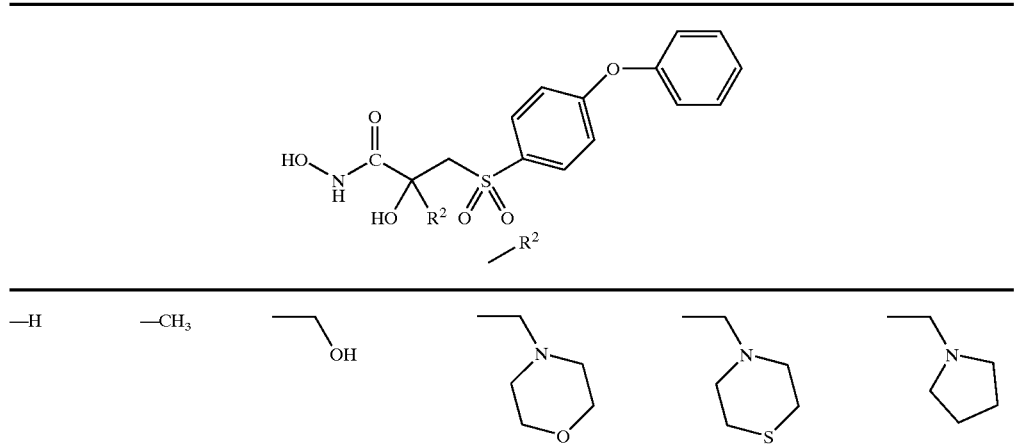

TABLE 9-continued

TABLE 10

TABLE 10-continued
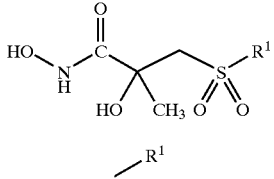
TABLE 11
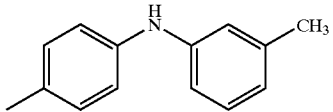

TABLE 11-continued
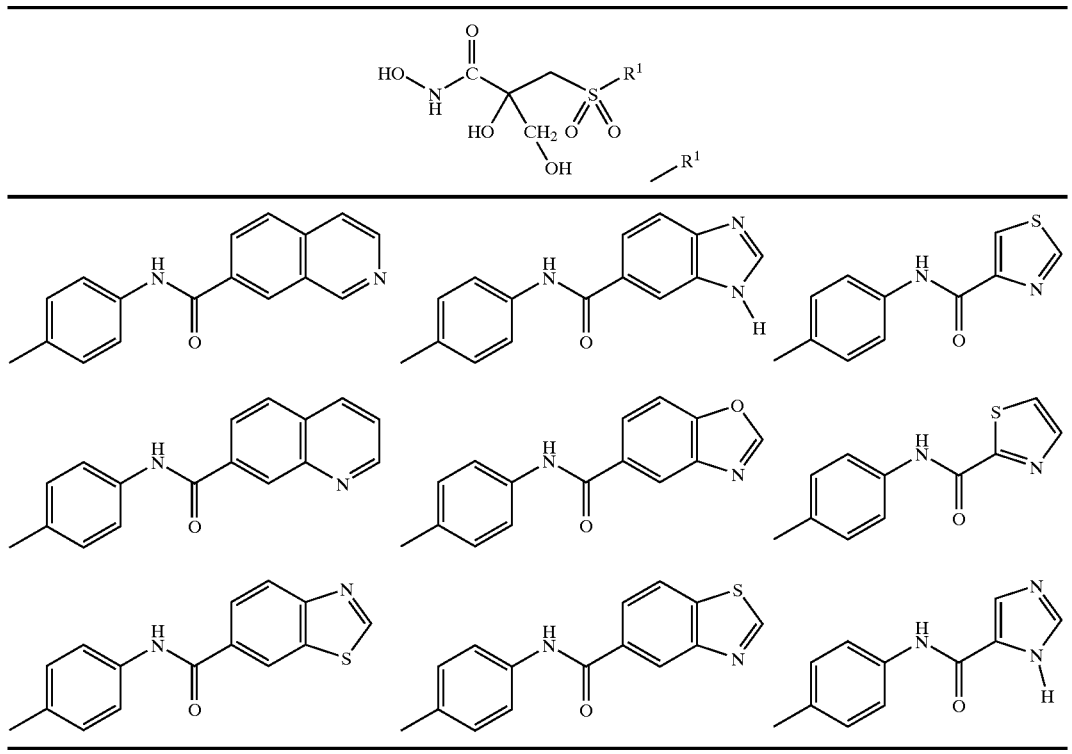
TABLE 12
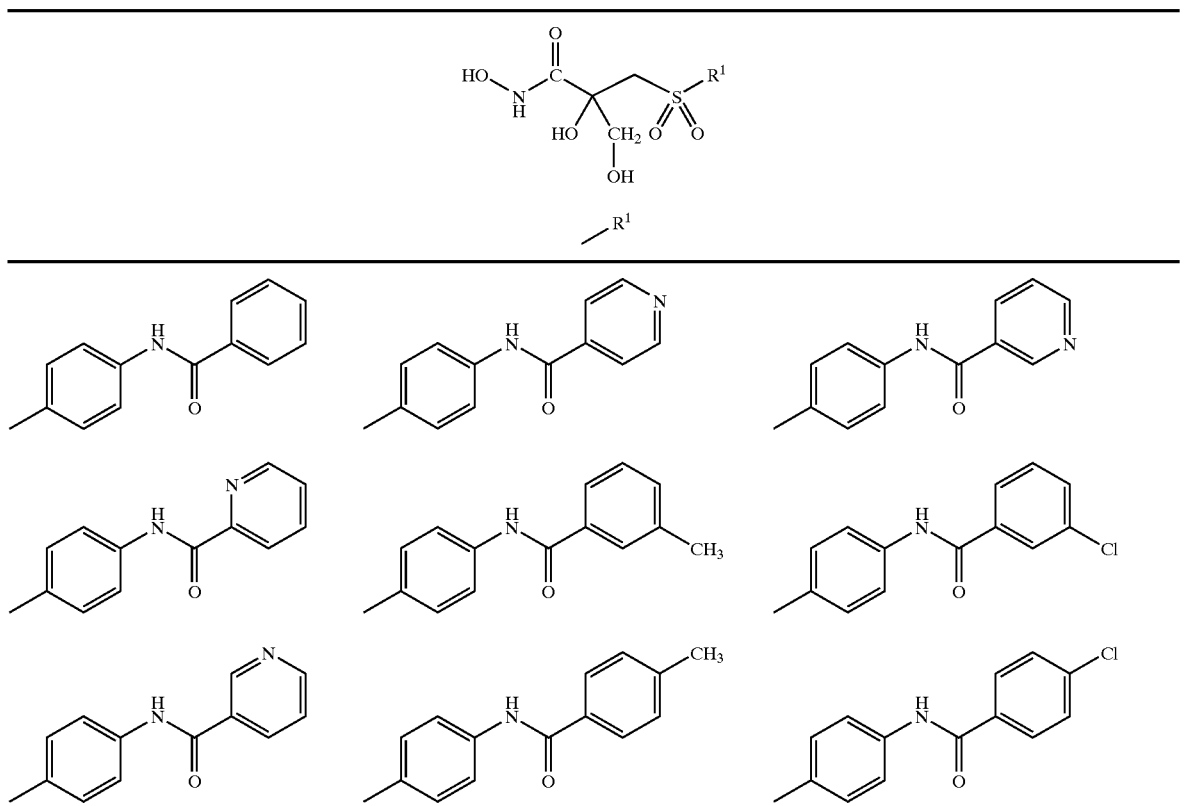

TABLE 12-continued
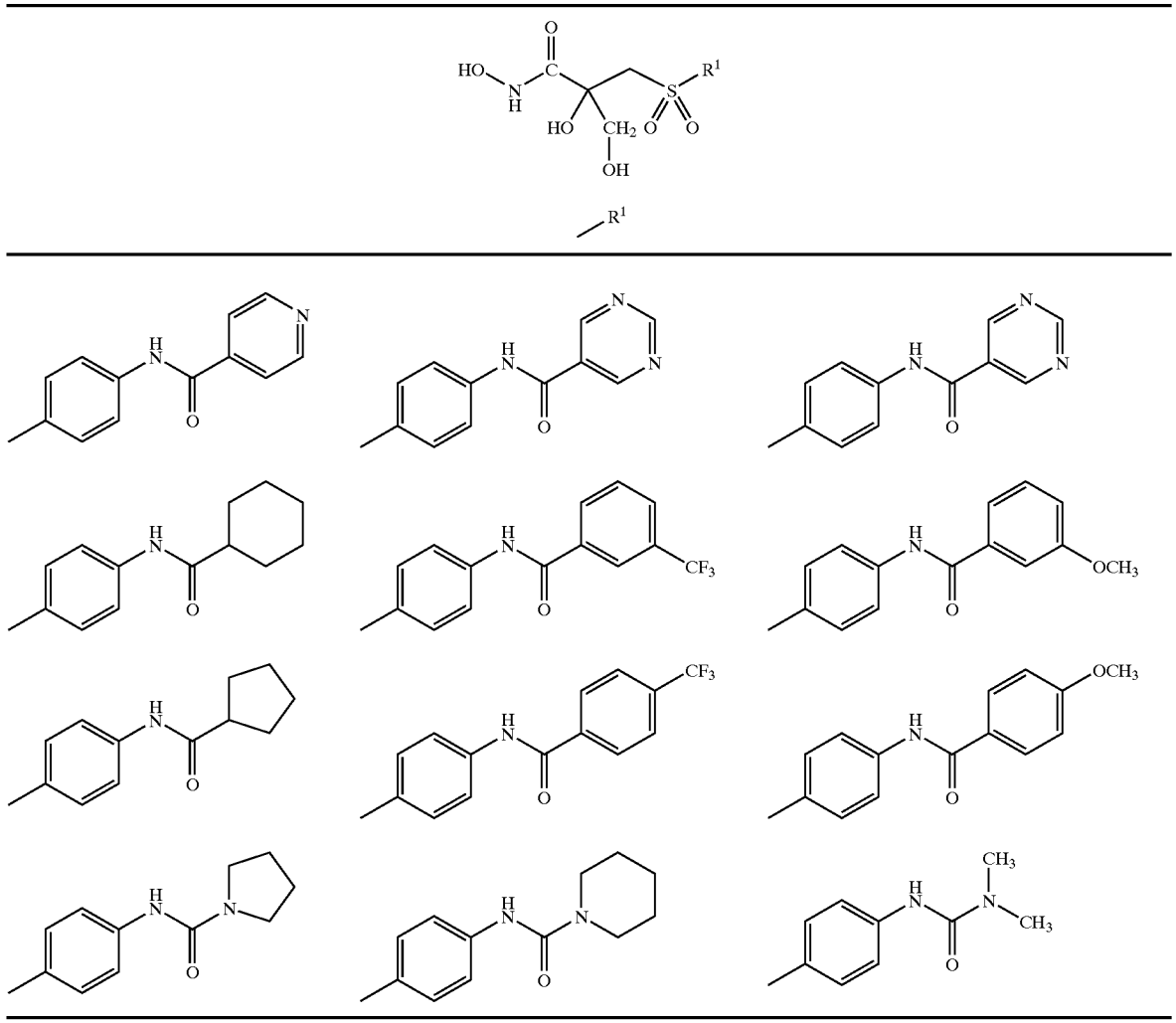
TABLE 13
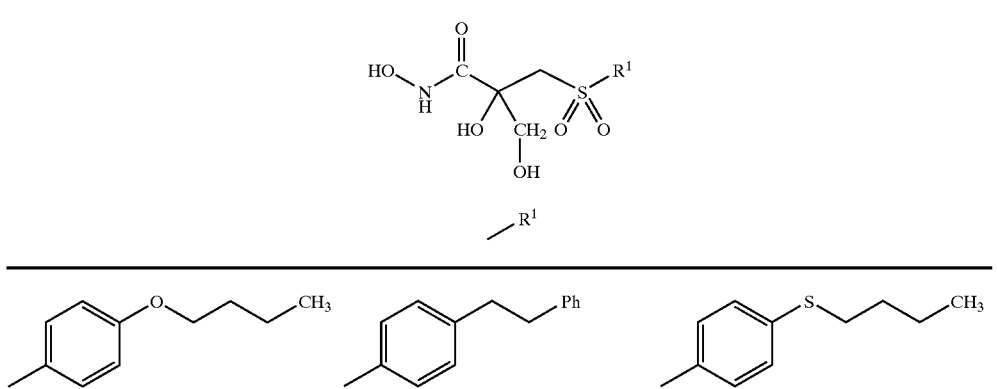

TABLE 13-continued
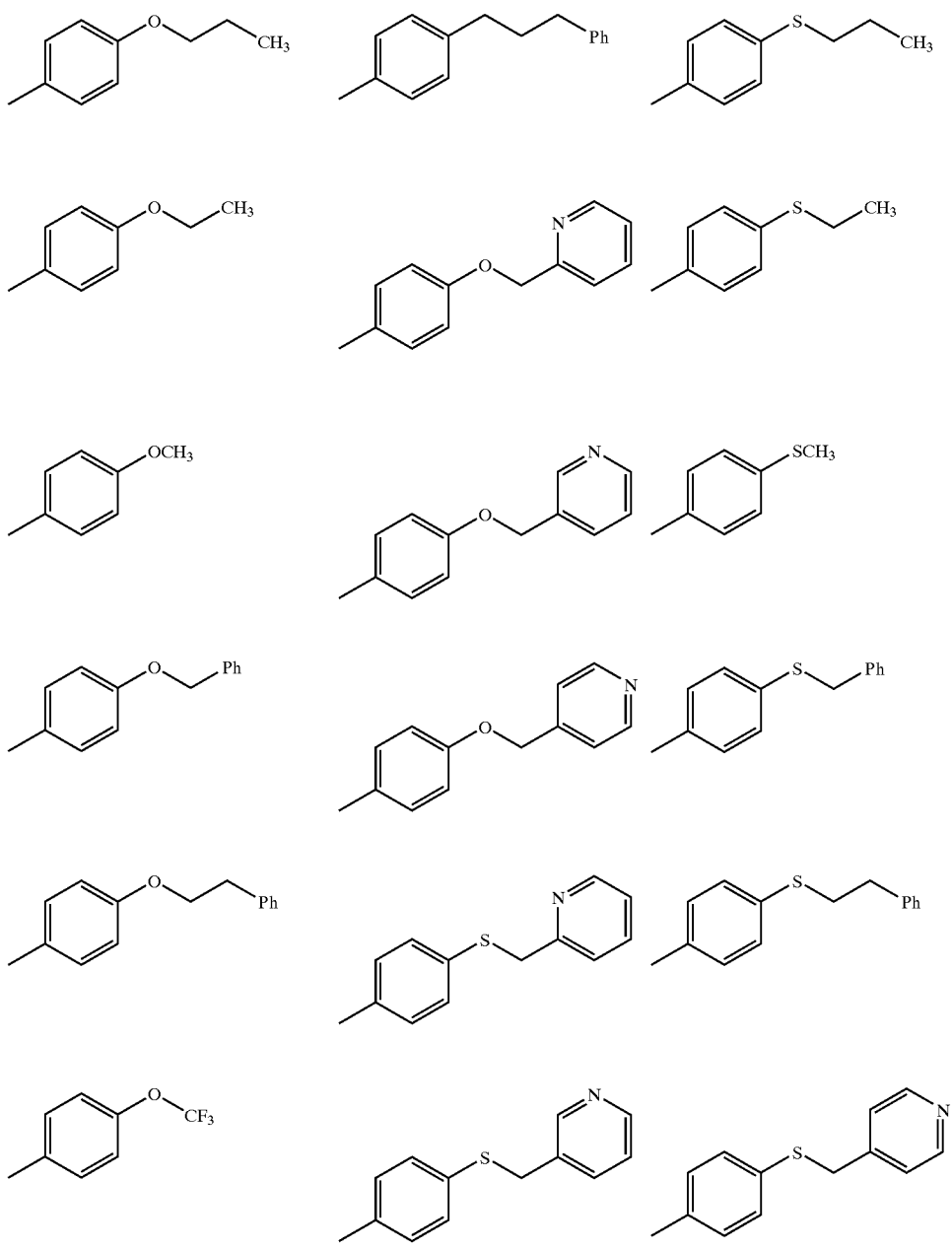

TABLE 14
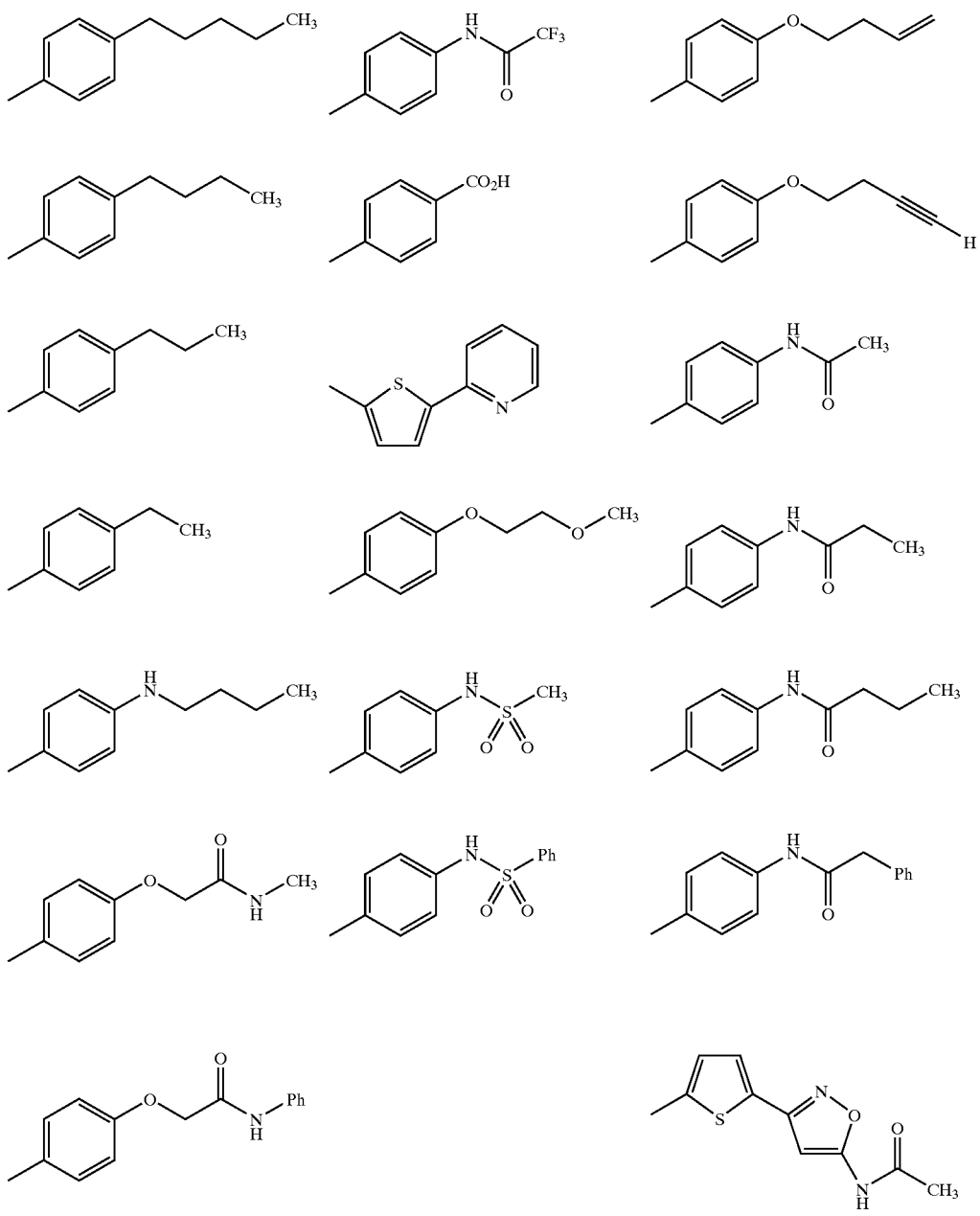

TABLE 15
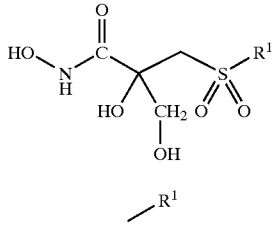
—R¹
| 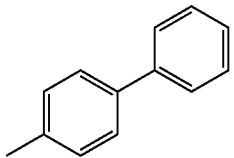 | 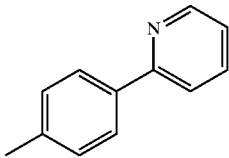 | 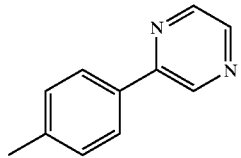 |
| 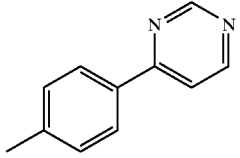 | 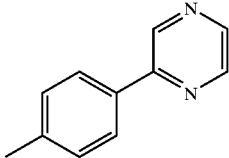 | 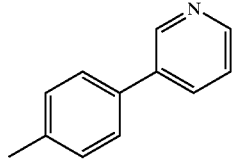 |
| 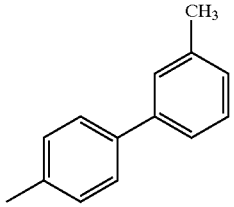 | 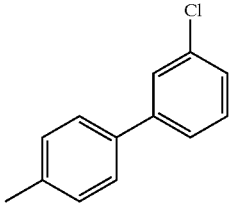 | 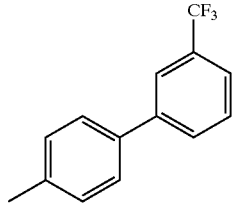 |
| 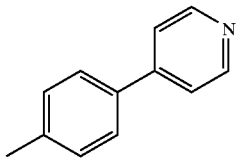 | 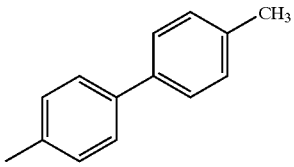 | 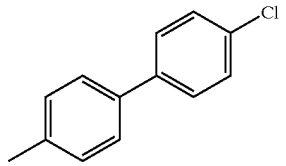 |
| 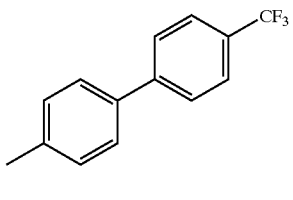 | 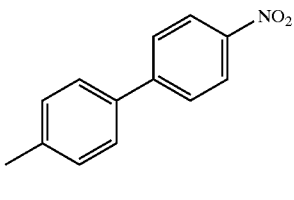 | 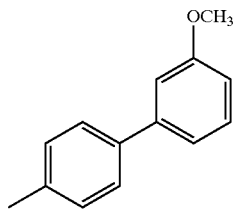 |
| 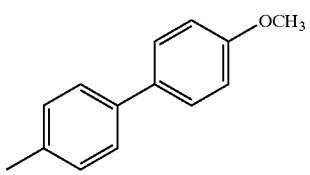 | 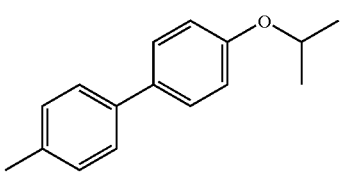 | 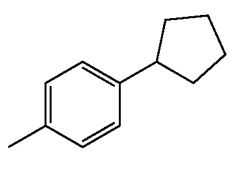 |
| 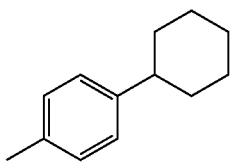 | 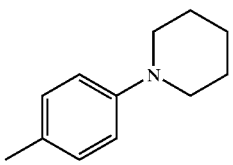 | 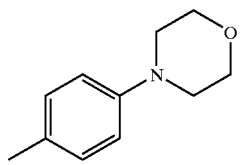 |

TABLE 16
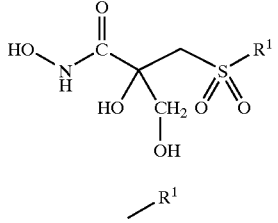
—R¹
| | | |
|---|---|---|
| 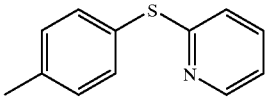 | 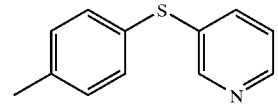 | 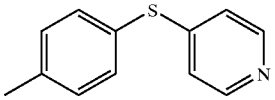 |
| 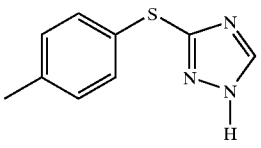 | 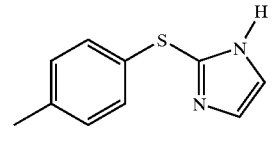 | 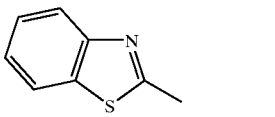 |
| 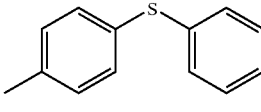 | | 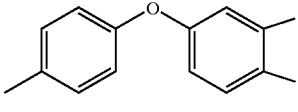 |
| 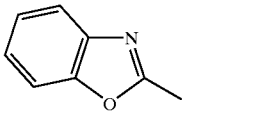 | 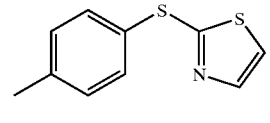 | 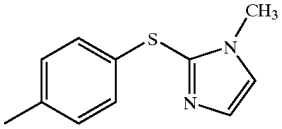 |
| 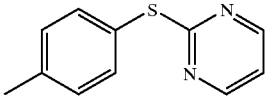 | 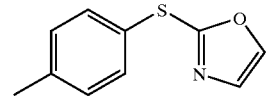 | 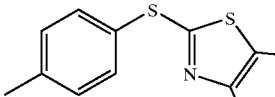 |
| 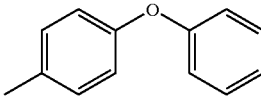 | | 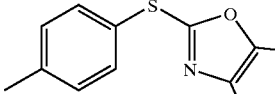 |
TABLE 17
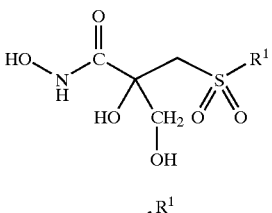
—R¹
| | | |
|---|---|---|
| 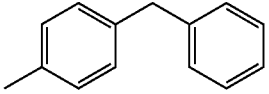 | 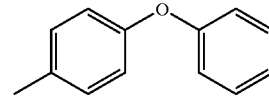 | 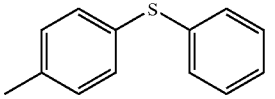 |

TABLE 17-continued
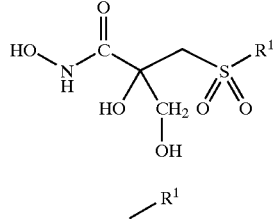
| 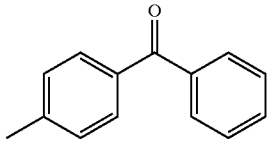 | 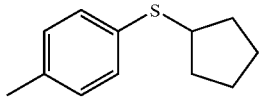 | 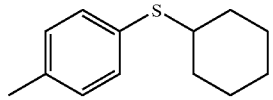 |
|---|---|---|
| 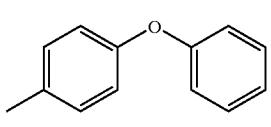 | 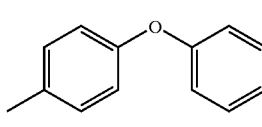 | 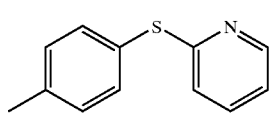 |
| 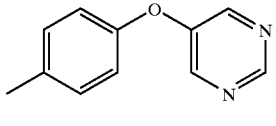 | 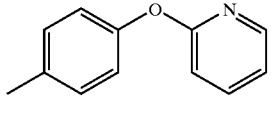 | 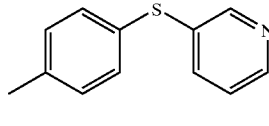 |
| 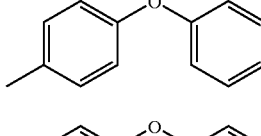 | 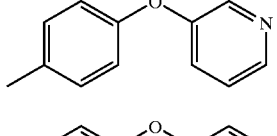 | 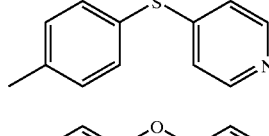 |
| 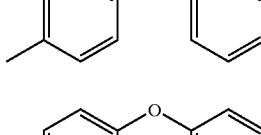 | 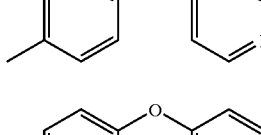 | 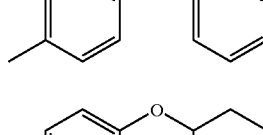 |
| 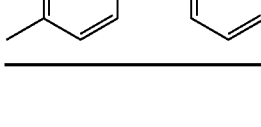 | 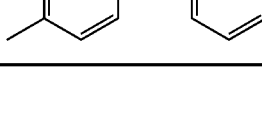 | 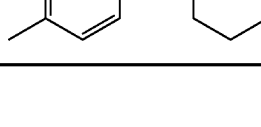 |
TABLE 18
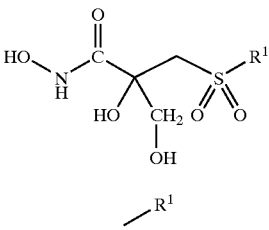
| 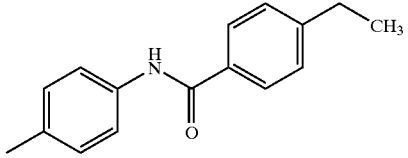 | 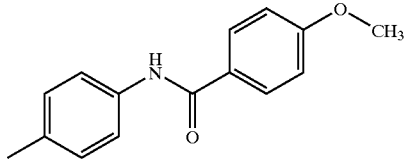 |
|---|---|

TABLE 18-continued
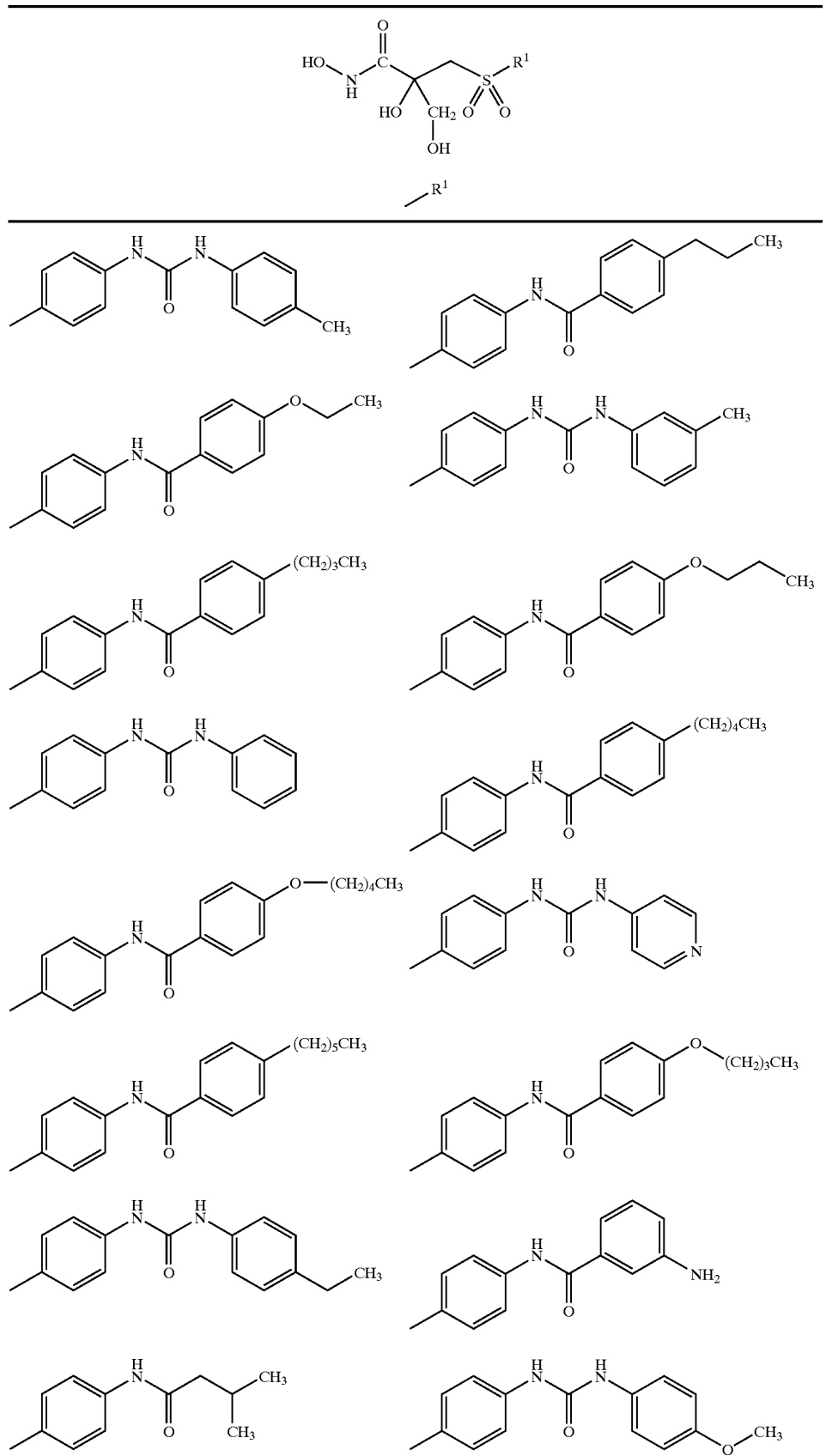

TABLE 18-continued
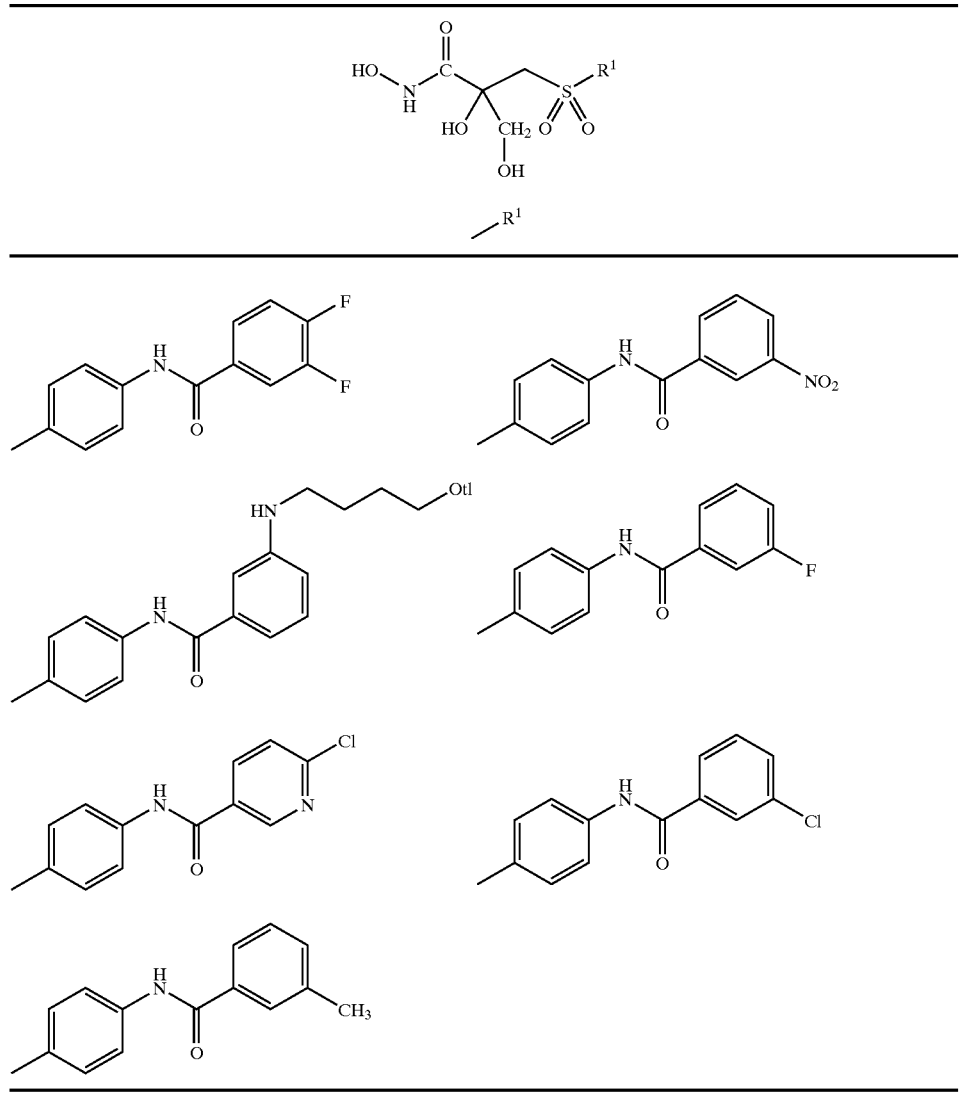
45
TABLE 19
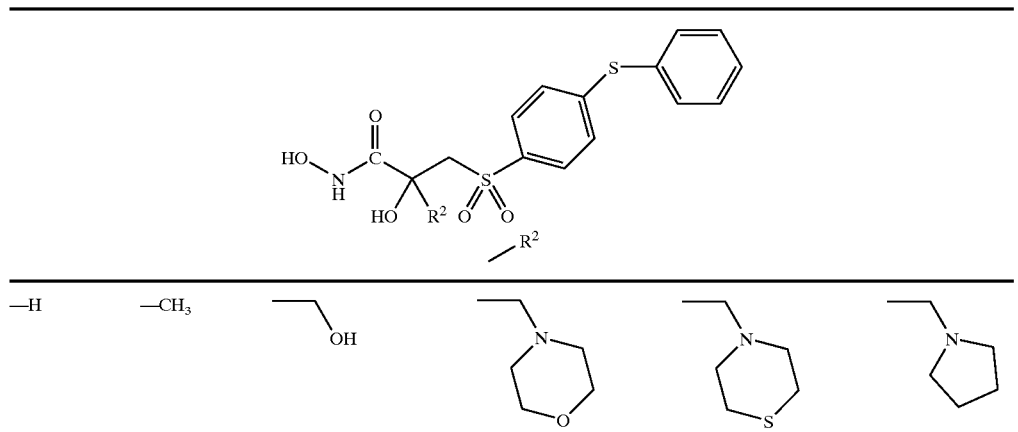

TABLE 19-continued
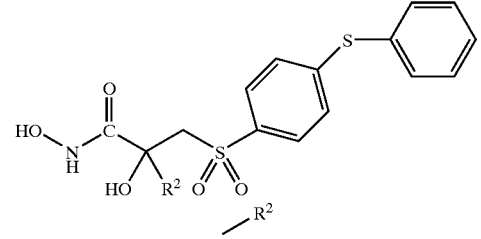
TABLE 20
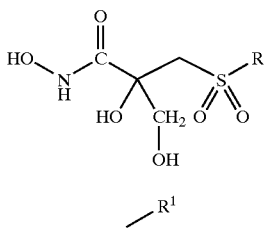

TABLE 20-continued
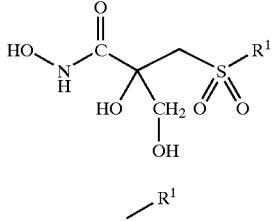
| 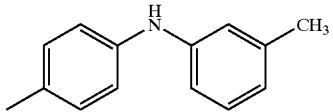 | 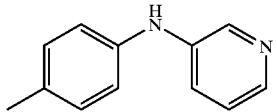 | 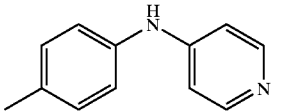 |
| 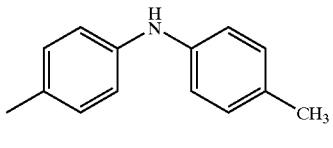 | 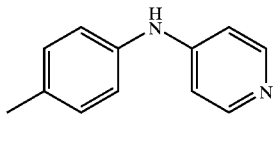 | 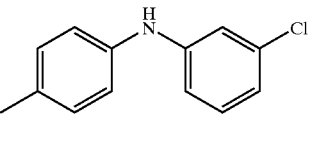 |
| 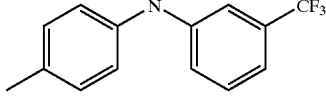 | 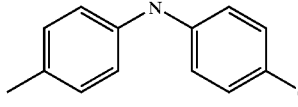 | 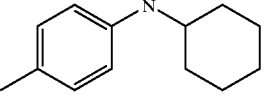 |
TABLE 21
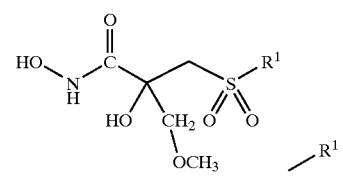
| 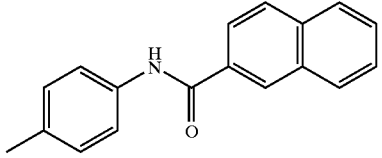 | 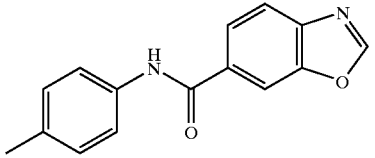 | 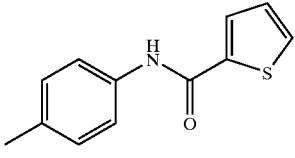 |
| 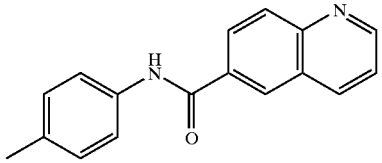 | 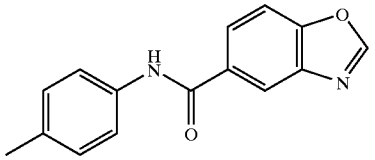 | 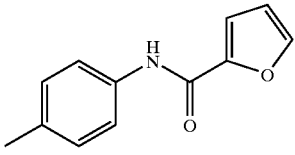 |
| 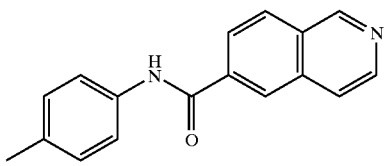 | 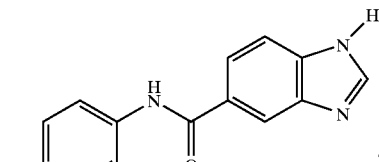 | 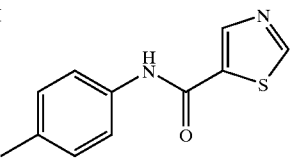 |

TABLE 21-continued
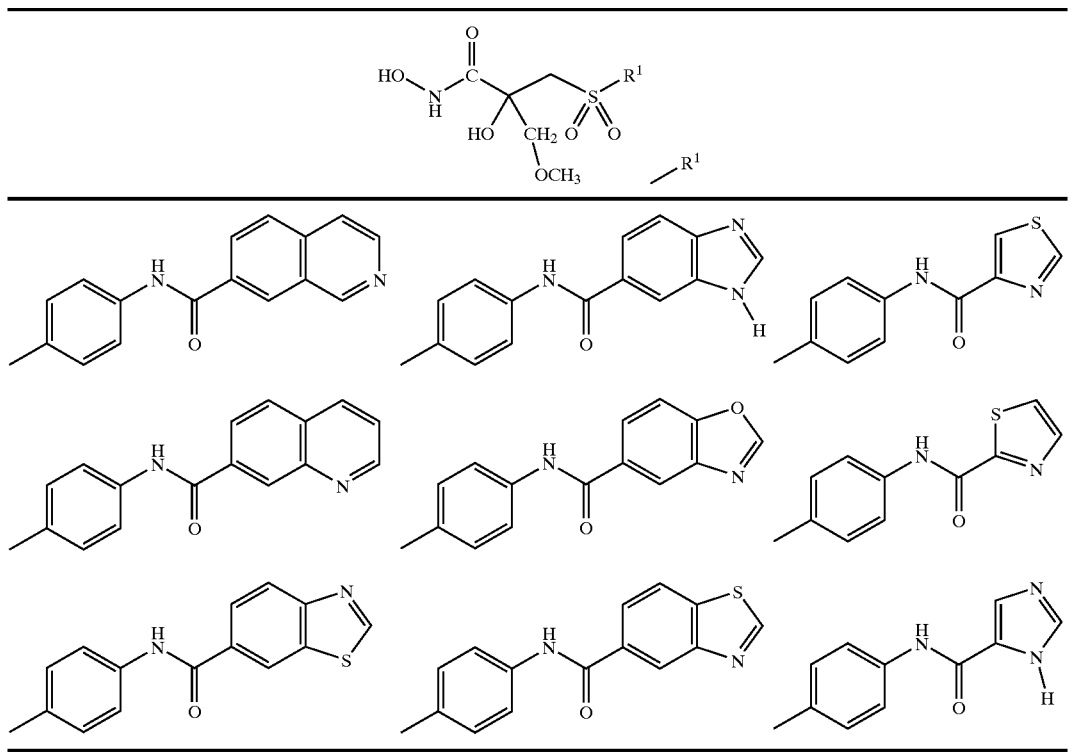
TABLE 22
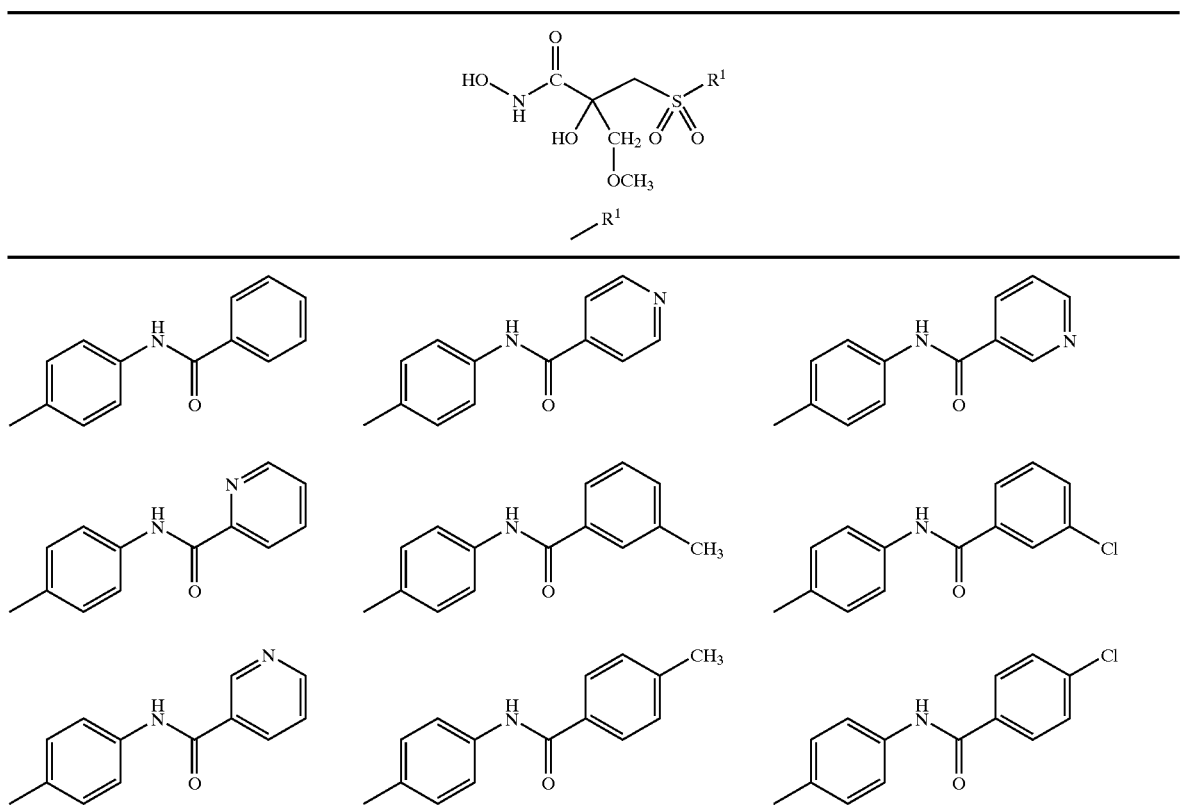

TABLE 22-continued
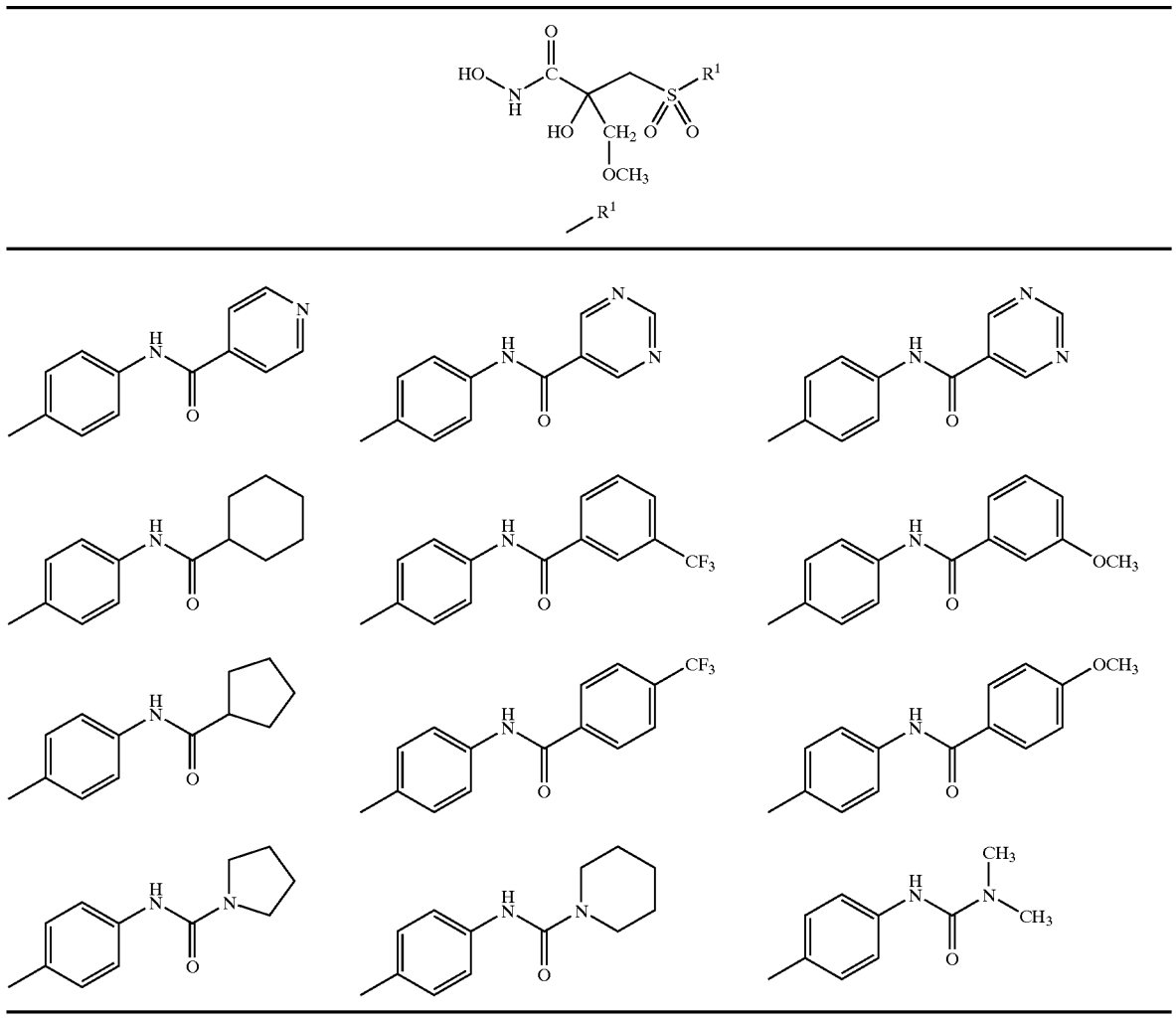
TABLE 23
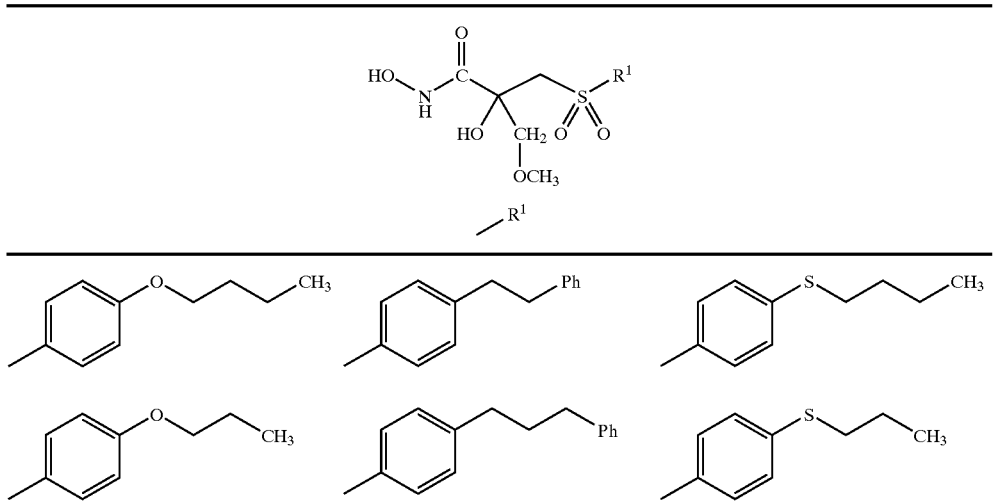

TABLE 23-continued
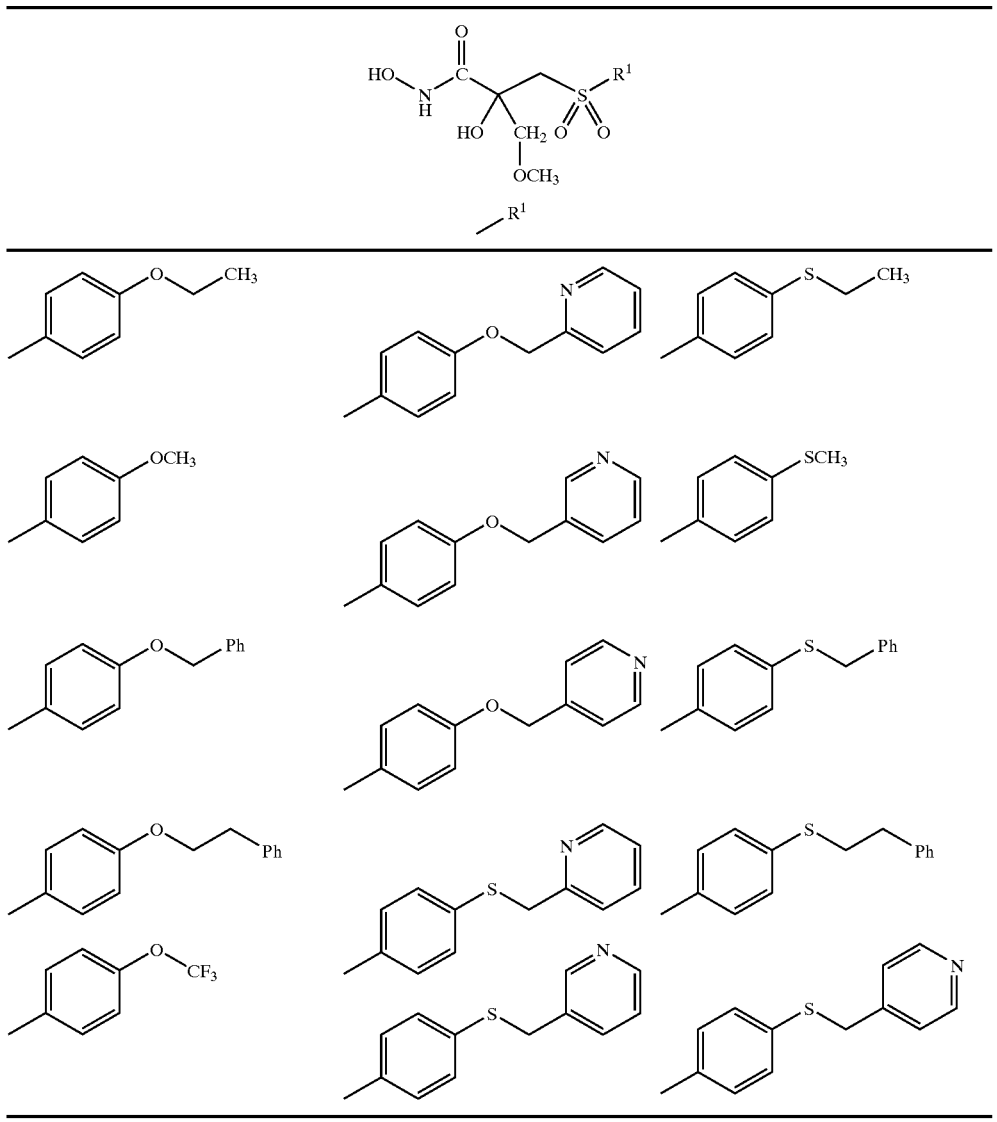
TABLE 24
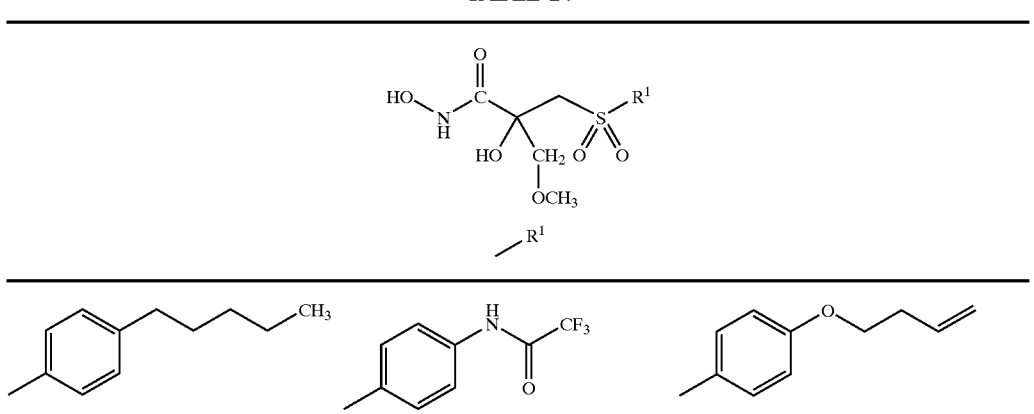

TABLE 24-continued
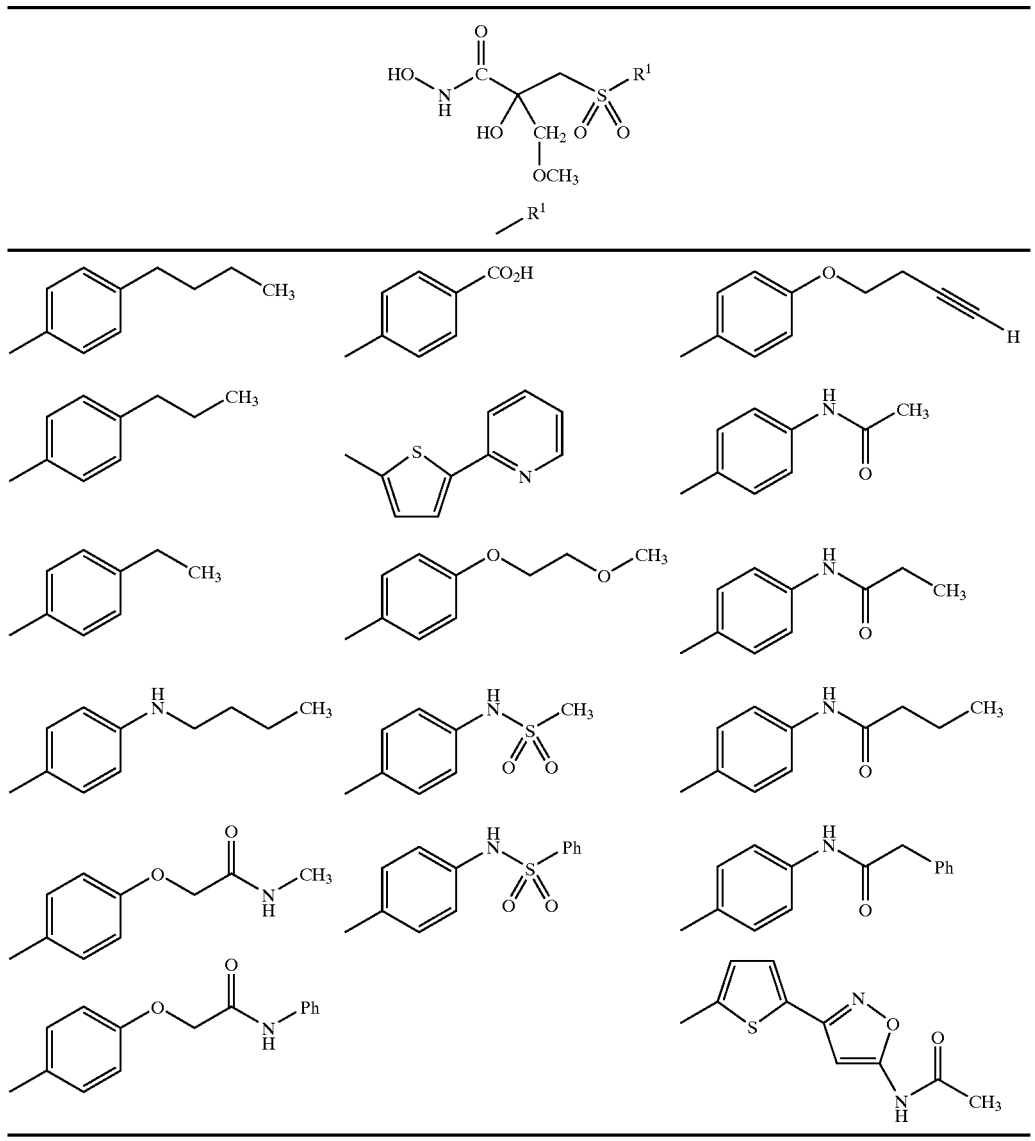
TABLE 25
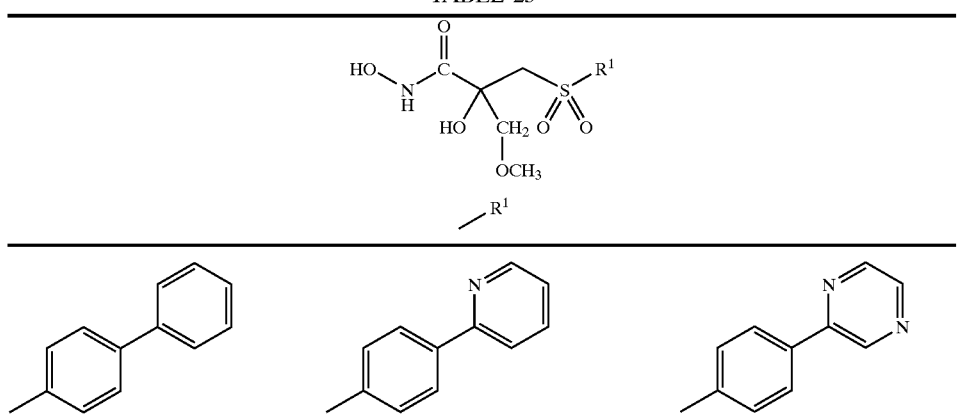

TABLE 25-continued
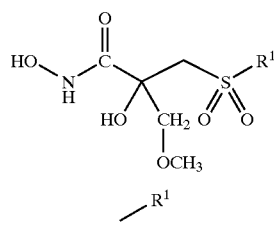
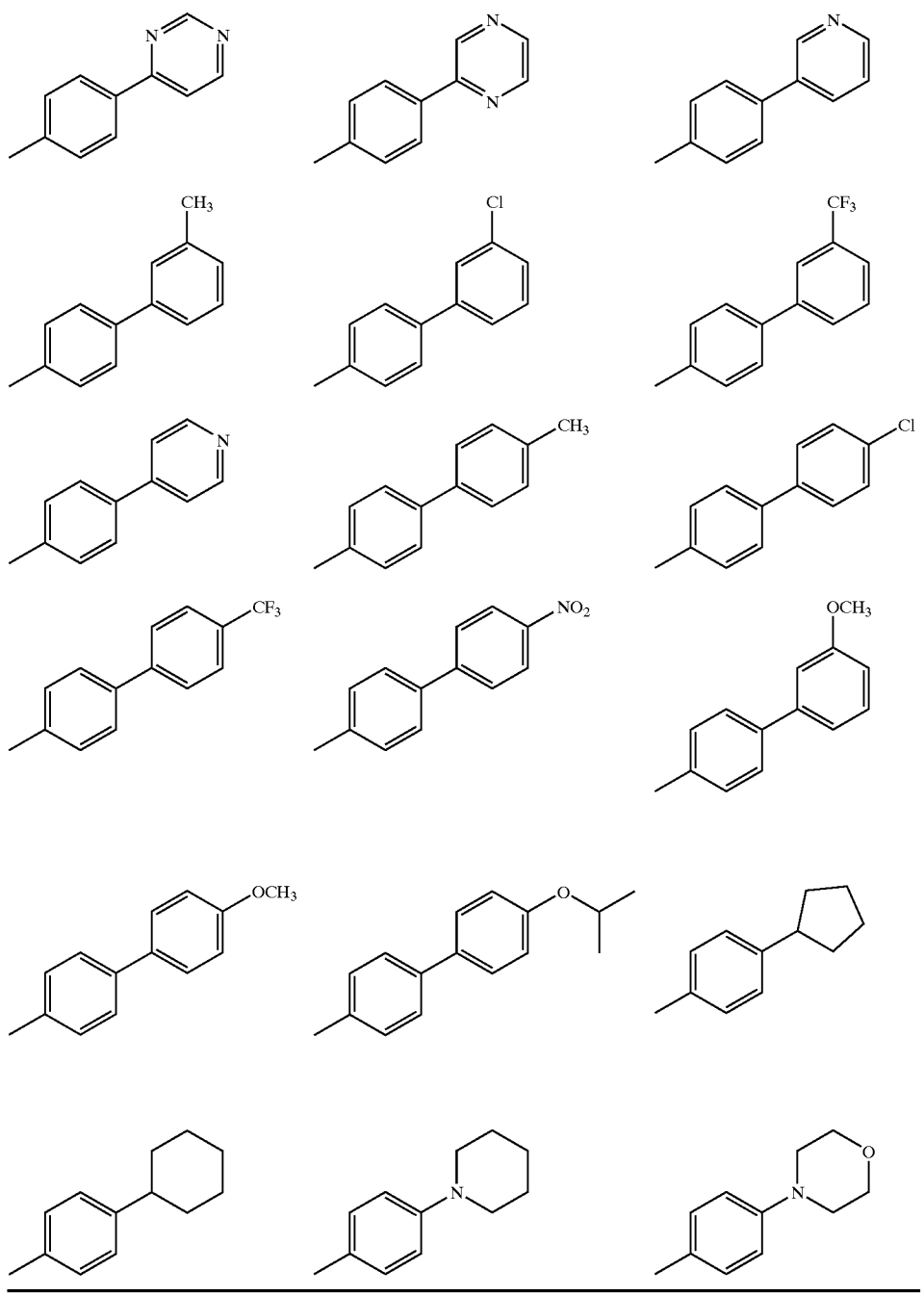

TABLE 26

(structure shown with HO-NH-C(=O)-C(OH)(CH₂-OCH₃)-CH₂-S(=O)(=O)-R¹)

—R¹

TABLE 27-continued
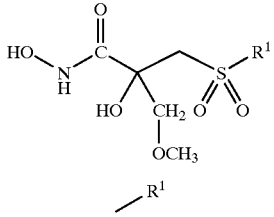
| 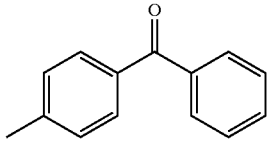 | 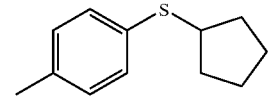 | 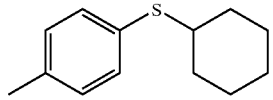 |
|---|---|---|
| 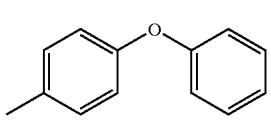 | 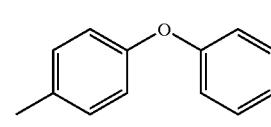 | 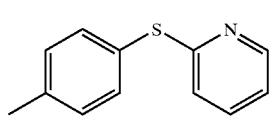 |
| 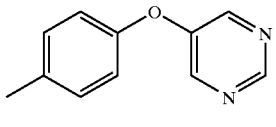 | 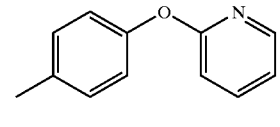 | 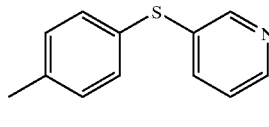 |
| 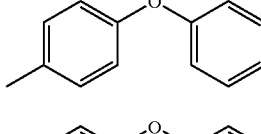 | 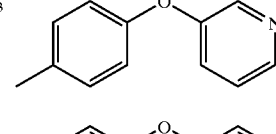 | 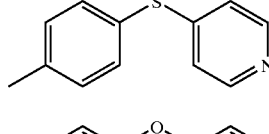 |
| 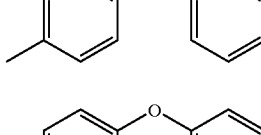 | 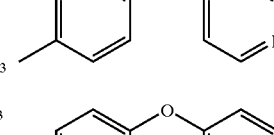 | 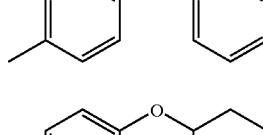 |
| 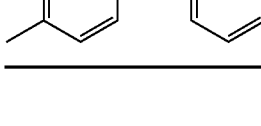 | 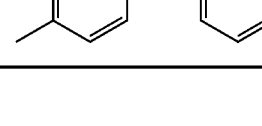 | 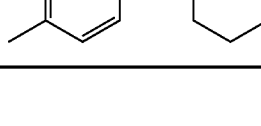 |
TABLE 28
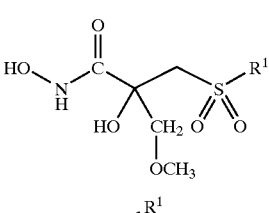
| 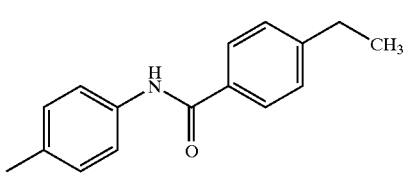 | 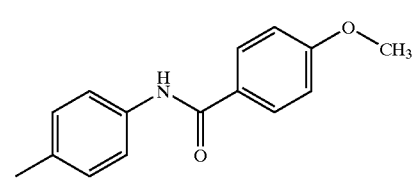 |
|---|---|

TABLE 28-continued
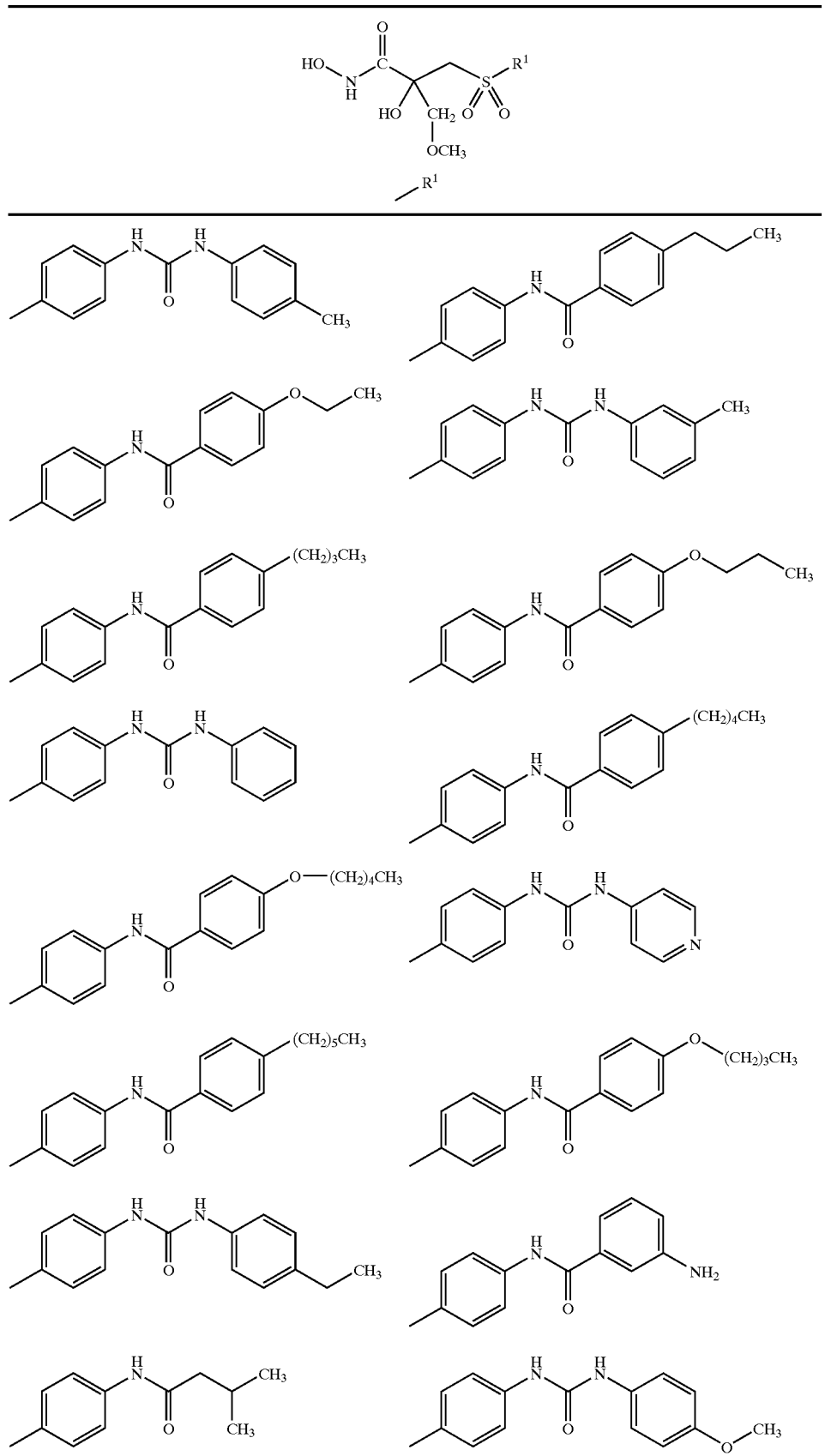

TABLE 28-continued
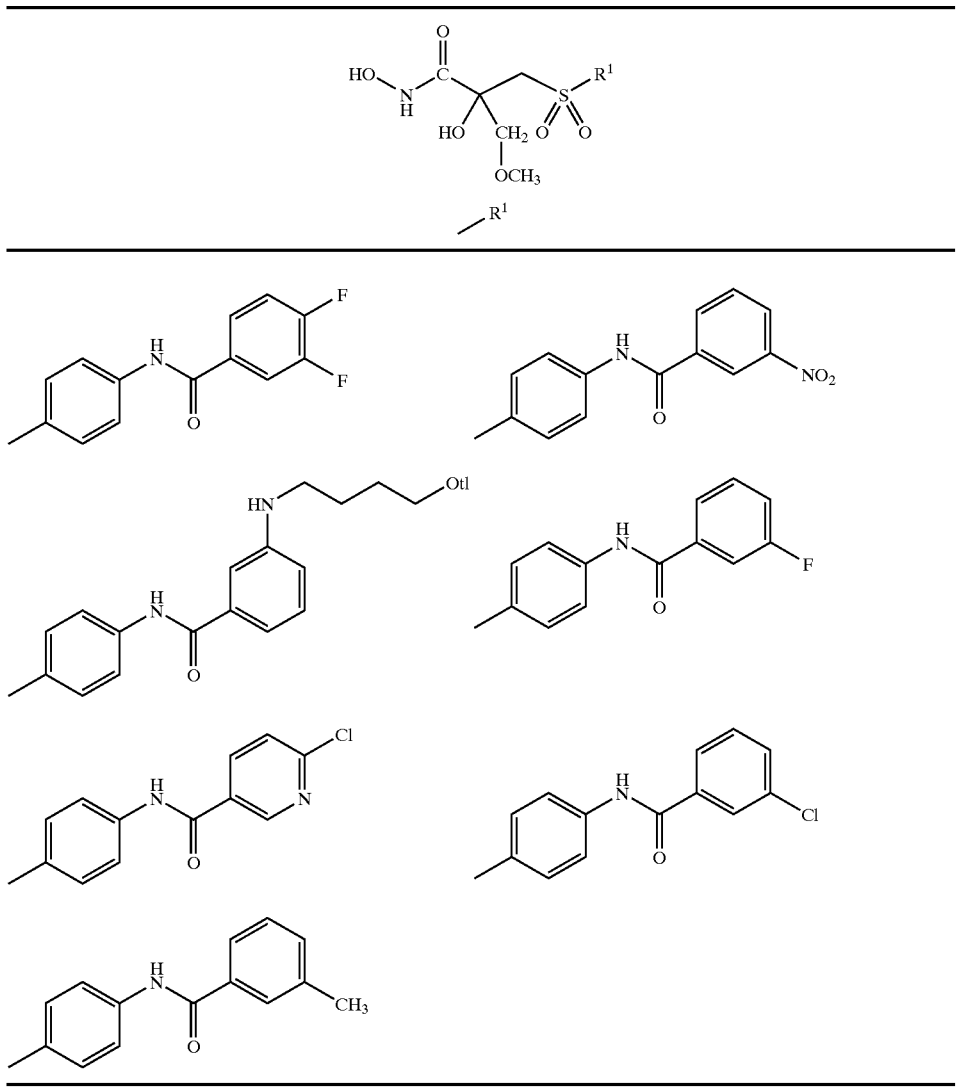
TABLE 29
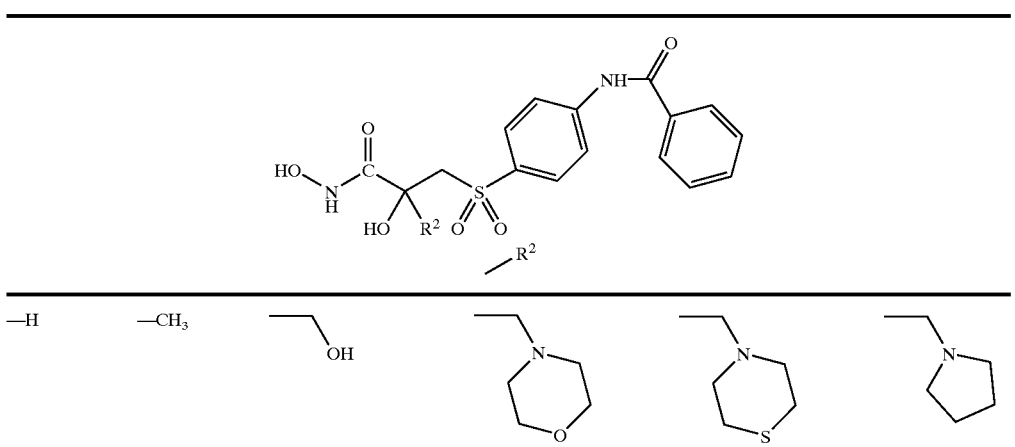

TABLE 29-continued
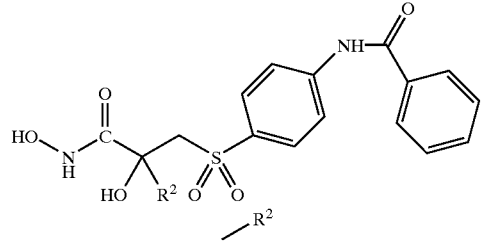
TABLE 30
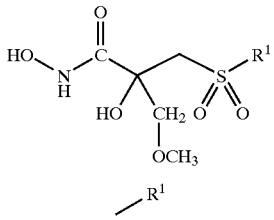

TABLE 30-continued
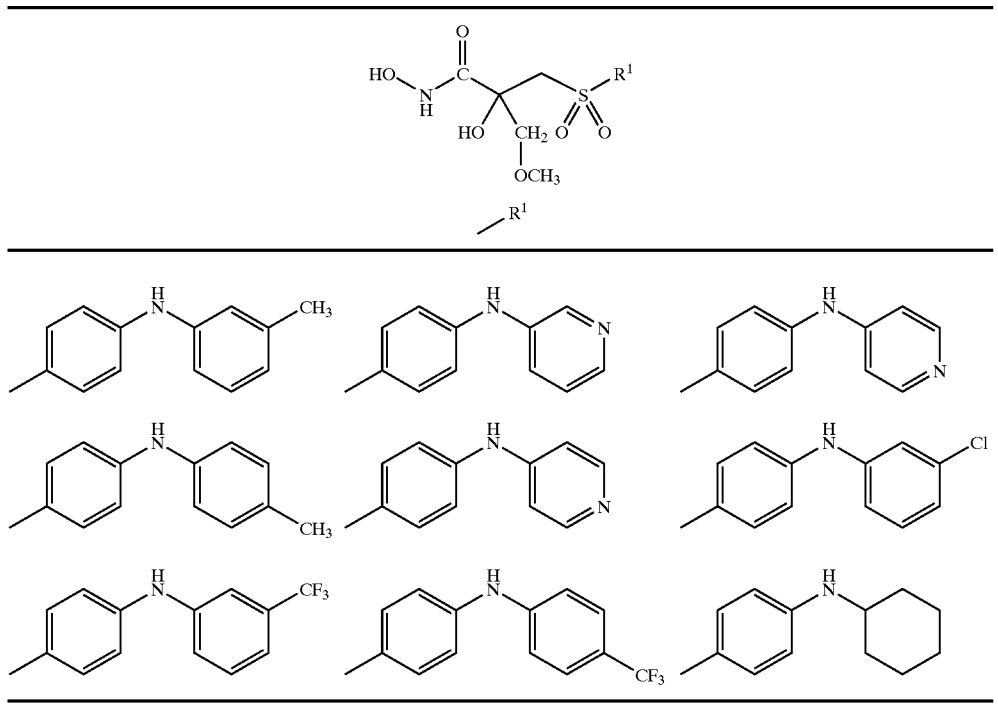
TABLE 31
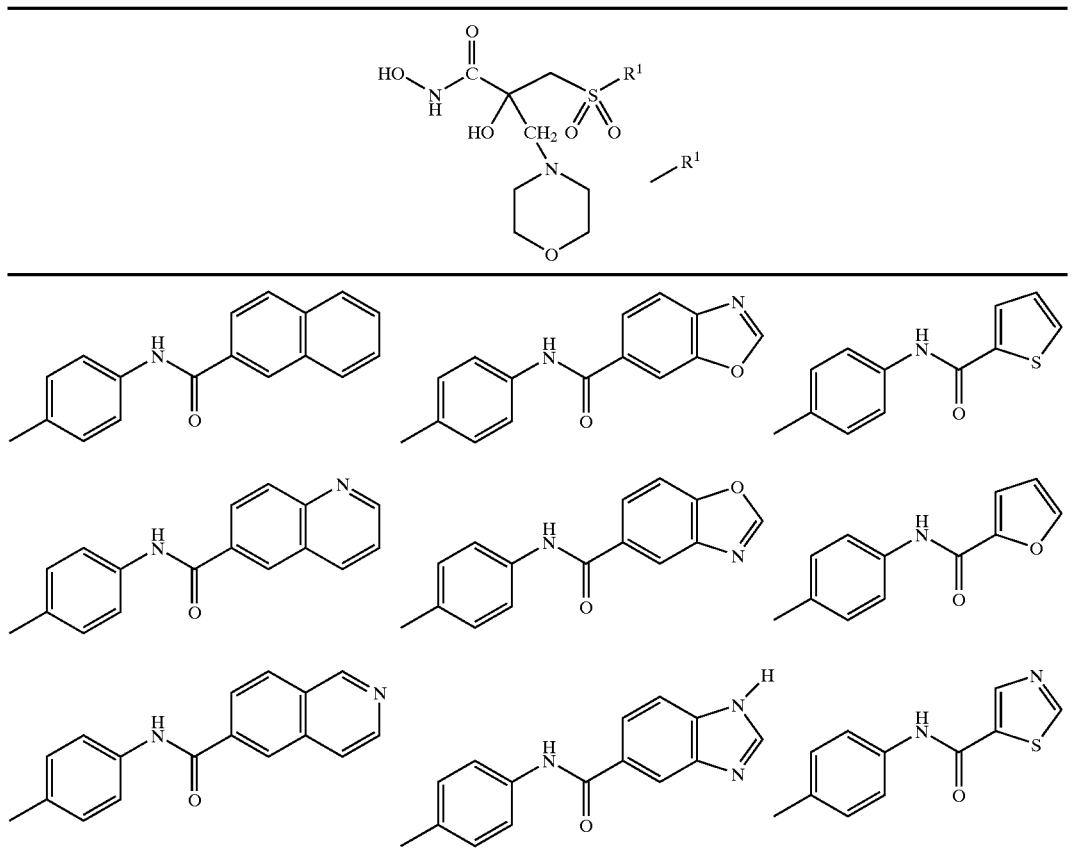

TABLE 31-continued
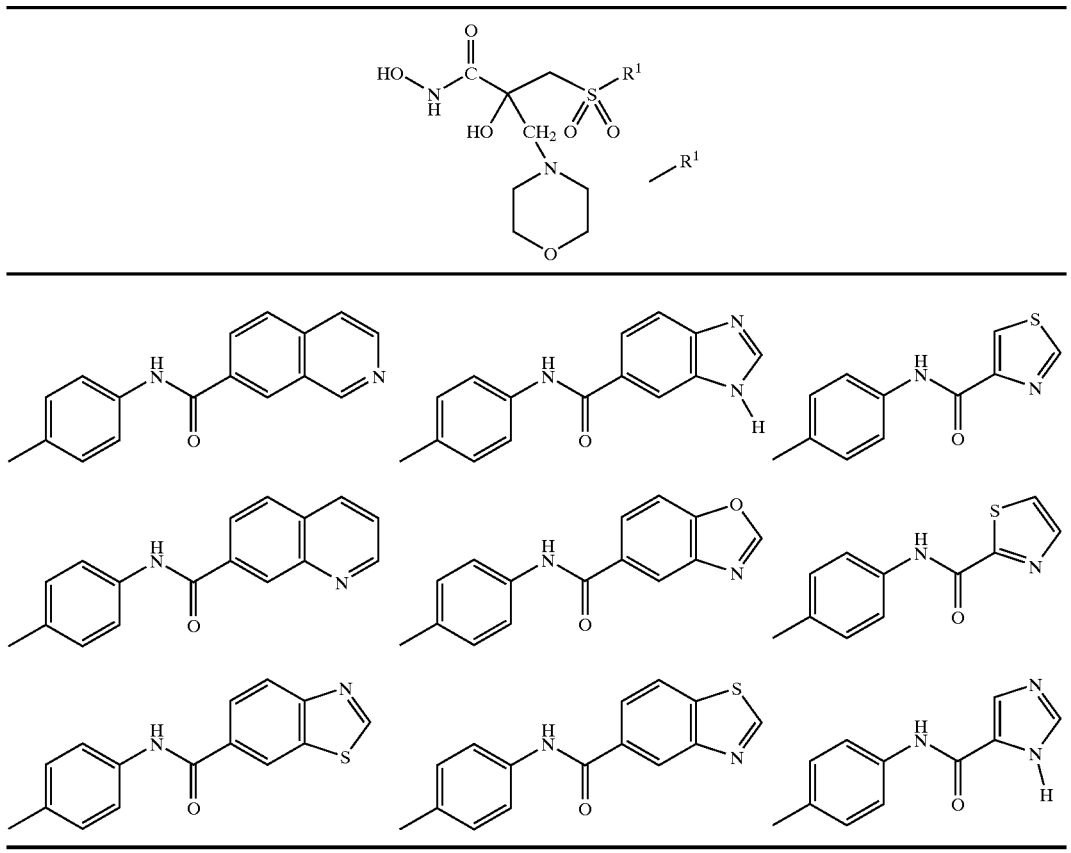
TABLE 32
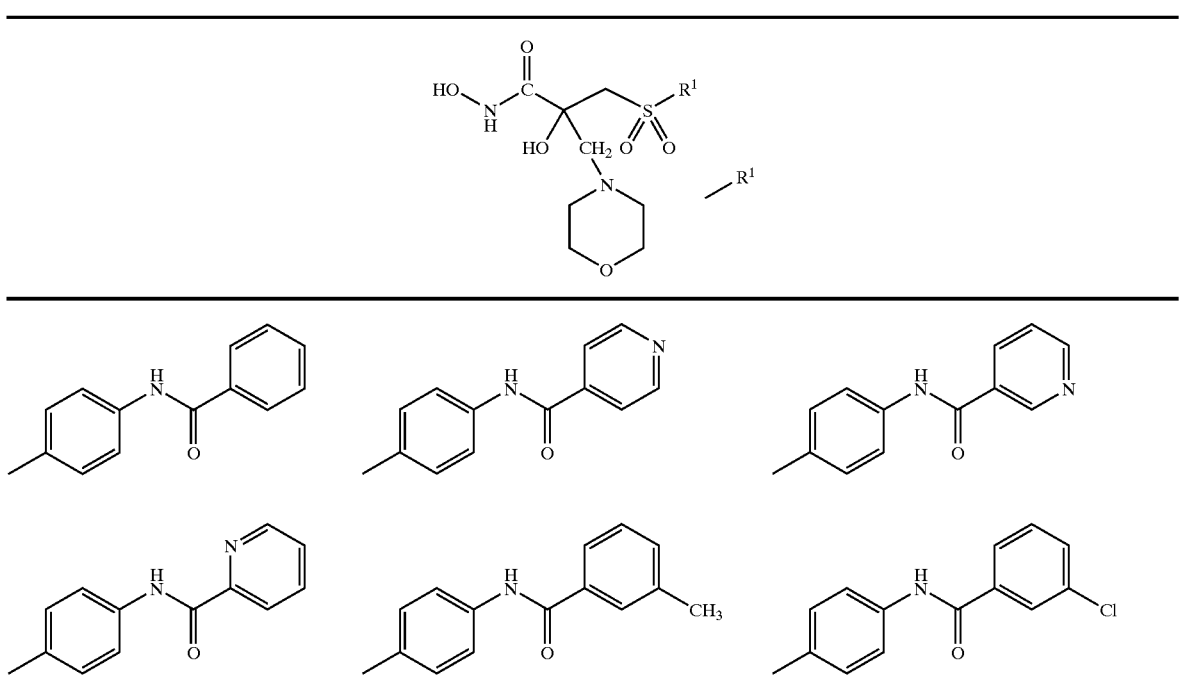

TABLE 32-continued
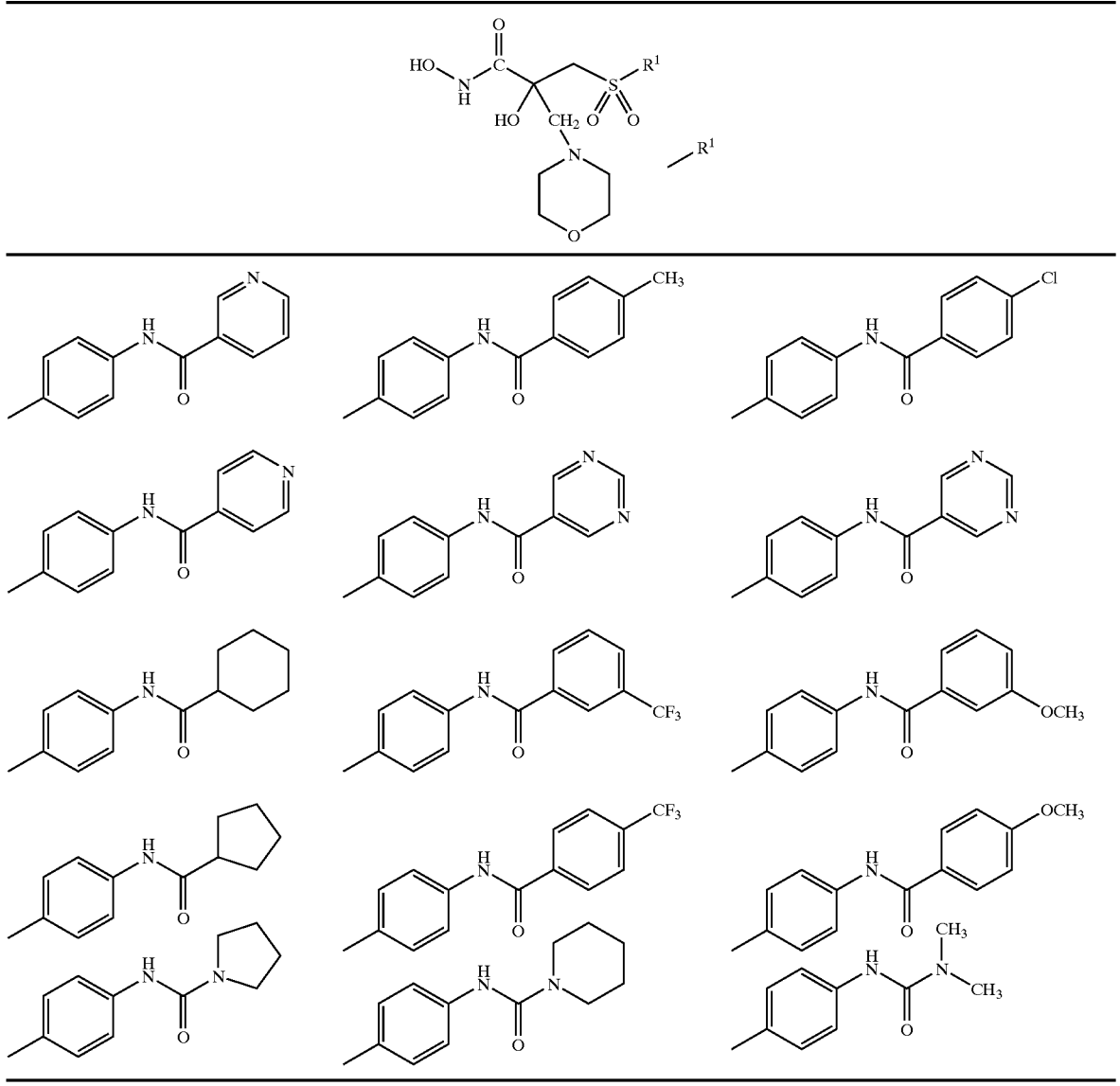
TABLE 33
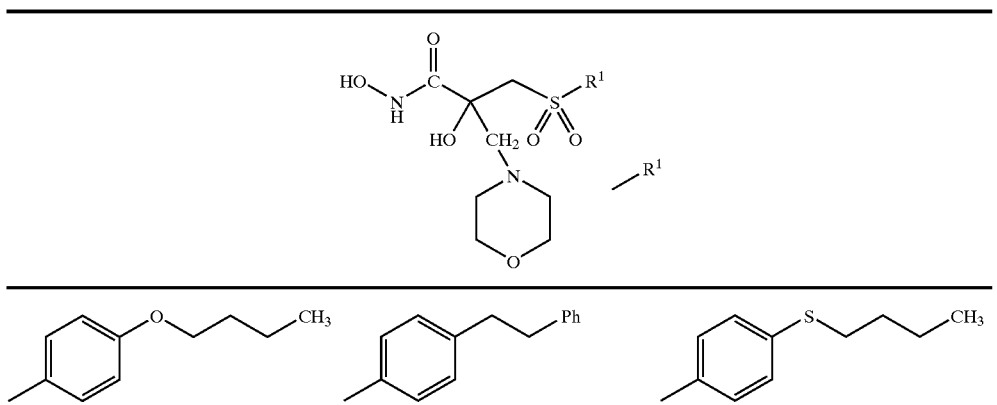

TABLE 33-continued
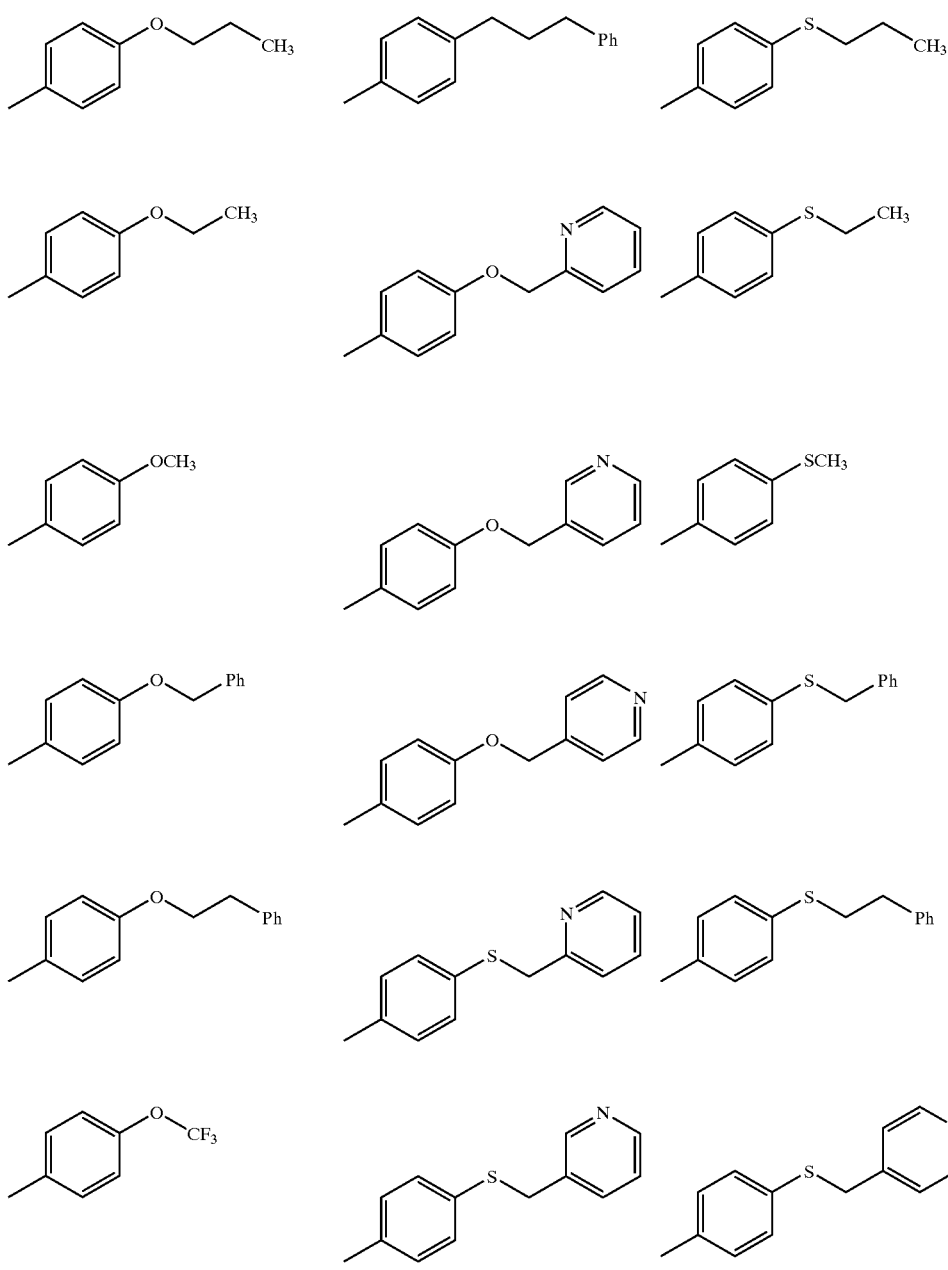

TABLE 34
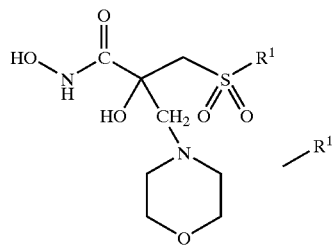
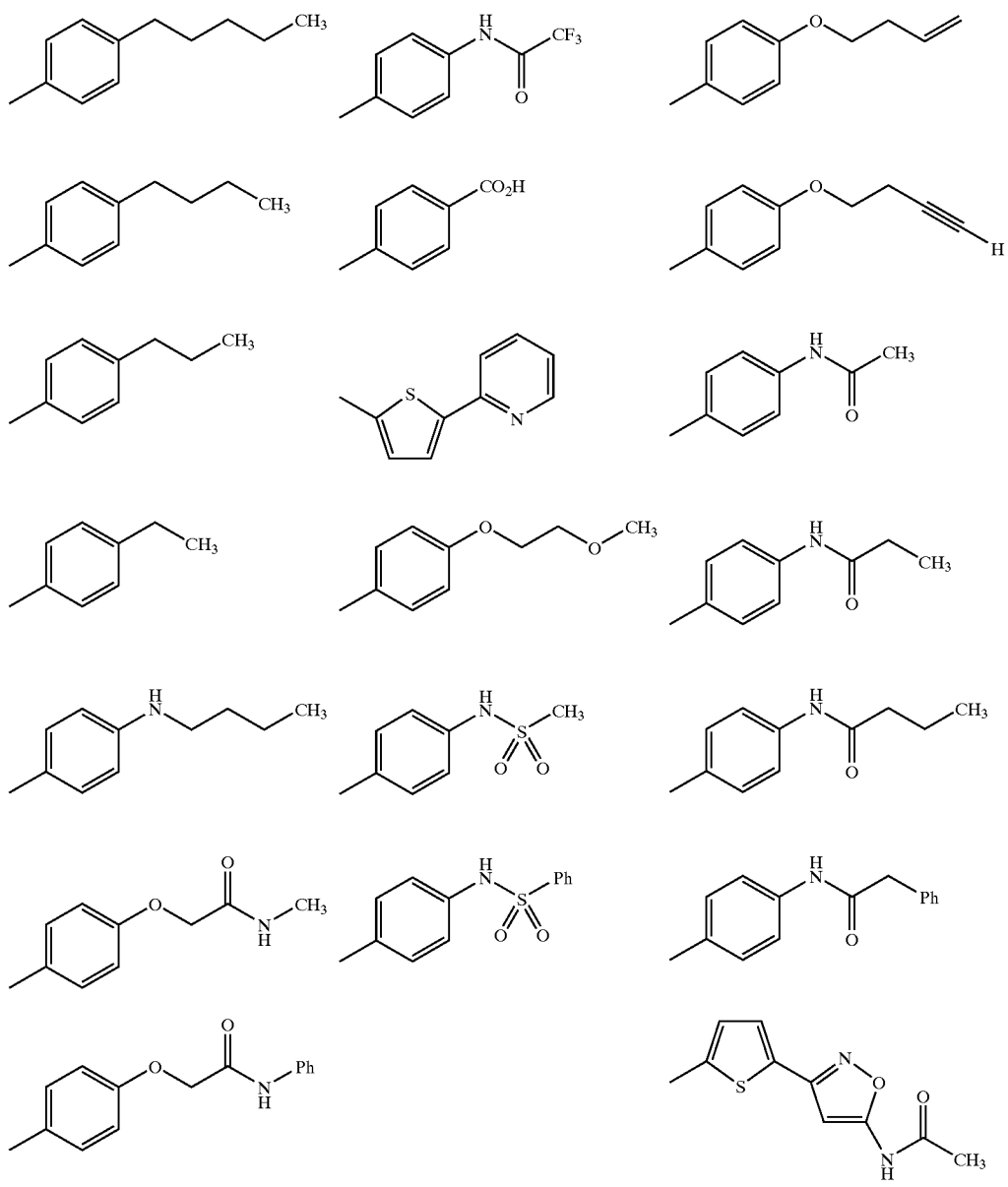

TABLE 35

TABLE 36

(Structure: hydroxamic acid with morpholine and sulfonyl-R¹ substituents)

R¹ substituents shown.

TABLE 37

(Structure: hydroxamic acid with morpholine and sulfonyl-R¹ substituents)

R¹ substituents shown.

TABLE 37-continued
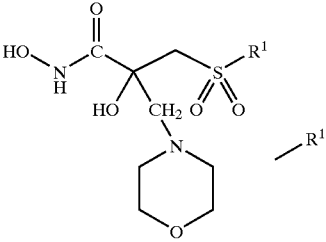
| 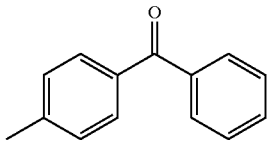 | 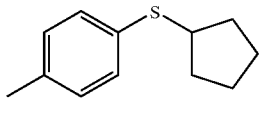 | 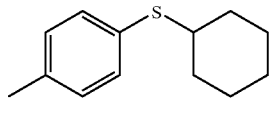 |
|---|---|---|
| 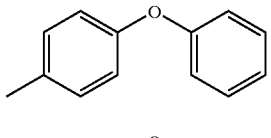 | 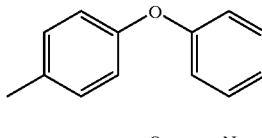 | 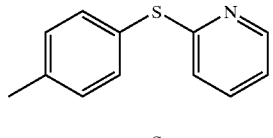 |
| 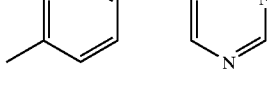 | 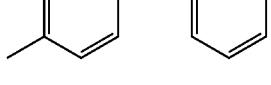 | 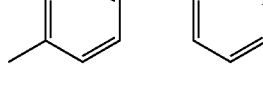 |
| 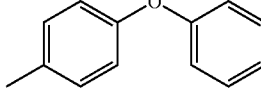 | 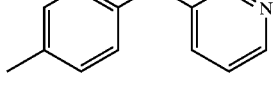 | 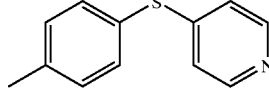 |
| 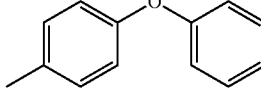 | 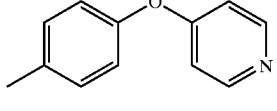 | 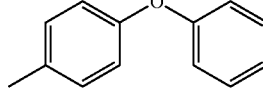 |
| 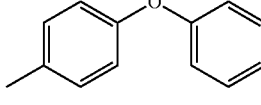 | 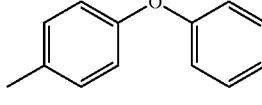 | 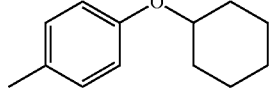 |
TABLE 38
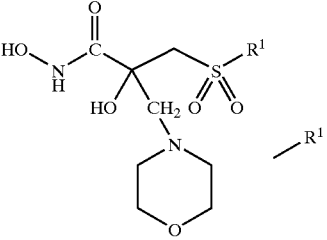
| 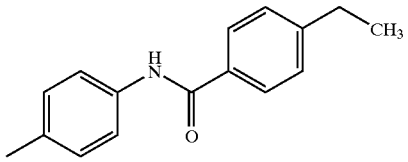 | 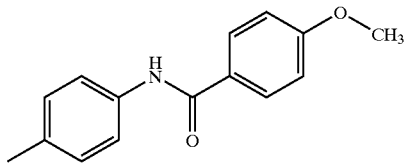 |
|---|---|

TABLE 38-continued
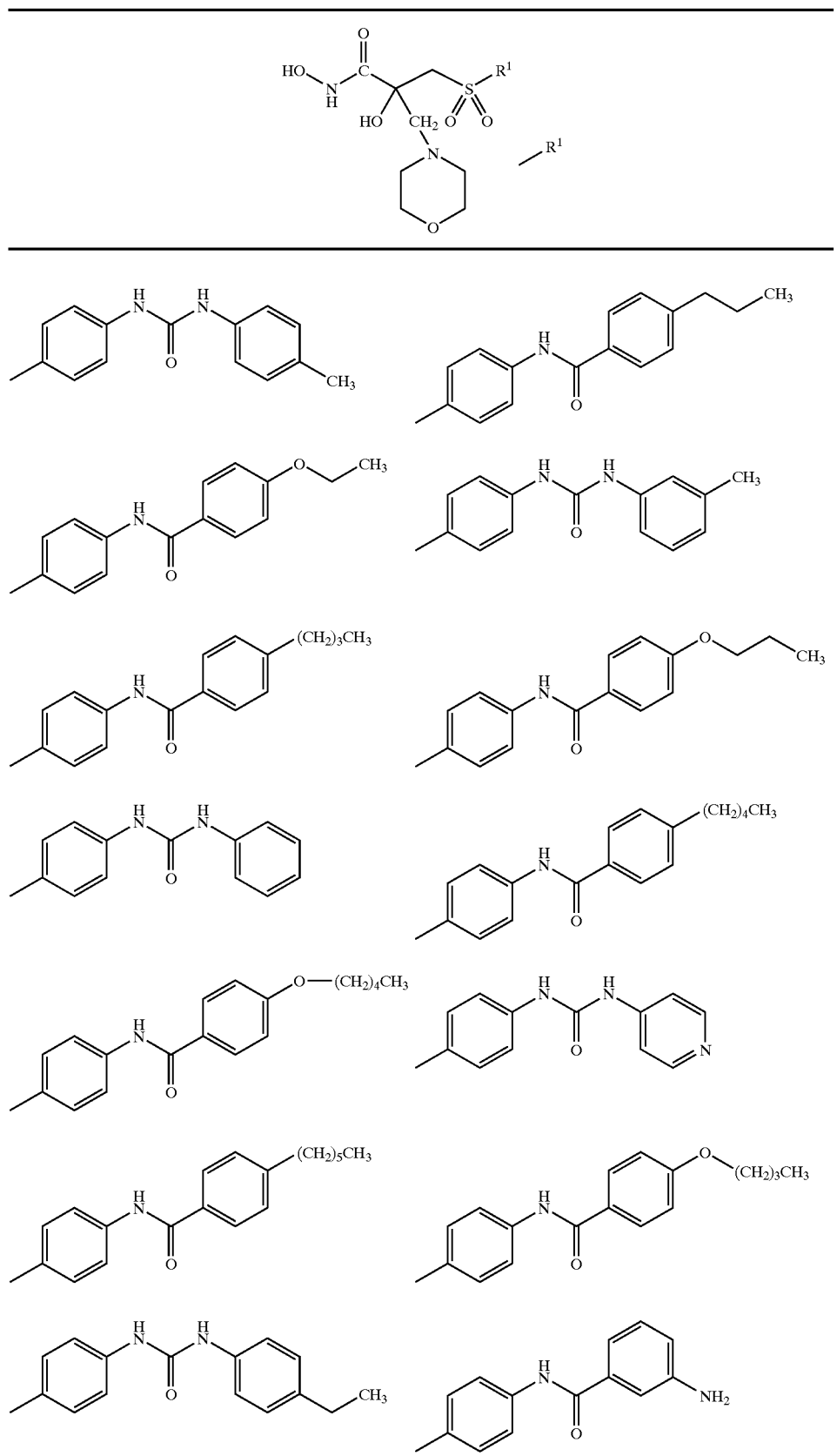

TABLE 38-continued
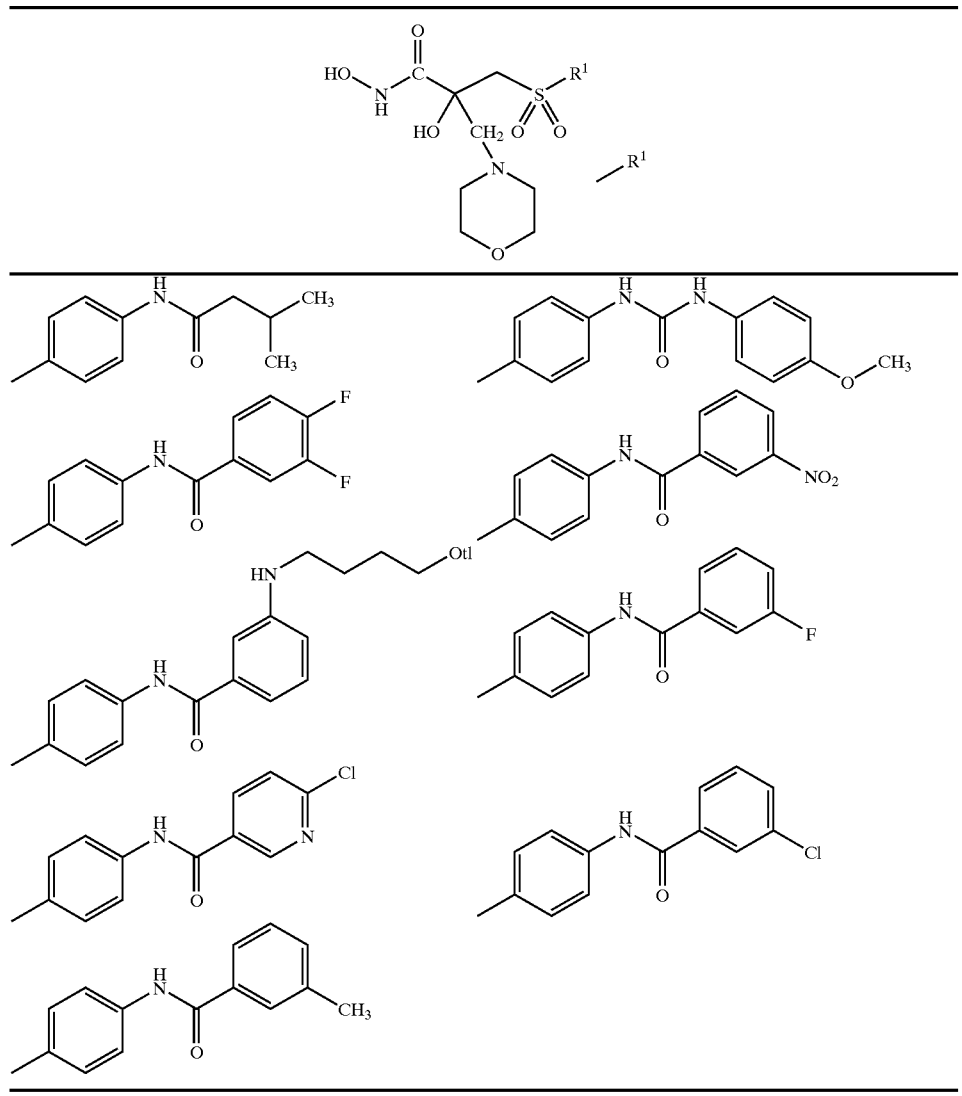
TABLE 39
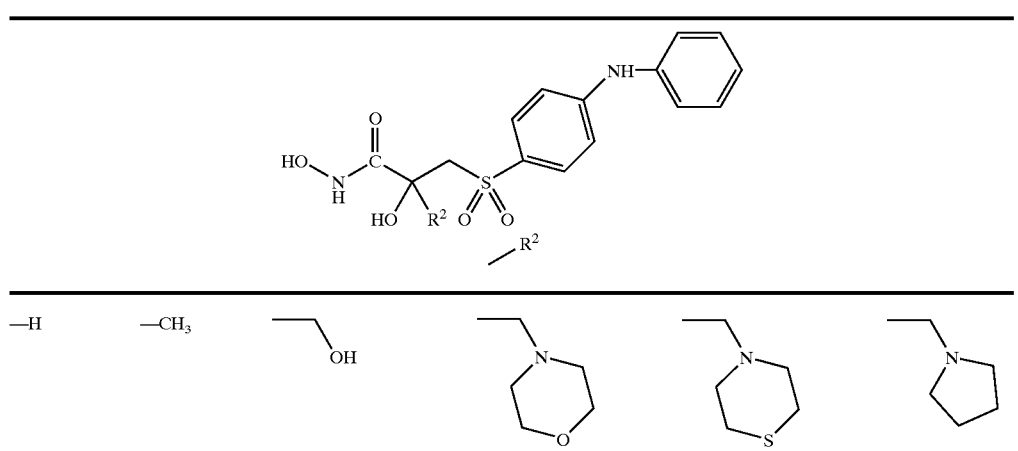

TABLE 39-continued

[Chemical structure: hydroxamic acid derivative with sulfonyl-phenyl-NH-phenyl group, substituted with R² groups]

TABLE 40

[Chemical structure: hydroxamic acid derivative with sulfonyl-R¹ and morpholinomethyl substituents]

TABLE 40-continued
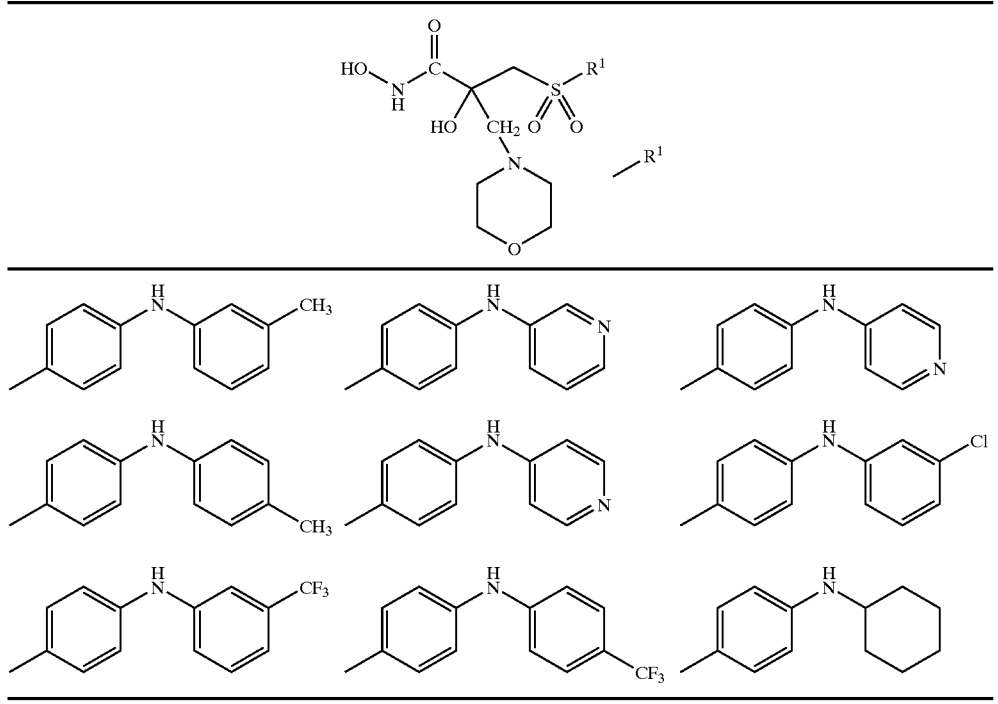
TABLE 41
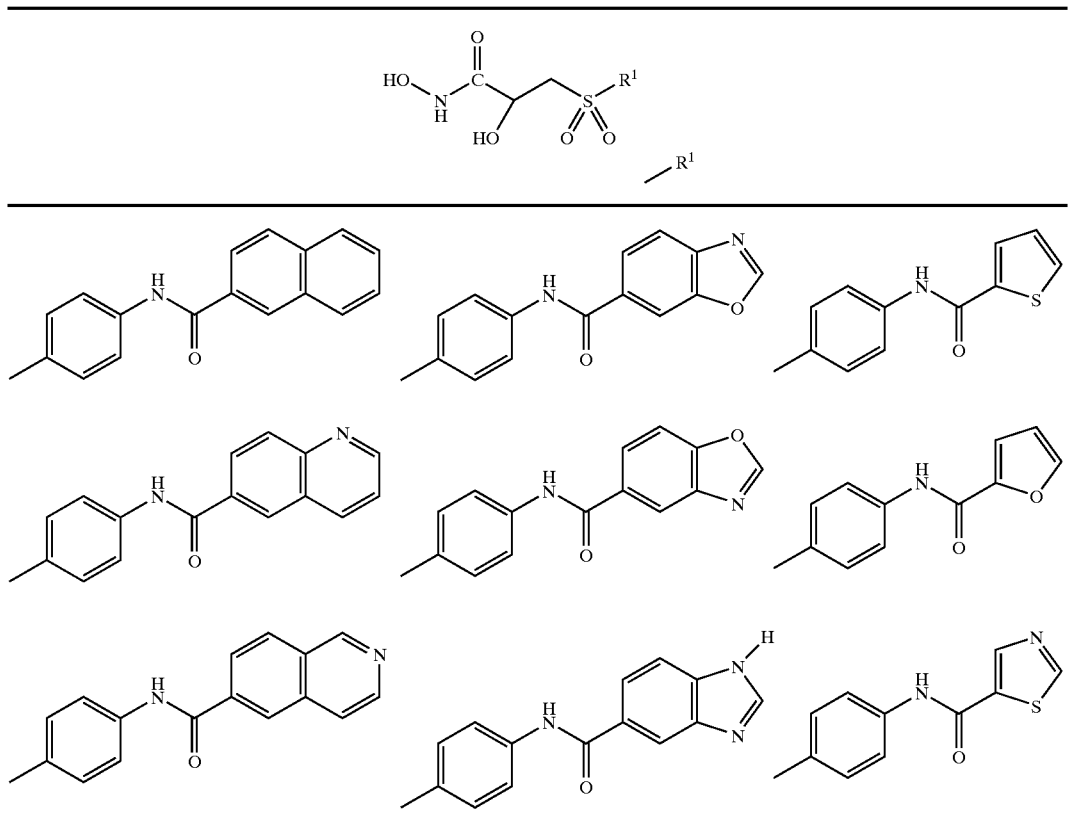

TABLE 41-continued
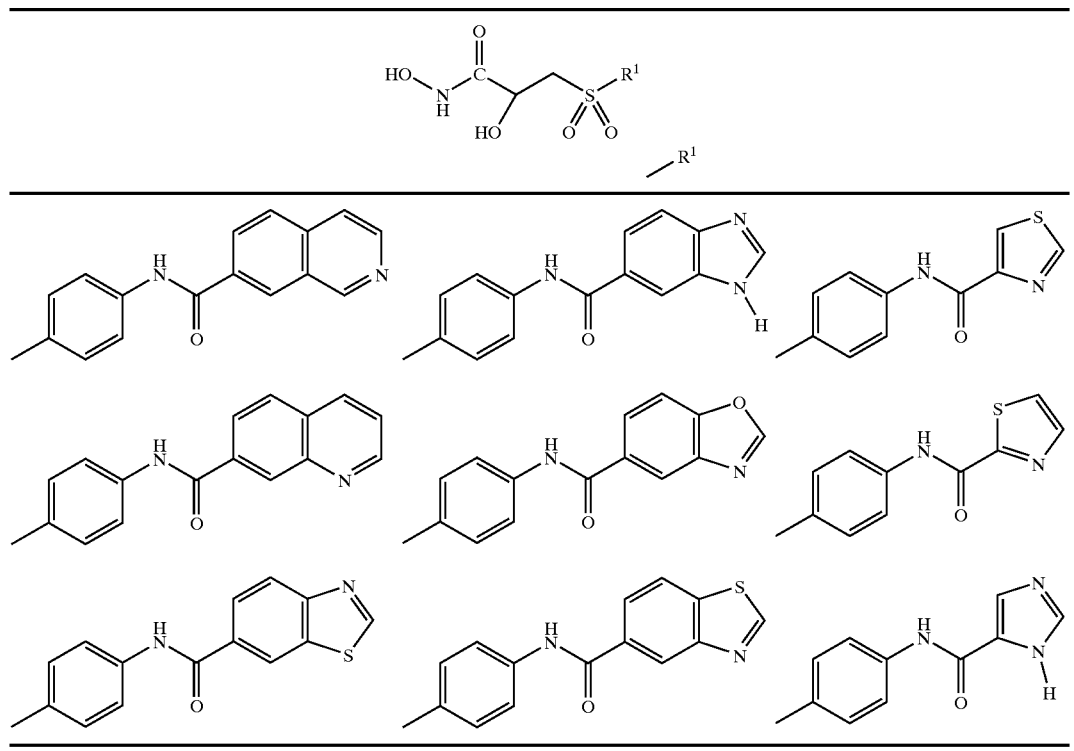
TABLE 42
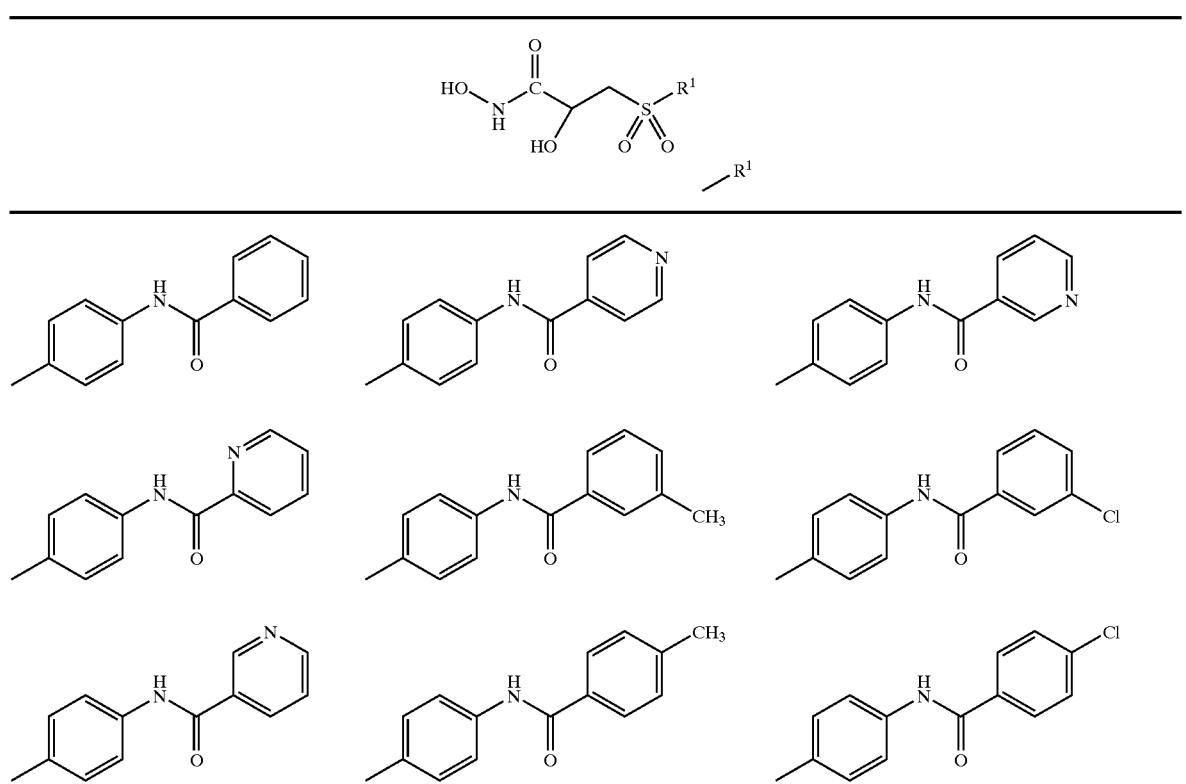

TABLE 42-continued
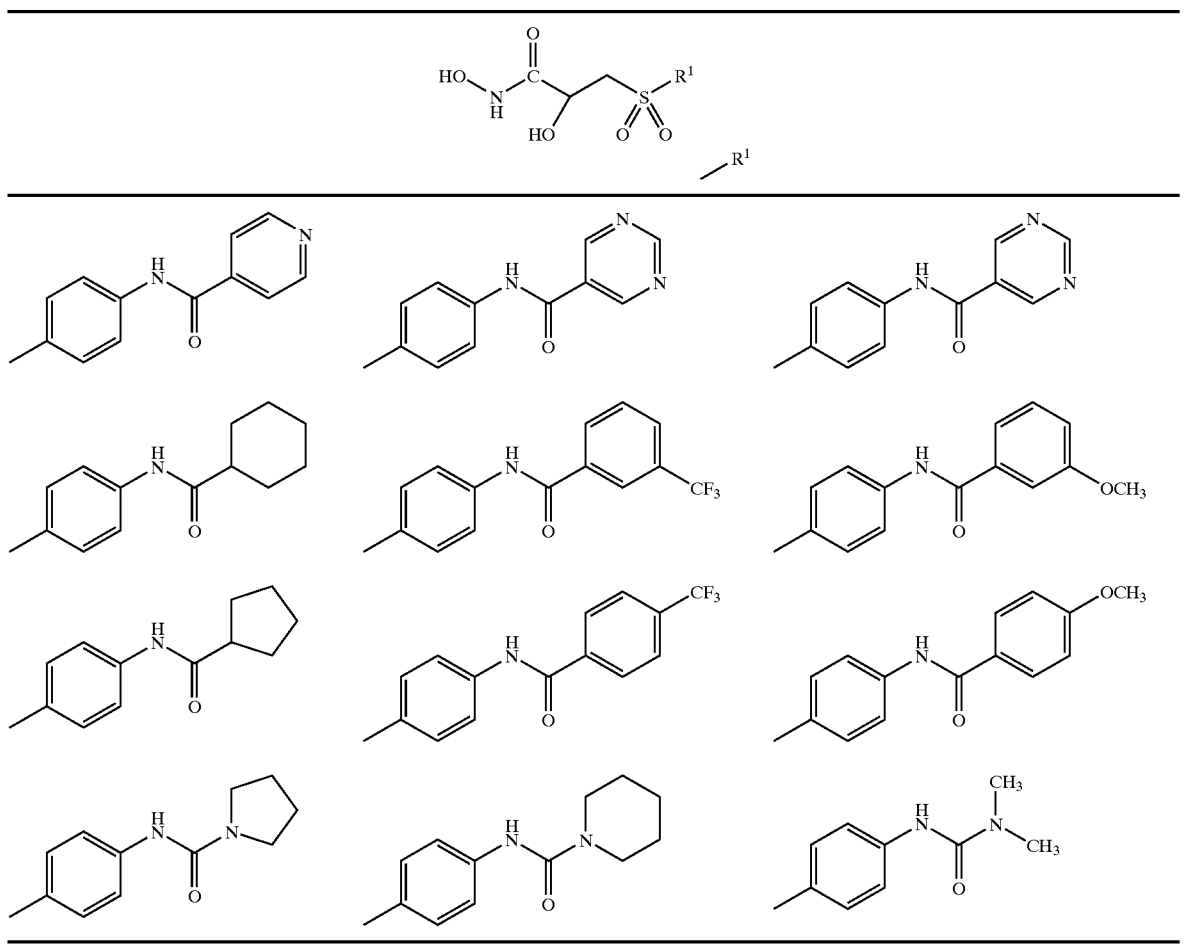
TABLE 43
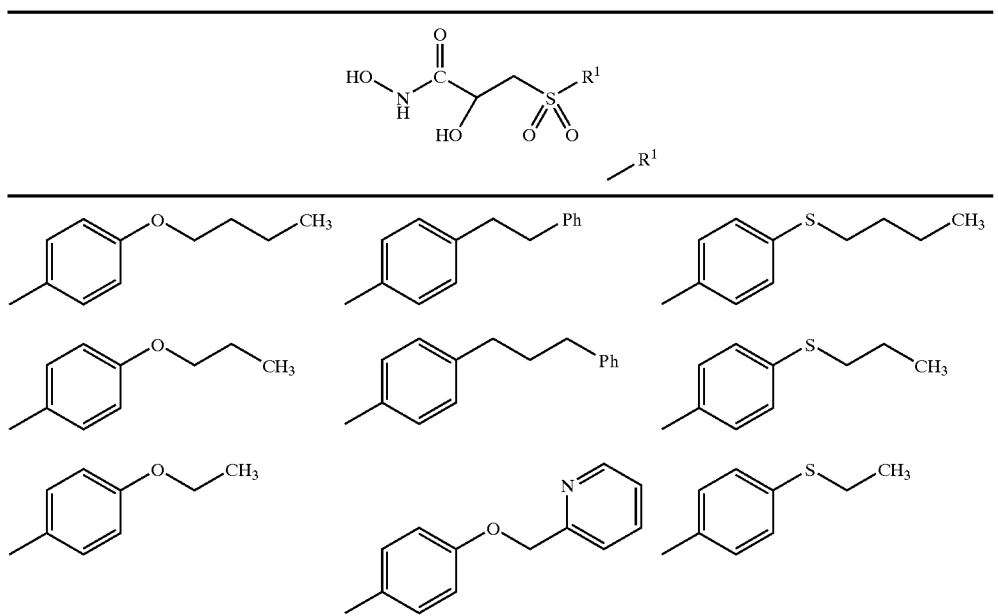

TABLE 43-continued
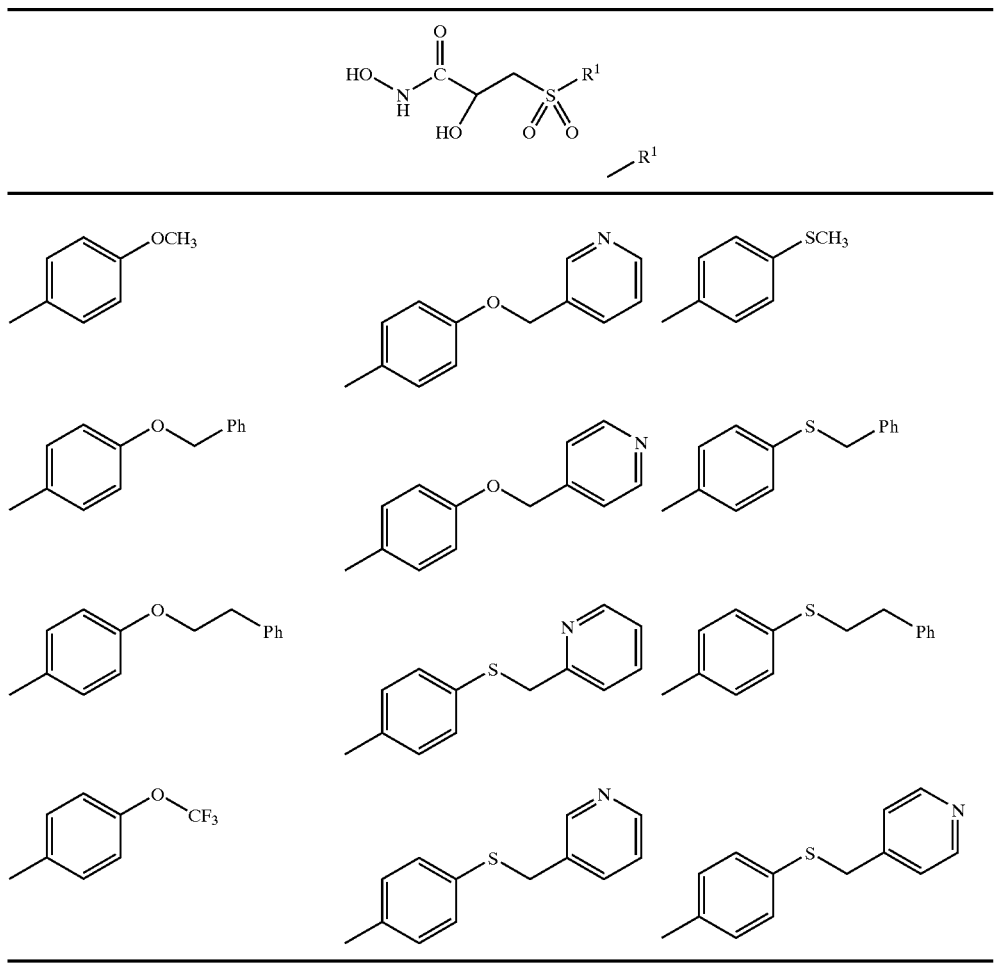
TABLE 44
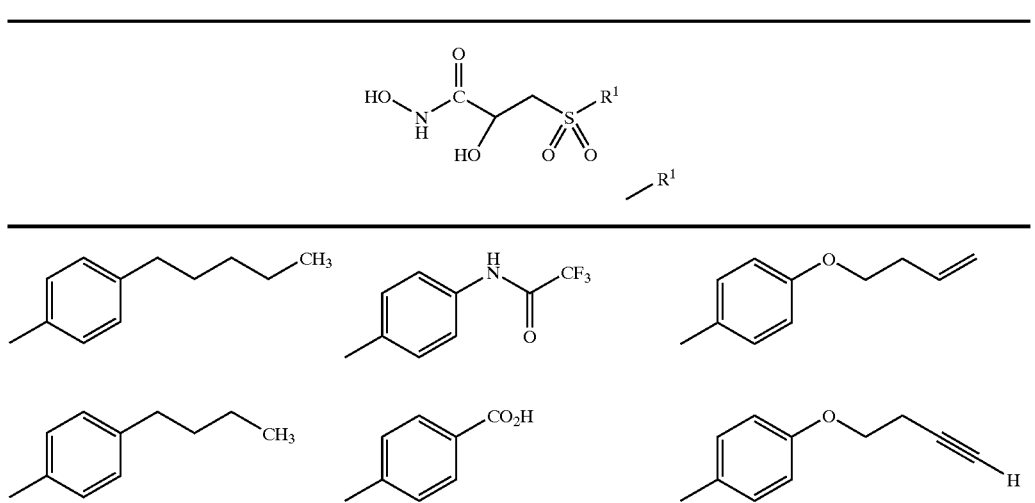

TABLE 44-continued
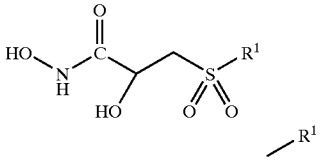
TABLE 45
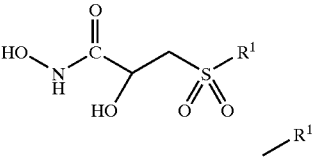

TABLE 45-continued

[Structure: HO-NH-C(=O)-CH(OH)-CH2-S(=O)2-R¹]

—R¹

[Structures of R¹ groups shown]

TABLE 46-continued
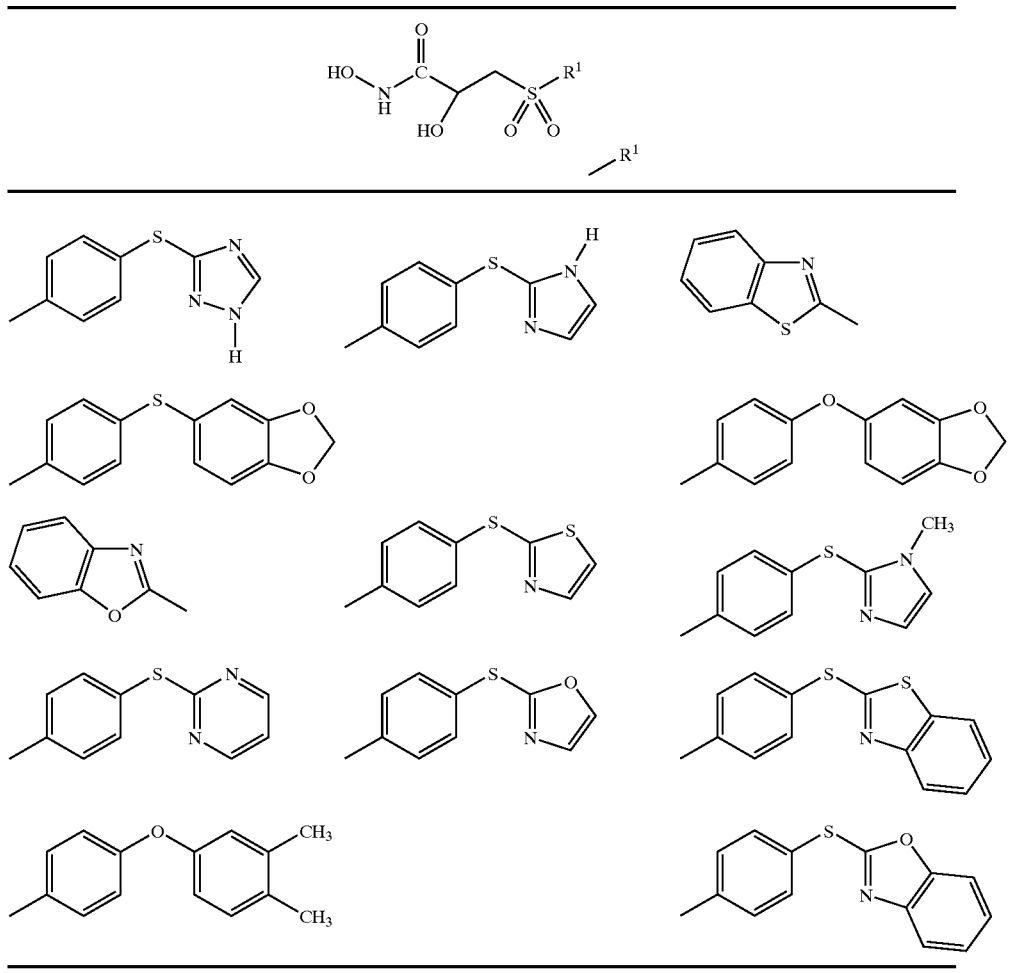
TABLE 47
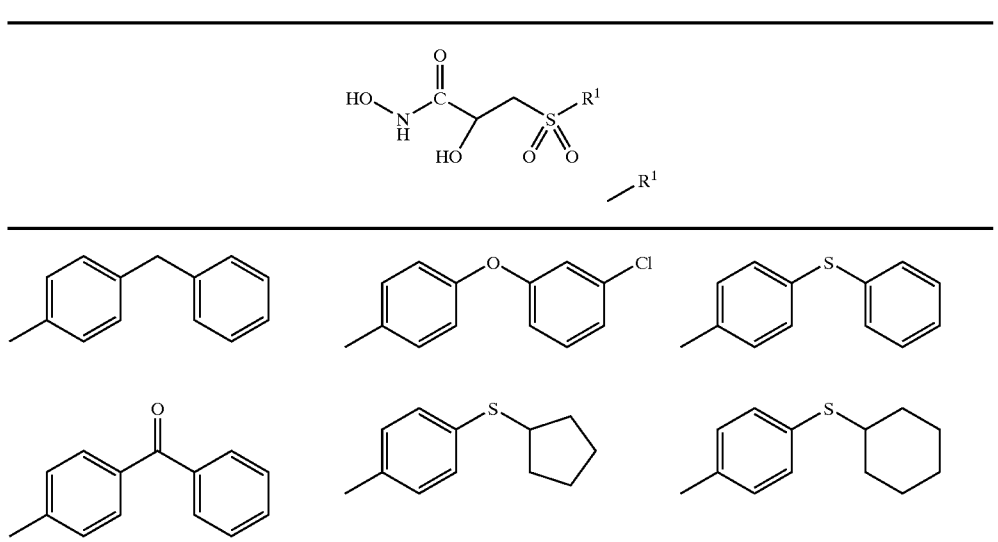

TABLE 47-continued
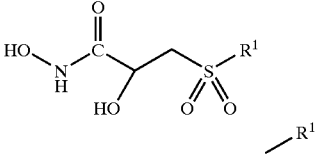
| 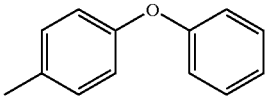 | 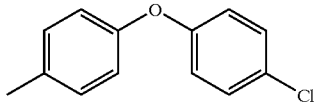 | 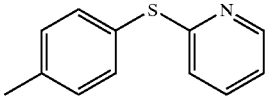 |
|---|---|---|
| 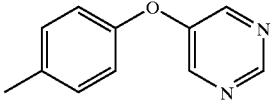 | 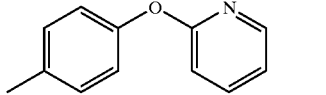 | 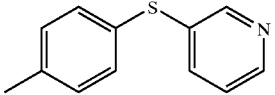 |
| 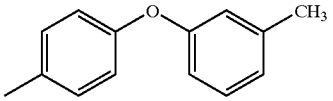 | 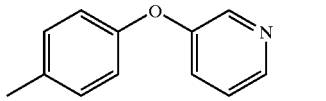 | 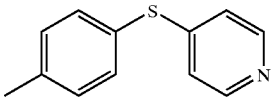 |
| 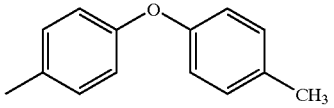 | 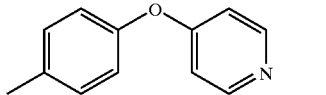 | 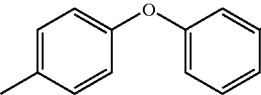 |
| 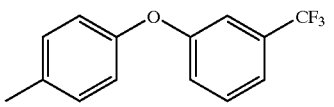 | 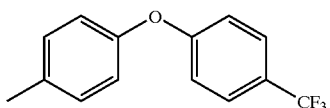 | 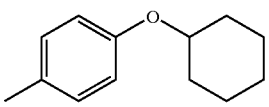 |
TABLE 48
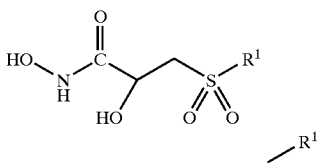
| 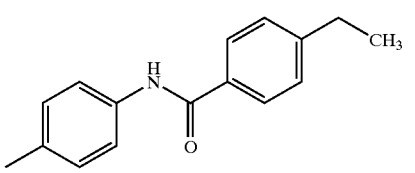 | 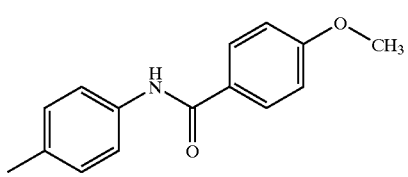 |
|---|---|
| 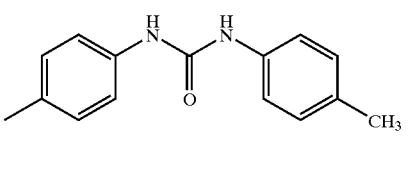 | 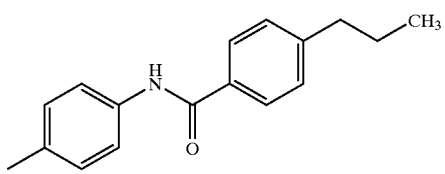 |

TABLE 48-continued
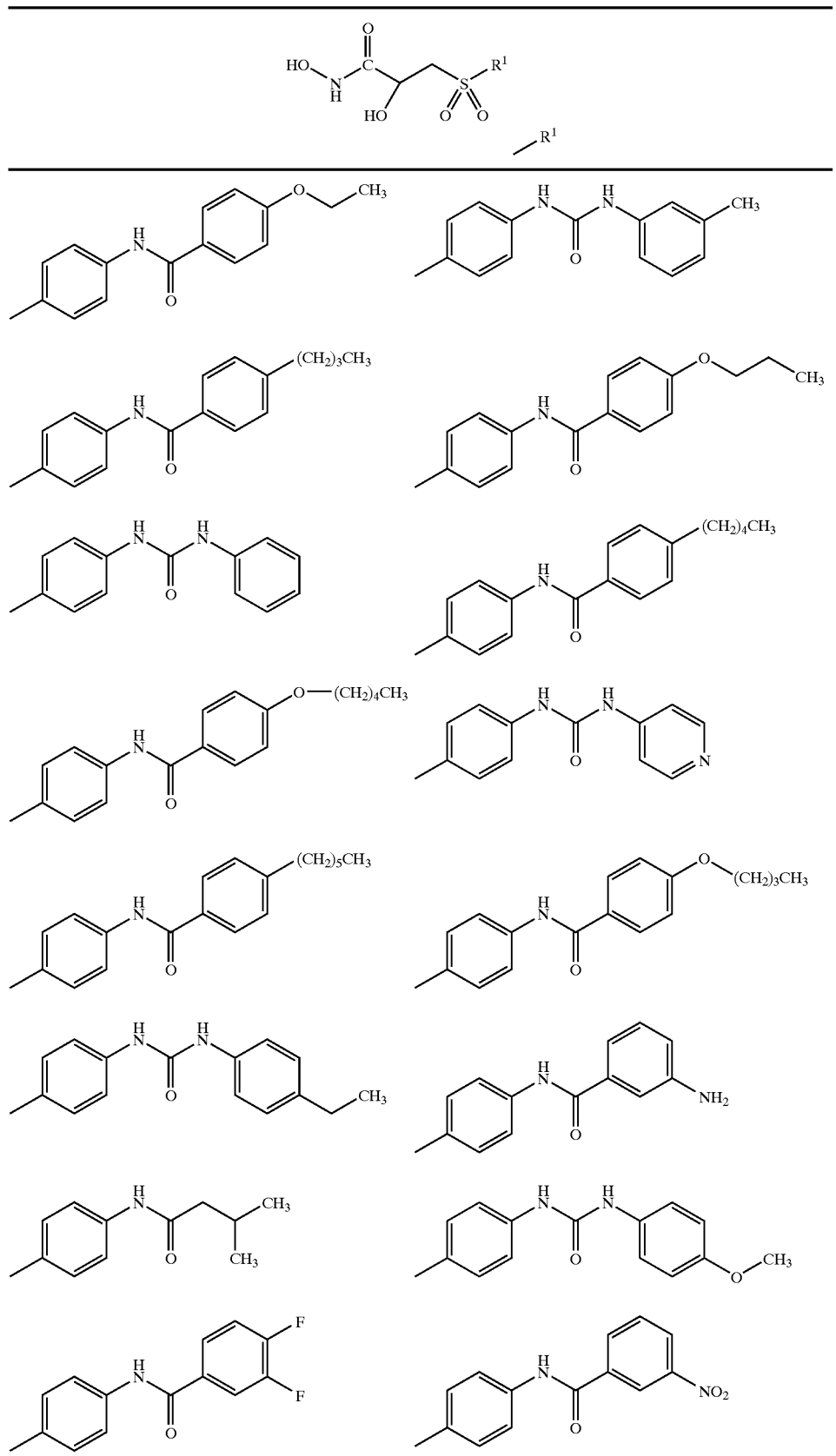

TABLE 48-continued
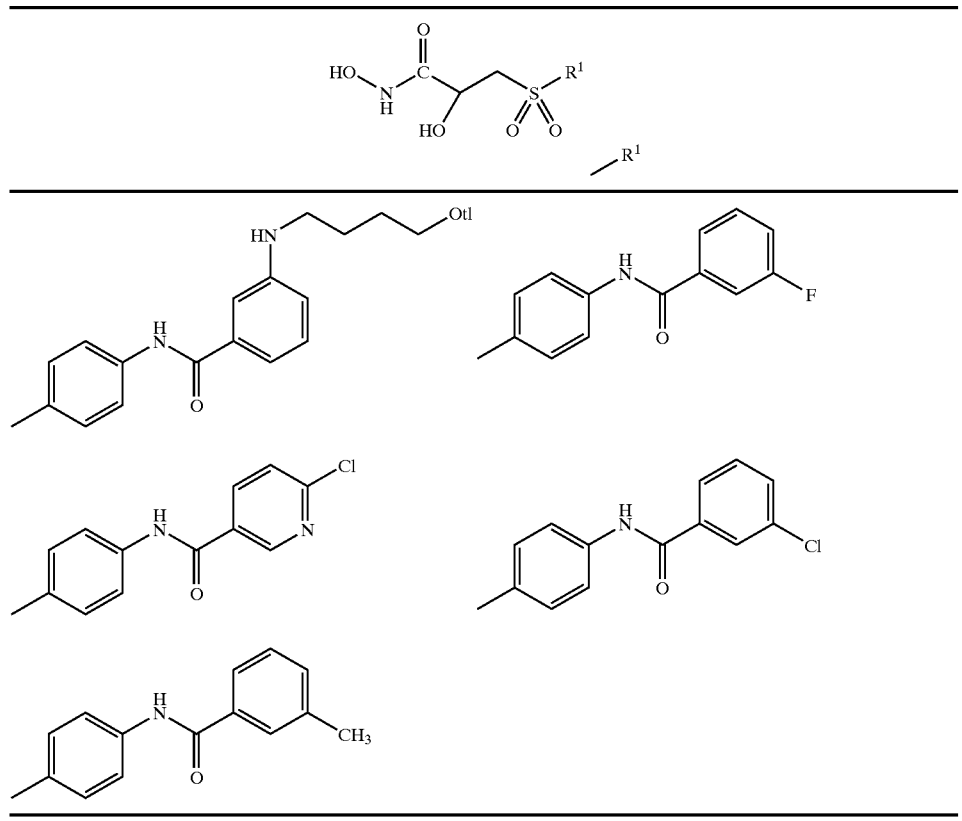
TABLE 49
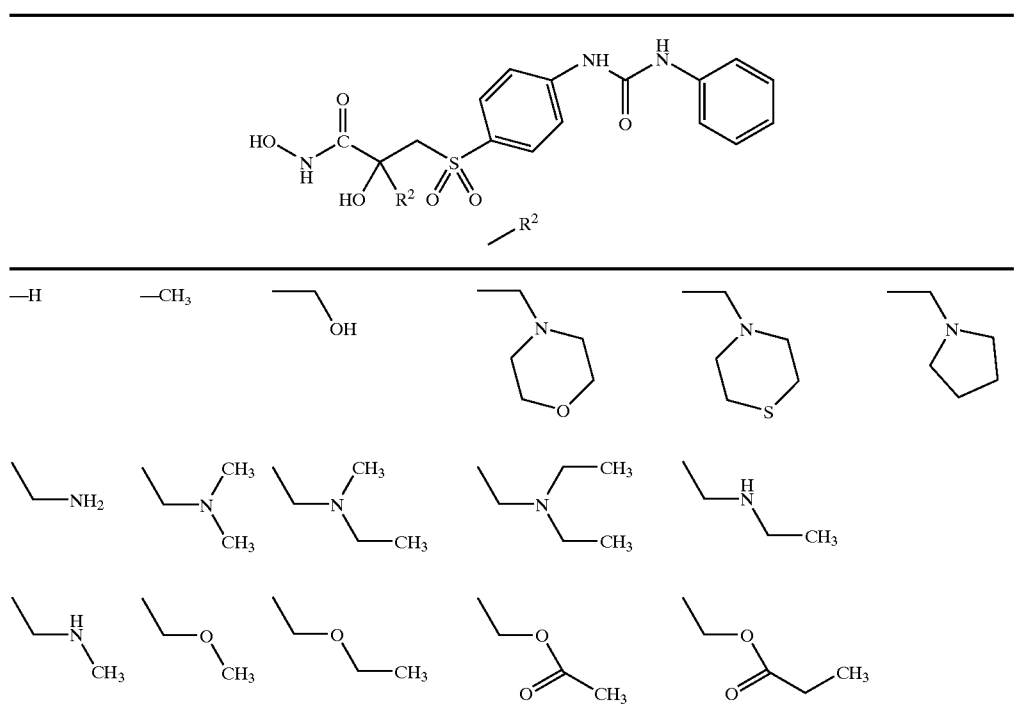

TABLE 49-continued
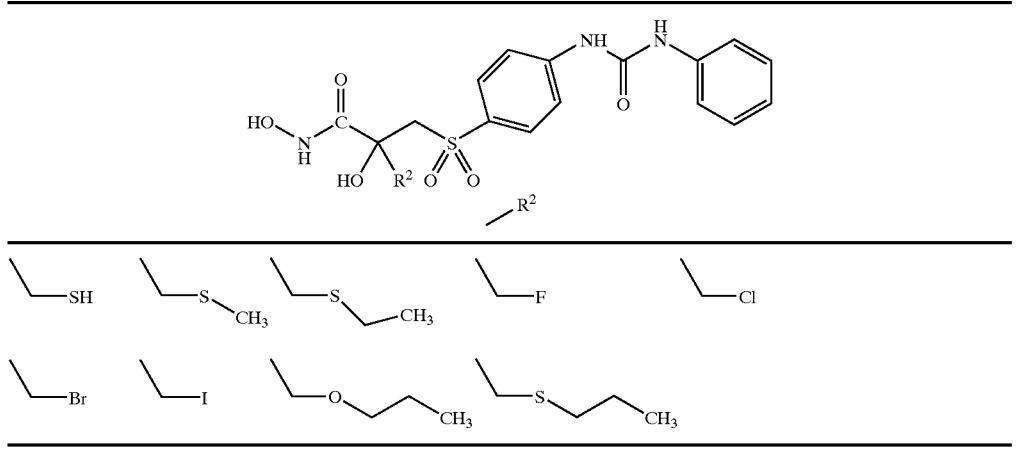
TABLE 50
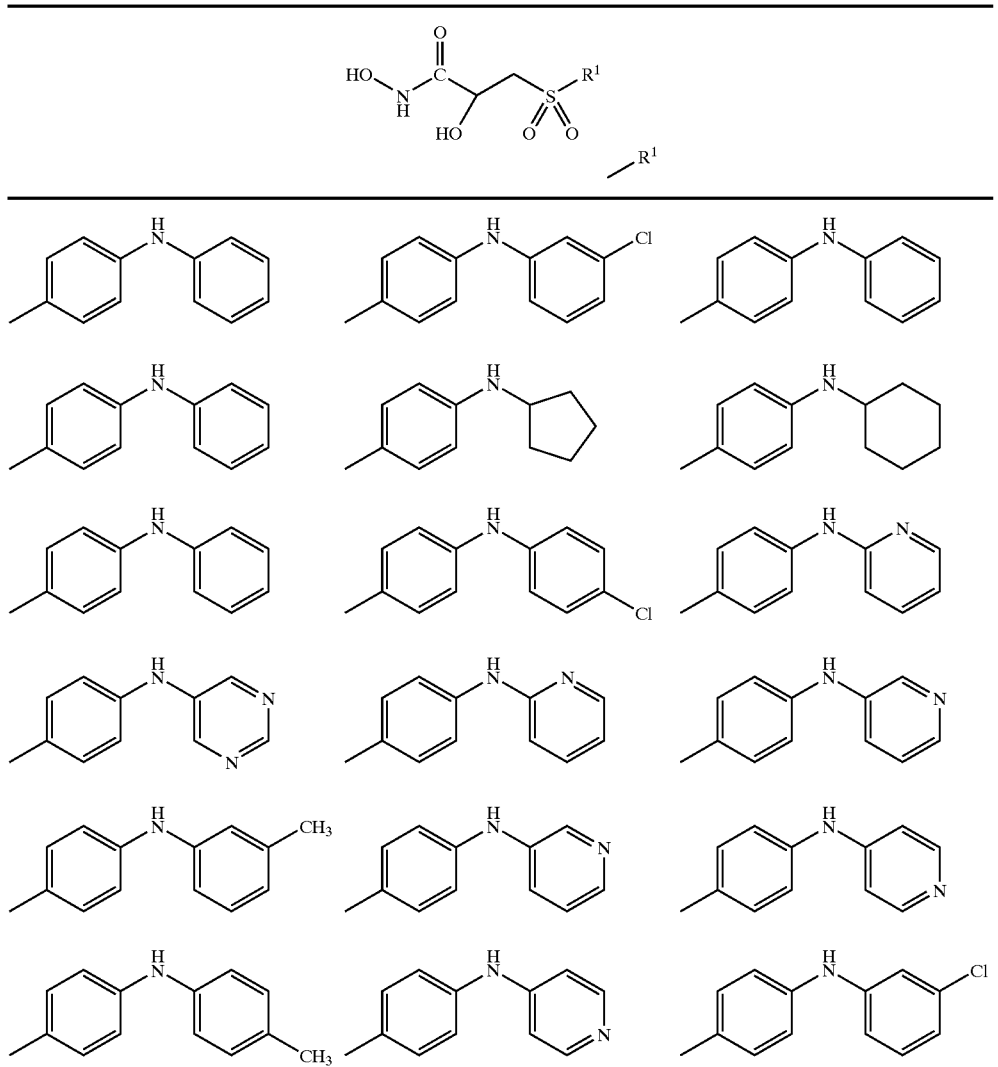

TABLE 50-continued

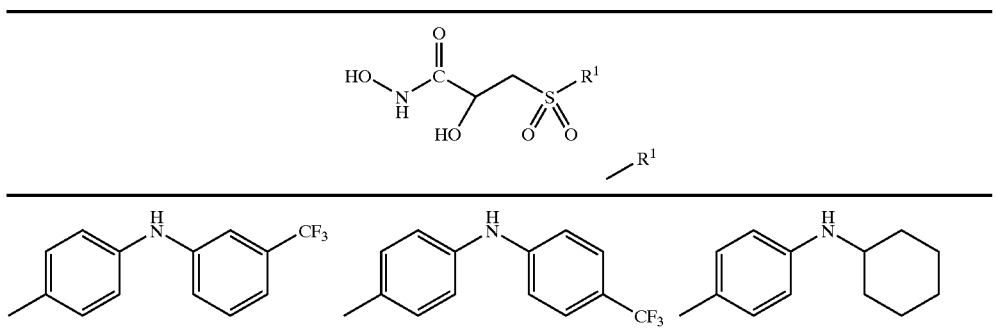

Treatment Process

A process for treating a host mammal having a condition associated with pathological matrix metalloprotease activity is also contemplated. That process comprises administering a compound described hereinbefore in an MMP enzyme-inhibiting effective amount to a mammalian host having such a condition. The use of administration repeated a plurality of times is particularly contemplated.

A contemplated compound is used for treating a host mammal such as a mouse, rat, rabbit, dog, horse, primate such as a monkey, chimpanzee or human that has a condition associated with pathological matrix metalloprotease activity.

Also contemplated is the similar use of a contemplated compound in the treatment of a disease state that can be affected by the activity of metalloproteases such as TNF-A convertase. Exemplary of such disease states are the acute phase responses of shock and sepsis. coagulation responses, hemorrhage and cardiovascular effects, fever and inflammation, anorexia and cachexia.

In treating a disease condition associated with pathological matrix metalloproteinase activity, a contemplated MMP inhibitor compound can be used, where appropriate, in the form of an amine salt derived from an inorganic or organic acid. Exemplary acid salts include but are not limited to the following; acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hydroxy-ethanesulfonate, lactate, maleate, methanesulfonate, nicotinate, 2-naphthalenesulfonate, oxalate, palmoate, pectinate, persulfate, 3-phenylpropionate, picrate, pivalate, propionate, succinate, tartrate, thiocyanate, tosylate, mesylate and undecanoate.

Also, a basic nitrogen-containing group can be quaternized with such agents as lower alkyl ($C_1$–$C_6$) halides, such as methyl, ethyl, propyl, and butyl chloride, bromides, and iodides; dialkyl sulfates like dimethyl, diethyl, dibuytl, and diamyl sulfates, long chain ($C_8$–$C_{20}$) halides such as decyl, lauryl, myristyl and dodecyl chlorides, bromides and iodides, aralkyl halides like benzyl and phenethyl bromides, and others to provide enhanced water-solubility. Water or oil-soluble or dispersible products are thereby obtained as desired. The salts are formed by combining the basic compounds with the desired acid.

Other compounds useful in this invention that are acids can also form salts. Examples include salts with alkali metals or alkaline earth metals, such as sodium, potassium, calcium or magnesium or with organic bases or basic quaternary ammonium salts.

In some cases, the salts can also be used as an aid in the isolation, purification or resolution of the compounds of this invention.

Total daily dose administered to a host mammal in single or divided doses of an MMP enzyme-inhibiting effective amount can be in amounts, for example, of about 0.001 to about 100 mg/kg body weight, preferably about 0.001 to about 30 mg/kg body weight daily and more usually about 0.01 to about 10 mg. Dosage unit compositions can contain such amounts or submultiples thereof to make up the daily dose. A suitable dose can be administered, in multiple sub-doses per day. Multiple doses per day can also increase the total daily dose, should such dosing be desired by the person prescribing the drug.

The dosage regimen for treating a disease condition with a compound and/or composition of this invention is selected in accordance with a variety of factors, including the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed can vary widely and therefore can deviate from the preferred dosage regimen set forth above.

A compound useful in the present invention can be formulated as a pharmaceutical composition. Such a composition can then be administered orally, parenterally, by inhalation spray, rectally, or topically in dosage unit formulations containing conventional nontoxic pharmaceutically acceptable carriers, adjuvants, and vehicles as desired. Topical administration can also involve the use of transdermal administration such as transdermal patches or iontophoresis devices. The term parenteral as used herein includes subcutaneous injections, intravenous, intramuscular, intrasternal injection, or infusion techniques. Formulation of drugs is discussed in, for example, Hoover, John E., *Remington's Pharmaceutical Sciences,* Mack Publishing Co. (Easton, Pa.: 1975) and Liberman, H. A. and Lachman, L., eds., *Pharmaceutical Dosage Forms,* Marcel Decker (New York, N.Y.: 1980).

Injectable preparations, for example, sterile injectable aqueous or oleaginous suspensions can be formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic monoor diglycerides. In addition, fatty acids such as oleic acid find use in the preparation of injectables. Dimethyl acetamide, surfactants including ionic and non-ionic detergents, polyethylene glycols can be used. Mixtures of solvents and wetting agents such as those discussed above are also useful.

Suppositories for rectal administration of the drug can be prepared by mixing the drug with a suitable nonirritating excipient such as cocoa butter, synthetic mono- di- or triglycerides, fatty acids and polyethylene glycols that are sold at ordinary temperatures but liquid at the rectal temperature and will therefore melt in the rectum and release the drug.

Solid dosage forms for oral administration can include capsules, tablets, pills, powders, and granules. In such solid dosage forms, the compounds of this invention are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage form varies depending upon the mammalian host treated and the particular mode of administration.

Preparation of Useful Compounds

Schemes I–IV and 1–2C hereinbelow illustrate general and specific chemical processes and transformations that can be useful for the preparation of compounds useful in this invention; i.e., compounds of Formulas I–IV, with particular emphasis on compounds of Formulas II and IV and similar inhibitors.

A compound of the invention can be produced in accordance with the following synthetic schemes:

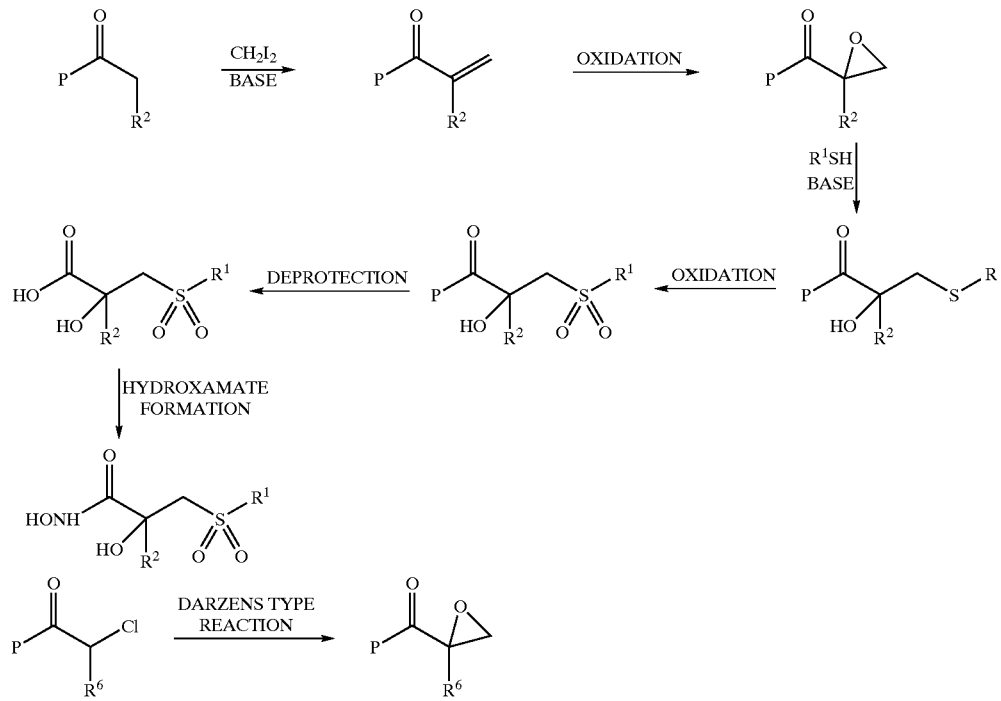

SCHEME 1

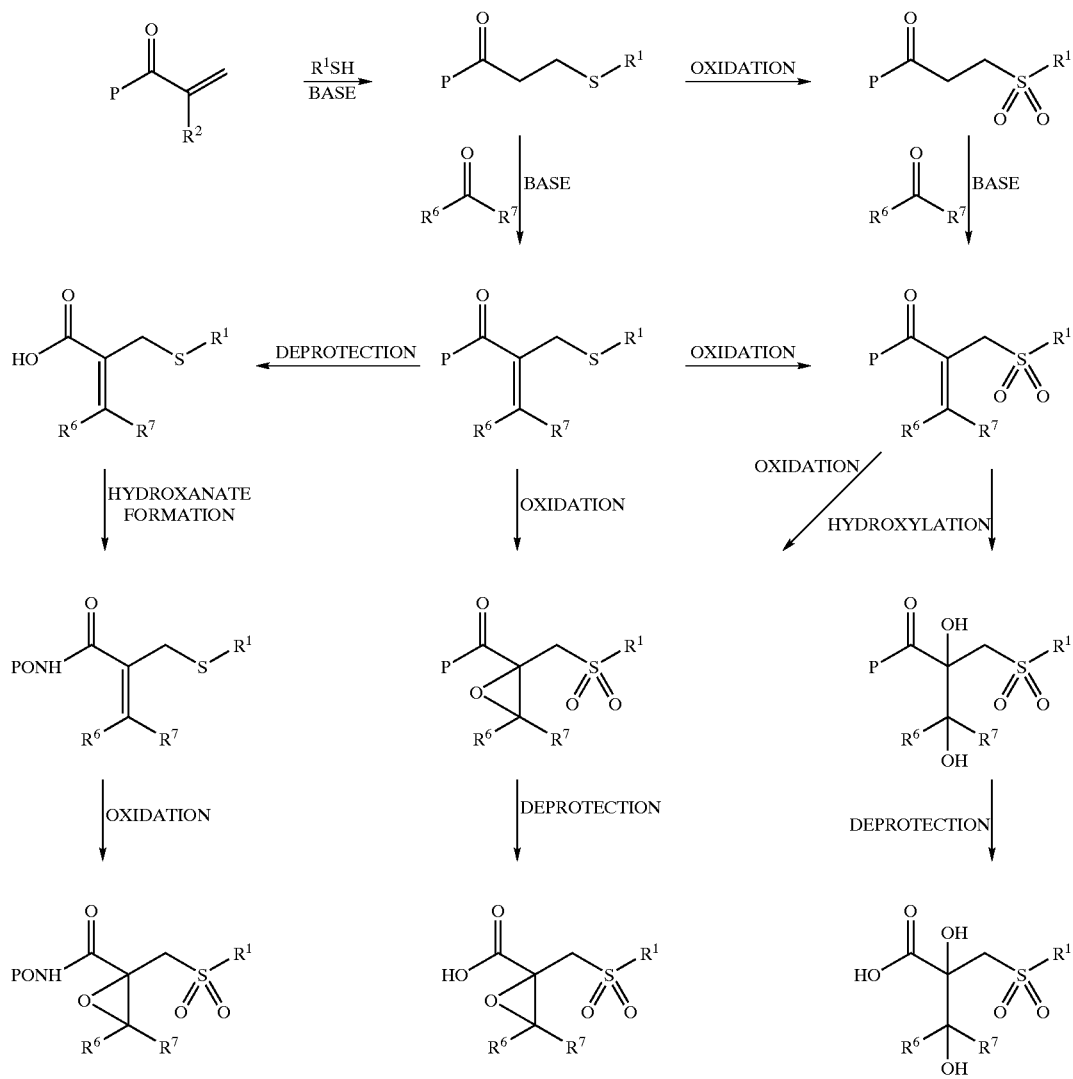
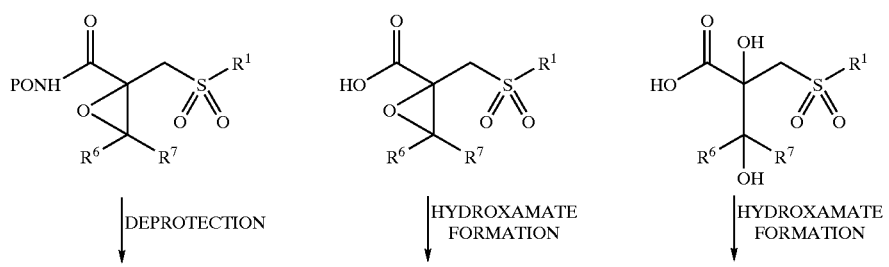

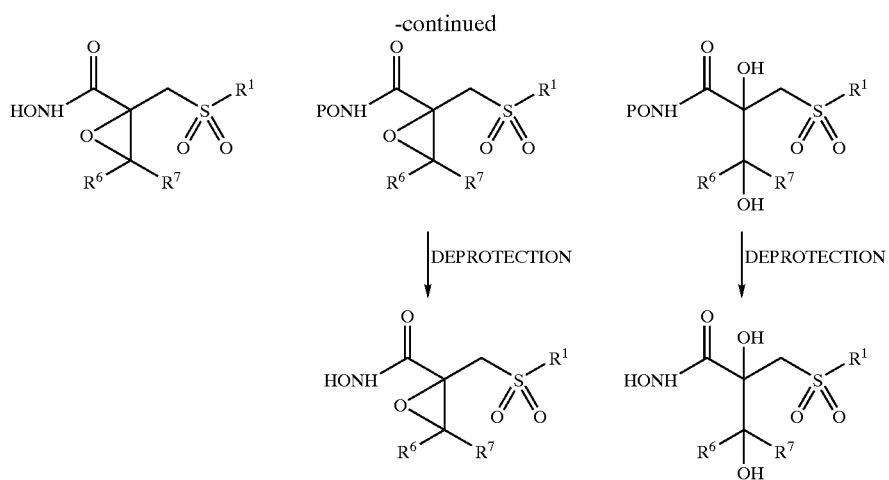
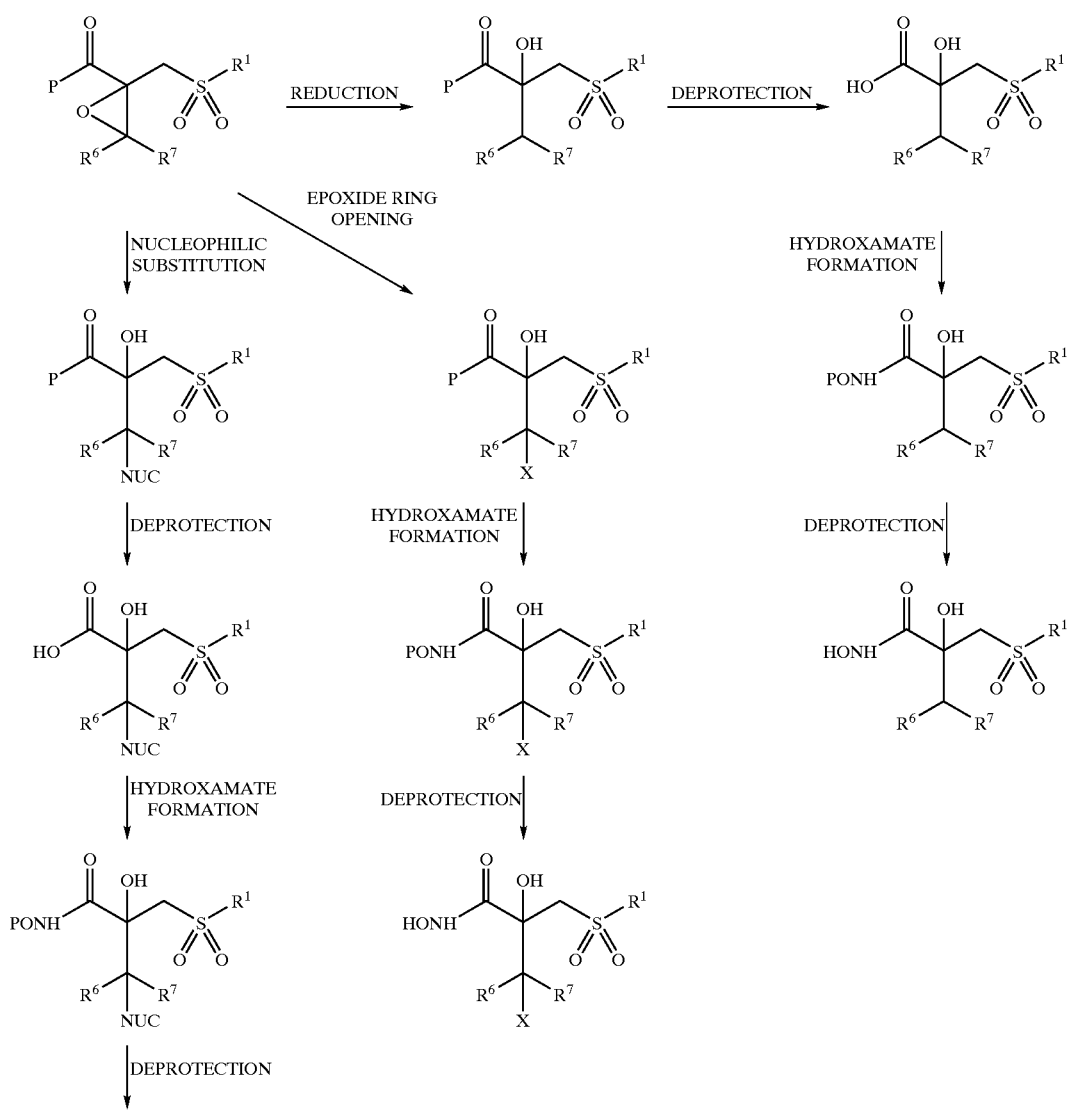
SCHEME III

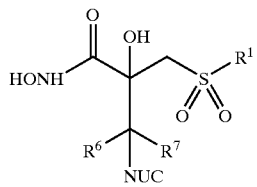

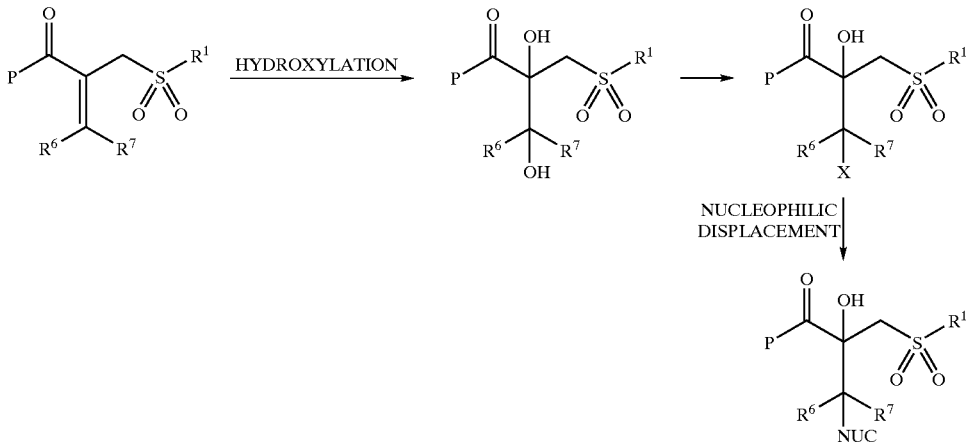

SCHEME IV

Schemes I through IV illustrate general procedures and examples of chemical transformations useful for the preparation of compounds of this invention. Scheme I starts with the conversion of a protected carboxylic acid into a alpha-beta unsaturated protected carboxylic acid wherein $R^2$ and $R^1$ are as defined hereinabove. The preferred reagents are bis-halogenated methanes such as methylene iodide. Bases can be in several categories such as are discussed below. Preferred bases are strong, hindered and/or non-nucleophilic organic bases such metal amides, lithium alkyls or metal hydrides. Preferred solvents are aprotic solvents or dipolar aprotic solvents as discussed below. Most preferred are dipolar aprotic solvents such as DMF.

P represents a carboxylic acid protecting group such as an ester or an acid. P can also represent an —OH group depending upon conditions that are readily recognized by a person skilled in the art.

The double bond compounds produced by this procedure can be oxidized to epoxides. Oxidation can be direct as with, for example, per-acids or hydrogen peroxide or other similar oxidizing agents such as those discussed below. Halohydrin formation with HOCl or halogenation with a halogen such as chlorine or bromine followed by, for example, base treatment with a metal hydroxide, can also lead to the desired epoxide by methods well known in the art. In addition, a Darzens type reaction (glycidic acid derivative formation) wherein a alpha-halo carbonyl compound such as a alpha-chloro carboxylic ester is treated with an aldehyde or ketone in the presence of base to form the epoxide directly. Preferred bases are non-nucleophilic or moderately nucleophilic bases such as metal alcoholates, metal amides, magnesium reagents, lithium reagents or metal hydrides as discussed below.

Scheme I also illustrates opening of an exemplary epoxide intermediate of this invention using a nucleophilic thiol or thiolate reagent. Thiolate nucleophiles can be created by methods well known in the art such as treating a thiol with base in situ or by using a preformed thiolate. Use of a pre-formed thiolate can allow maintenance of a protecting group. These methods are further discussed below as part of our discussion of the Michael reaction. A preferred base is potassium hydroxide if hydrolysis of the protecting group is desired or, for example, a alcoholate such as sodium methoxide if a methyl ester protecting group is to be maintained in use or an alkyl lithium or lithium amide if maintaining a protecting group is desired.

The product of the nucleophilic ring opening reaction (epoxide ring opening) can be oxidized to the sulfone in one step using two equivalents of oxidizing agent. The starting material for this reaction can be a sulfide wherein P is a protecting group such as an ester or amide or a carboxylic acid or where P is OH. Reagents for this process can include peroxymonosulfate OXONE®), hydrogen peroxide, meta-chloroperbenzoic acid, perbenzoic acid, peracetic acid, perlactic acid, tert-butyl peroxide, tert-butyl hydroperoxide, tert-butyl hypochlorite, sodium hypochlorite, hypochlorous acid, sodium meta-periodate, periodic acid and the like. Protic, non-protic, dipolar aprotic solvents, either pure or mixed, can be chosen, for example, methanol/water.

The oxidation can be carried out at temperature of about −68° to about 50° degrees centigrade and normally selected from a range −10° C. to about 40° C. This oxidation can be carried out in two steps via the synthesis of sulfoxide which requires the use of only about one equivalent of one of the above oxidizing agents preferable at about zero degrees C. The solvents listed above can be used with these selective oxidations to a sulfoxide with, for example, methanol or methanol/water being preferred along with a temperature of from about −10° C. to 30° C. It can be desirable in the case of more active oxidizing agents, but not required, that the reactions be carried out under an inert gas atmosphere with or without degassed solvents. The sulfoxide is then oxidized to the sulfone with a second equivalent of oxidizing agent in a separate step that can be carried out at a stage of the synthesis chosen by a person skilled in the art. Again, at this stage of the synthesis of the product compounds, the person skilled in the art can elect to either keep or remove the protecting group by the choice of reagents, solvents and pH conditions. For example, protic solvents or mixed solvents such as water or water/solvent mixtures under basic conditions can produce the acid directly whereas some peroxy acids in non-protic or dipolar aprotic solvents can oxidize the sulfur without removing the protecting group. A preferred oxidizing regent is peroxymonosulfate with the reaction carried out under conditions wherein the preferred protecting group, a methyl ester, is hydrolyzed.

Scheme I also illustrates hydroxamate formation to prepare the hydroxamic acid products of this invention. The preferred method in this case is direct reaction with hydroxylamine (aq) of an activated ester and diimide coupling. A second preferred method is exchange with, for example, a methyl ester. This type of reaction is well known in the art especially the peptide synthesis art and is discussed further below.

Scheme II illustrates the Michael reaction of a thiol such as $R^1SH$ with a protected alpha-beta unsaturated carboxylic acid to form the products of this invention; i.e., a sulfide amide or ester wherein the amide or ester are serving as the carboxylic acid protecting groups. This reaction can be base mediated by the use of catalytic amounts of some bases or carried out with an equivalent or more of a base or by the addition of a preformed thiolate reagent such as a preformed thiol salt.

Non-limiting examples include sodium, potassium, lithium, calcium, or magnesium salts of thiophenol, substituted thiophenols or heteroarylthiols as defined above. Bases that can be used include, for example, metal hydroxides such as sodium, potassium, lithium or magnesium hydroxide, oxides such as those of sodium, potassium, lithium, calcium or magnesium, metal carbonates such as those of sodium, potassium, lithium, calcium or magnesium, metal bicarbonates such as sodium bicarbonate or potassium bicarbonate, I°, II° or III° organic amines such as alkyl amines, arylalkyl amines, alkylarylalkyl amines, heterocyclic amines or heteroaryl amines, ammonium hydroxides or quaternary ammonium hydroxides. As non-limiting examples. such amines can include triethyl amine, trimethyl amine, diisopropyl amine, methyldiisopropyl amine, diazabicyclononane, tribenzyl amine, dimethylbenzyl amine, morpholine, N-methylmorpholine, N,N'-dimethylpiperazine, N-ethylpiperidine, 1,1,5,5-tetramethylpiperidine, dimethylaminopyridine, pyridine, quinoline,.tetramethylethylenediamine and the like. Non-limiting examples of ammonium hydroxides, usually made from amines and water, can include ammonium hydroxide, triethyl ammonium hydroxide, trimethyl ammonium hydroxide, methyldiiospropyl ammonium hydroxide, tribenzyl ammonium hydroxide, dimethylbenzyl ammonium hydroxide, morpholinium hydroxide, N-methylmorpholinium hydroxide, N,N'-dimethylpiperazinium hydroxide, N-ethylpiperidinium hydroxide, and the like. As non-limiting examples, quaternary ammonium hydroxides can include tetraethyl ammonium hydroxide, tetramethyl ammonium hydroxide, dimethyldiiospropyl ammonium hydroxide, benzylmethyldiisopropyl ammonium hydroxide, methyldiazabicyclononyl ammonium hydroxide, methyltribenzyl ammonium hydroxide, N,N-dimethylmorpholinium hydroxide, N,N,N',N',-tetramethylpiperazenium hydroxide, and N-ethyl-N'-hexylpiperidinium hydroxide and the like. Metal hydrides, amide or alcoholates such as calcium hydride, sodium hydride, potassium hydride, lithium hydride, sodium methoxide, potassium tert-butoxide, calcium ethoxide, magnesium ethoxide, sodium amide, potassium diisopropyl amide and the like can also be suitable reagents. Organometallic deprotonating agents such as alkyl or aryl lithium reagents such as methyl, phenyl or butyl lithium, Grignard reagents such as methylmagnesium bromide or methymagnesium chloride, organocadium reagents such as dimethylcadium and the like can also serve as bases for causing salt formation or catalyzing the reaction. Quaternary ammonium hydroxides or mixed salts are also useful for aiding phase transfer couplings or serving as phase transfer reagents.

The reaction media can consist of a single solvent, mixed solvents of the same or different classes or serve as a reagent in a single or mixed solvent system. The solvents can be protic, non-protic or dipolar aprotic.

Non-limiting examples of protic solvents include water, methanol (MeOH), denatured or pure 95% or absolute ethanol, isopropanol and the like. Typical non-protic solvents include acetone, tetrahydrofurane (THF), dioxane, diethylether, tert-butylmethyl ether (TBME), aromatics such as xylene, toluene, or benzene, ethyl acetate, methyl acetate, butyl acetate, trichloroethane, methylene chloride, ethylenedichloride (EDC), hexane, heptane, isooctane, cyclohexane and the like. Dipolar aprotic solvents include compounds such as dimethylformamide (DMF), dimethylacetamide (DMAc), acetonitrile, nitromethane, tetramethylurea, N-methylpyrrolidone and the like. Non-limiting examples of reagents that can be used as solvents or as part of a mixed solvent system include organic or inorganic monoor multiprotic acids or bases such as hydrochloric acid, phosphoric acid, sulfuric acid, acetic acid, formic acid, citric acid, succinic acid, triethylamine, morpholine, N-methylmorpholine, piperidine, pyrazine, piperazine, pyridine, potassium hydroxide, sodium hydroxide, alcohols or amines for making esters or amides or thiols for making the products of this invention and the like.

Room temperature or less or moderate warming (−10° C. to 60° C.) are the preferred temperatures of the reaction. If desired, the reaction temperature can be about −76° C. to the reflux point of the reaction solvent or solvents.

The beta-$SR^1$ derivative prepared as discussed above can then be carried forward as such or oxidized to the corresponding sulfone by methods discussed above. Either of these products can then be reacted under condensation reaction conditions with an aldehyde or ketone wherein $R^6$ and $R^7$ can be, independently, hydrogen or the groups represented by $R^2$ with one less carbon atom; i.e., that carbon atom illustrated in the structures that is directly attached to the carbon atom alpha to the carbonyl group. This produces the unsaturated sulfide or sulfone containing carboxylic acids or protected carboxylic acids illustrated in Scheme II.

The alpha-beta unsaturated sulfide can be oxidized to the sulfone following the condensation as is shown in the scheme. Oxidation of either of unsaturated sulfide or sulfone containing carboxylic acids or protected carboxylic acids to the epoxide containing analogs is also illustrated. Oxidation of the sulfide can produce both the epoxide ring and the sulfone in one step.

Hydroxylation of the double bond is also illustrated in Scheme II. This process is well known in the art and examples reagents for such conversions include osmium tetroxide, permanganate salts including hydroxide if desired, iodine with lead acetate, halohydrin formation followed by displacement of the halogen with base or its conversion into an epoxide followed by ring opening with hydroxide or catalytic osmium tetroxide in the presence of an agent such as N-methyl-morpholine-N-oxide (NMM-N-oxide) for its recycling in situ (re-oxidation) to the tetroxide.

The Schemes illustrate conversion of sulfides or sulfones into hydroxamic acid derivatives wherein P is hydrogen or a protected intermediate such as an O-arylalkylether, acyl or O-cycloalkoxyalkylether group. In the case of compounds where P=H, treatment with one or more equivalents of hydroxylamine hydrochloride at room temperature or above in a solvent or solvents such as those listed above can provide hydroxamic acid compounds of this invention directly. There can be an exchange process also such as that between a methyl ester and a hydroxylamine that can be further catalyzed by the addition of additional acid. Alternatively, a base such as a salt of an alcohol used as a solvent, for example, sodium methoxide in methanol, can be used to form hydroxylamine in situ which can exchange with an ester-or amide.

The exchange can also be carried out with a protected hydroxyl amine such as tetrahydropyranylhydroxyamine (THPONH$_2$), benzylhydroxylamine (BnONH$_2$), and the like in which case compounds wherein P is tetrahydropyranyl (THP) or benzyl (Bn) are the products. Removal of the protecting groups when desired, for example, following further transformations in another part of the molecule or following storage, is accomplished by standard methods well known in the art such as acid hydrolysis of the THP group or reductive removal of the benzyl group with hydrogen and a metal catalyst such as palladium, platinum, platinum oxide, palladium on carbon or nickel.

Alternatively, the carboxylic acids of this invention can be converted into activated carbonyl compounds using reagents well known in the art including the peptide and protein synthesis and amino acid coupling or conjugation art. Examples of such reagents are thionyl chloride, oxalyl chloride, phosphorus oxychloride, HOBT, isobutylchloroformate an the like with or without the use of intermediate condensing agents (carbonyl activating) such as the diimides. These valuable activated carbonyl intermediates (acid chlorides, mixed anhydrides and the like) can then be transformed into hydroxamic acids or hydroxamic acid derivatives such as those where P is H, benzyl or THP by condensation with hydroxyl amine or the O-protected hydroxyl amine derivative.

The carboxylic acids of this invention can be prepared and used directly or, as mentioned above, in a protected form. Protected groups for carboxylic acids are well known in the art and include such functional groups as esters, amides, ortho-esters, and groups generally known as ethers such as tetrahydropyranyl ethers or tetrahydropyranyl esters. Alkyl esters such as methyl, ethyl or tert-butyl esters and aralkyl esters such as benzyl, benzhydryl and trityl esters are well known in the art as is their preparation and removal. Amides, either primary, secondary or tertiary, are also well known in the art as are their preparation and removal. Many amides and esters are commercially available. The preferred protecting group is the methyl ester and the preferred method of conversion of the ester into the acid is via base hydrolysis or the use of a basic reagent or basic conditions in a particular reaction wherein this conversion is performed in situ in a single vessel.

Scheme III illustrates another general method of synthesis of the sulfone containing carbonyl compounds of this invention; i.e., use of the SN$_2$ class of reactions. A bimolecular nucleophilic displacement (SN$_2$) reaction is illustrated where an epoxide ring is opened or an activated hydroxyl group derivative of a diol is displace or where an alcohol is converted into a nucleophilic salt (hydroxyl anion salt) by a base. In the latter example, a preparation of the compounds of this invention wherein R$^2$ is methoxyalkyl is by conversion of a hydroxyl group into it alkoxide anion as can be done with base treatment and preferably using a non-nucleophilic base such as sodium hydride, calcium hydride, potassium hydride or an alkyl lithium or amide reagent. A preferred base is sodium hydride. A preferred electrophile; i.e., compound undergoing nucleophilic attack, is an methyl halide or organic sulfonate methyl ester. The most preferred electrophile is methyl iodide. The solvents, solvent mixtures or solvent/reagent mixtures discussed are satisfactory but non-protic or dipolar aprotic solvents such as acetone, acetonitrile, DMF and the like are examples of a preferred class. Salts of these amines can be prepared by standard methods known in the art, e.g., treatment of an amine with HCl to form a hydrochloride salt.

Other SN$_2$ used in the preparation of compounds of this invention involve conversion of an alcohol of the diols shown in the schemes into a electrophile such as a halide or a organic sulfonate ester. Examples of halides are chlorides, bromides or iodides and their preparation is well known in the art. Examples of organic sulfonate esters include tosylates, benzene sulfonates, camphorsulfonates, mesylates and triflates and their preparation is well known in the art. Preferred halides are bromides and preferred sulfonates are trifluoromethanesulfonates (triflates). An example of a method of preparing a halide is treatment of a double bone with a hypohalite or opening an epoxide ring with a hydrohalic acid such as HBr, HCl or HI. An example of a method of preparing a sulfonate ester is treatment of the alcohol with a base such as a tertiary amine or hindered or non-nucleophilic base as discussed above to form an alkoxide anion followed by the addition of a sulfonic acid anhydride or chloride such as triflic anhydride or methanesulfonyl chloride. Displacement (SN$_2$) of the halide or sulfonate leaving group with ammonia, an alkyl amine, a di-alkylamine, morpholine, pyrrolidine or thiomorpholine can provide compounds of this invention. Preferred solvents for these reactions are listed above and include dipolar aprotic solvents such as DMF.

The selection of an atmosphere for the reactions of this Scheme as well as the other Schemes depends, as usual, a number of variables known to those skilled in the art. The choices can be an inert atmosphere such as nitrogen, argon, helium and the like or normal or dry air. Preferred is the use of an inert atmosphere if there is an uncertantity as to the requirements of the process. One of these variables particularly requiring the attention of the skilled person is control of oxidation by air or another means of a thiol or the salt of a thiol to its corresponding disulfide or mixed disulfide. The used of a damp atmosphere while carrying out an organometallic compound requiring synthesis not desirable for either economic or safety reasons whereas the use of air is normal for aqueous hydrolysis or exchange reactions where oxidation, for example, is not probable.

Protecting groups are used as desired in the preparation of the compounds of this invention and are discussed above.

However, the decision to use protecting groups or not as well as the selection of which protecting group to use for a particular functional group is based on a particular objective and is made by a person of ordinary skill in the art. For example, a factor in the choice of a methyl ester and tert-butyl ester for the protection of a particular carboxylic acid function will vary depending upon the preferred method of preparation and the preferred method removal. For example, a methyl ester is known to be readily hydrolyzed by base or exchanged by an amine or hydroxyl amine whereas a tert-butyl ester is relatively resistant to removal by base or exchange but readily removed by acids. Such protecting groups can include acyl groups, carbamoyl groups, ethers, alkoxyalkyl ethers, cycloalkyloxy ethers, arylalkyl groups trisubstituted silyl groups and the like. Examples of such protecting groups include acetyl, THP, Benzyl, Z (benzyloxycarbonyl), tert-butyldimethylsilyl (TBDMS) groups and the like. Protecting groups are discussed in, for example, Green, T., "Protecting Groups in Organic Chemistry", and other review papers and in other books.

Optically active compound isomers as well as mixed or non-optically active compound isomers are specifically intended to be included in this discussion and as part of this invention. Examples of isomers are RS isomers, enantiomers, diastereomers, racemates, cis isomers, trans isomers, E isomers, Z isomers, syn-isomers, anti-isomers, tautomers and the like. Aryl, heterocyclo or heteroaryl tautomers, heteroatom isomers and ortho, meta or para substitution isomers are also included as isomers. Solvates or solvent addition compounds such as hydrates or alcoholates are also specifically included both as chemicals of this invention and in, for example, formulations or pharmaceutical compositions for delivery.

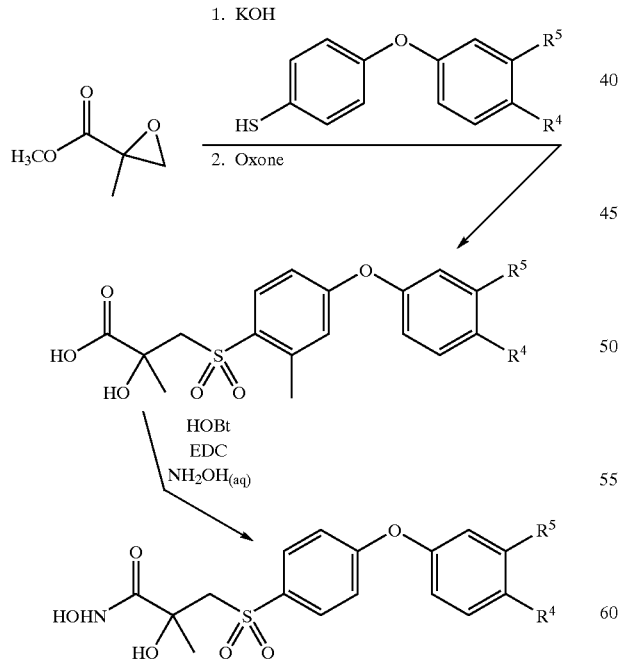

Example 1, R⁴ = R⁵ = H
Example 5, R⁴ = R⁵ = CH₃

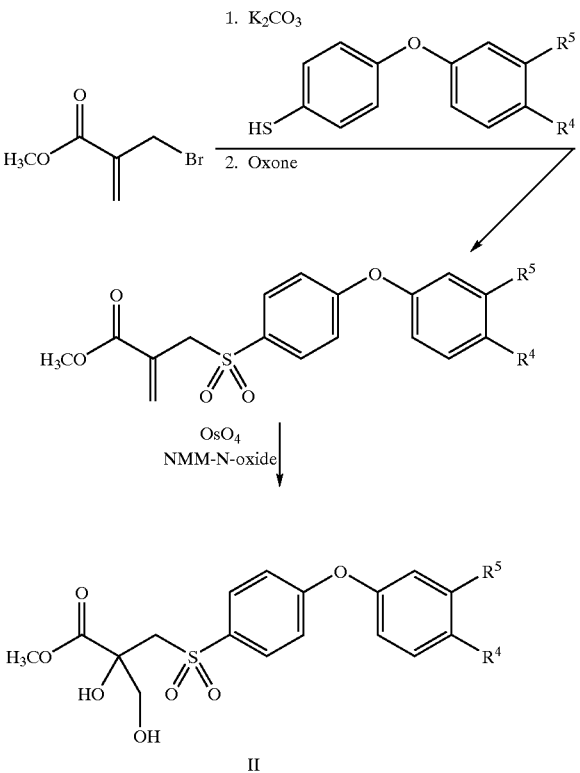

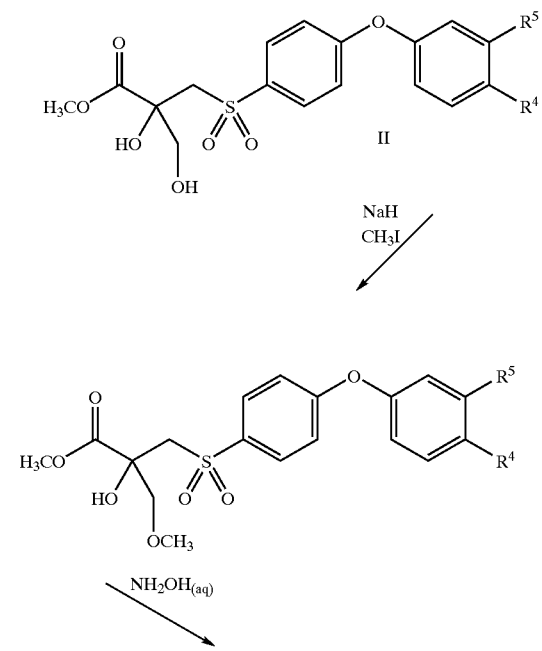

143
-continued

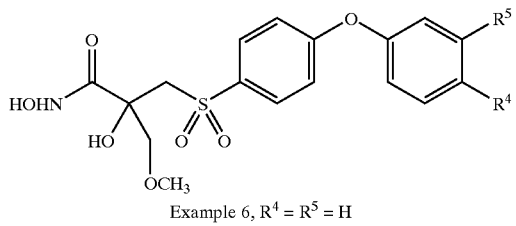

Example 6, R⁴ = R⁵ = H

Scheme 2B:
Examples 2–4, 6 and 7

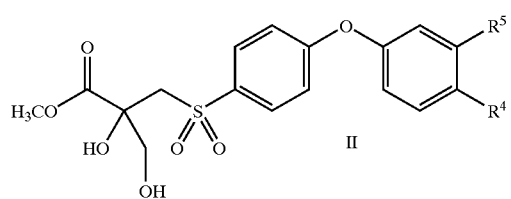

NH₂OH(aq)

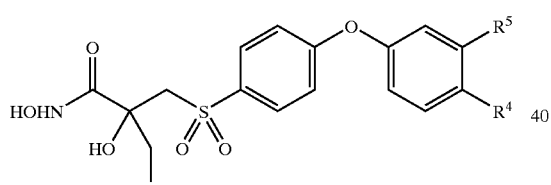

Example 2, R⁴ = R⁵ = H
Example 4, R⁴ = R⁵ = CH₃

Scheme 2C:
Examples 2–4, 6 and 7

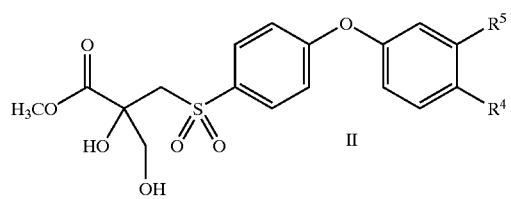

144
-continued

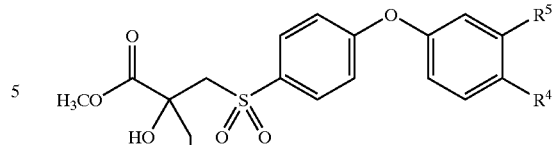

1. NH₂OH(aq)
2. HCl

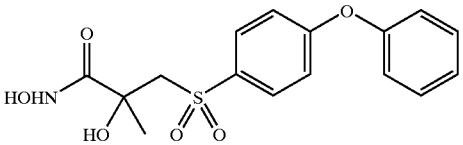

Example 3, R⁴ = R⁵ = H
Example 7, R⁴ = R⁵ = CH₃

Best Mode for Carrying Out The Invention

Without further elaboration, it is believed that one skilled in the art can, using the preceding description, utilize the present invention to its fullest extent. The following preferred specific embodiments are, therefore, to be construed as merely illustrative, and not limiting of the remainder of the disclosure in any way whatsoever.

EXAMPLE 1

Preparation of N,2-dihydroxy-2-methyl-3-[(4-phenoxyhenyl)sulfonyl]propanamide

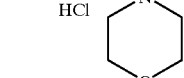

Part A: To a flask equipped with an overhead stirrer powdered potassium hydroxide (114.24 g, 2.04 mol) was added to methanol (1L) over 10 minutes. The solution was cooled to zero degrees celsius on an ice bath and methyl 2-methylglycidate (99.2 g, 0.85 mol) in methanol (40 mL) was added over 15 minutes. A precipitate formed upon warming to ambient temperature. After 30 minutes the mixture was cooled to 5° C. and 4-(phenoxy)-benzenethiol (151.73 g, 0.75 mol) was added dropwise over 10 minutes. The mixture was warmed to ambient temperature. After 24 hours the solvent was removed in vacuo. The residue was dissolved into ethyl acetate and washed with 3M HCl, and saturated NaCl.

Concentration in vacuo Afforded the Sulfide as a Solid (256.36 g, Quantitative Yield).

Part B: A solution of the crude sulfide of Part A (256.3 g, 0.75 mol theoretical) was divided into 3 equal portions. One third (0.25 mol) was dissolved in THF (1710 mL) and H$_2$O (190 mL). To this solution was added Oxone® (474 g, 0.77 mol) and the mixture stirred for 1.25 hours. The excess Oxone® was removed by filtration and the filtrate was concentrated in vacuo. This procedure was repeated 2 times and the product was combined and dissolved into ethyl acetate, washed with H$_2$O and dried over Na$_2$SO$_4$. After concentration in vacuo to 30% volume, the solution was poured into hexanes. The resulting solid was collected by vacuum filtration. Recrystallization with ethyl acetate/hexanes provided the sulfone as a white solid (207 g, 83%).

Part C: To a solution of the sulfone of Part B (153.35 g, 455.90 mmol) and N-hydroxybenzotriazole·H$_2$O (73.86 g, 547.08 mmol) in DMF (1.5 L) was added 1-(3-dimethylaminopropyl)-3-ethylcarbodiimide hydrochloride (96.14 g, 501.49 mmol). After stirring at ambient temperature for 1 hour, the solution was cooled to 8° C. and NH$_2$OH$_{(aq)}$ (50%, 81 mL, 1.37 mol) was added gradually. After 30 minutes at ambient temperature, the DMF was removed in vacua. The residue was dissolved into ethyl acetate and washed with H$_2$O and saturated NaCl, and dried over Na$_2$SO$_4$. Recrystallization with hot acetone and hexanes provided the title compound as a white solid (90 g, 56%). HRMS calculated for C$_{16}$H$_{17}$NO$_6$S: 352.0855, found 352.0834.

EXAMPLE 1A (S) —N,2-dihydroxy-2-methyl-3-[(4-phenoxyphenyl)sulfonyl]propanamide

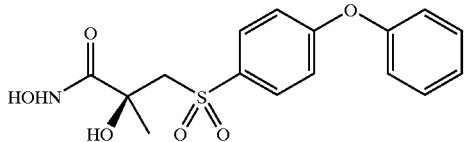

A solution of N,2-dihydroxy-2-methyl-3-[(4-phenoxyphenyl)sulfonyl]propanamide (20 g) in ethanol (1500 mL) was sequentially injected in 12 mL portions onto a Prochrom® column (50 mm I.D., 36 mm bed length) packed with Chiralpak® AD. The mobile phase used was 30% isopropyl alcohol/70% heptane. Fractions were collected automatically and pooled. The first eluting peak was collected and the appropriate fractions were combined to provide the title compound (8.351 g). HPLC purity: 100%.

EXAMPLE 1B

Preparation of (R) —N,2-dihydroxy-2-methyl-3-[(4-phenoxyphenyl)sulfonyl]-propanamide

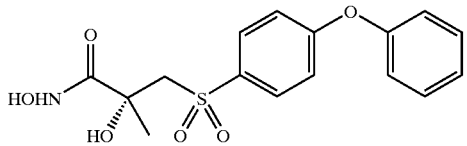

A solution of N,2-dihydroxy-2-methyl-3-[(4-phenoxyphenyl)sulfonyl]propanamide (20 g) in ethanol (1500 mL) was sequentially injected in 12 mL portions onto a Prochrom column (50 mm I.D., 36 mm bed length) packed with Chiralpak AD. The mobile phase used was 30% isopropyl alcohol/70% heptane. Fractions were collected automatically and pooled. The second eluting peak was collected and the appropriate fractions were combined to provide the title compound (8.176 g). HPLC purity: 92%.

EXAMPLE 2

Preparation of N,2-dihydroxy-2-(hydroxymethyl)-3-[(4-phenoxyphenyl)-sulfonyl]propanamide

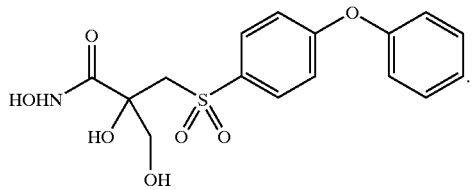

Part A: To a solution of methyl 2-(bromomethyl) acrylate (9.90 g, 55.3 mmol) and 4-(phenoxy)-benzenethiol (11.7 g, 57.9 mmol) in acetonitrile (70 mL) was added K$_2$CO$_3$ (7.50 g, 54.3 mmol). After stirring at ambient temperature for 1 hour the solution was concentrated in vacuo to half volume and partitioned between ethyl acetate and H$_2$O. The organic layer was dried over MgSO$_4$. Concentration in vacuo provided a yellow liquid. A solution of the crude liquid in methanol (100 mL) was added to a mixture of Oxone® (100 g) in methanol (150 mL) and H$_2$O (25 mL). After 1 hour the solution was concentrated and partitioned between ethyl acetate and H$_2$O. The organic layer was washed with H$_2$O and dried over MgSO$_4$. Concentration in vacuo provided a thick oil and recrystallization with hot ethyl ether provided the sulfone as a white solid (13.3 g, 73%).

Part B: To a solution of 4-methylmorpholine N-oxide (10 g, 85 mmol) in 8:1 acetone/water (50 mL) was added osmium tetroxide (2.5% in t-butanol, 25 mL, 2.0 mmol) followed by the, acrylate of Part A (13.3 g, 40.1 mmol) in 8:1 acetone/water (80 mL). After stirring at ambient temperature for 20 hours, Na$_2$SO$_3$ (5 g) was added and stirring continued for 1 hour. Concentration in vacuo was followed by partitioning between ethyl acetate and H$_2$O. The organic layer was washed with saturated NaCl. Elution through a silica pad (ethyl acetate) followed by concentration provided the diol as a white solid (15 g, quantatitive yield). HRMS calculated for C$_{17}$H$_{18}$O$_7$S: 367.0852, found 367.0868.

Part C: To a solution of the diol of Part B (2.5 g, 6.8 mmol) in THF (20 mL) and methanol (20 mL) was added NH$_2$OH$_{(aq)}$ (50%, 9.0 mL, 138 mmol). After stirring at ambient temperature for 72 hours, additional NH$_2$OH$_{(aq)}$ (10 mL) was added and stirring continued for 72 hours. The solution was concentrated in vacuo and the residue was partitioned between ethyl acetate and H$_2$O. The organic layer was washed with saturated NaCl. The resulting suspension was concentrated in vacuo to a minimal volume and filtration provided the title compound as a white solid (1.7 g, 68%). HRMS calculated for C$_{16}$H$_{17}$NO$_7$S: 368.0804, found: 368.0759.

EXAMPLE 3

Preparation of N,α-dihydroxy-α-[[(4-phenoxyphenyl)sulfonyl]methyl]-4-morpholinepranamide, monohydroloride

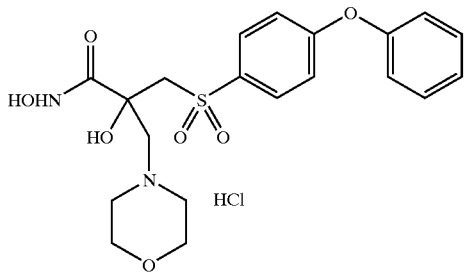

Part A: To a solution of methyl 2-(bromomethyl) acrylate (9.90 g, 55.3 mmol) and 4-(phenoxy)-benzenethiol (11.7 g, 57.9 mmol) in acetonitrile (70 mL) was added $K_2CO_3$ (7.50 g, 54.3 mmol). After stirring at ambient temperature for 1 hour the solution was concentrated in vacuo to half volume and partitioned between ethyl acetate and $H_2O$. The organic layer was dried over $MgSO_4$. Concentration in vacuo provided a yellow liquid. A solution of the crude liquid in methanol (100 mL) was added to a mixture of Oxone® (100 g) in methanol (150 mL) and $H_2O$ (25 mL). After 1 hour the solution was concentrated and partitioned between ethyl acetate and $H_2O$. The organic layer was washed with $H_2O$ and dried over $MgSO_4$. Concentration in vacuo provided a thick oil and recrystallization with hot ethyl ether provided the sulfone as a white solid (13.3 g, 73%).

Part B: To a solution of 4-methylmorpholine N-oxide (10 g, 85 mmol) in 8:1 acetone/water (50 mL) was added osmium tetroxide (2.5% in t-butanol, 25 mL, 2.0 mmol) followed by the sulfone of Part A (13.3 g, 40.1 mmol) in 8:1 acetone/water (80 mL). After stirring at ambient temperature for 20 hours, $Na_2SO_3$ (5 g) was added and stirring continued for 1 hour. After partitioning between ethyl acetate and $H_2O$, the organic phase was concentrated in vacuo. The organic layer was washed with saturated NaCl. Elution through a silica pad (ethyl acetate) followed by concentration provided the diol as a white solid (15 g, quantatitive yield).

Part C: To a solution of the diol of Part B (5.48 g, 15.0 mmol) in dichloromethane (70 mL), cooled to −78° C., was added pyridine (1.35 mL, 16.7 mmol) followed by the slow addition of trifluoromethanesulfonic anhydride (2.71 mL, 16.1 mmol). After stirring for 30 minutes at −78° C., the solution was returned to ambient temperature and stirred for 3 hours. The solution was concentrated in vacuo and partitioned between ethyl acetate and 1M citric acid. The organic layer was washed with saturated NaCl, dried over $MgSO_4$, and concentrated in vacuo. The crude material was chromatographed on silica gel to obtain a 65:35 mixture of the epoxide and trif late, which was carried on to next step without additional purification.

Part D: To a solution of the mixture of epoxide/triflate of Part C (15.0 mmol) in methanol (30 ML) cooled to zero degrees C, was added morpholine (3.9 mL, 45.0 mmol). The solution was warmed and stirred at ambient temperature for 1.5 hours. The solvent was concentrated in vacuo and the residue was dissolved into ethyl acetate and washed with $H_2O$ and saturated NaCl. Concentration in vacuo provided a yellow, oily foam which was dissolved into acetonitrile and concentrated HCl (1 mL) was added. Concentration in vacuo followed by trituration with ethyl ether provided the HCl salt of the morpholine methyl ester compound as a white solid (4.2 g, 60%). HPLC purity: >98%.

Part E: To a solution of the methyl ester of Part D (4.1 g, 8.74 mmol) in THF (45 mL) and methanol (45 mL) was added $NH_2OH_{(aq)}$ (50%, 5 mL, 67.6 mmol) the mixture stirred for 72 hours. The solution was concentrated to 25% original volume and partitioned between ethyl acetate and $H_2O$. The organic layer was washed with saturated NaCl, dried over $MgSO_4$ and concentrated in vacuo. The resulting oil was triturated with ethyl acetate/ethyl ether to give a white solid. The HCl salt was formed by adding HCl (concentrated, 1 mL) to a solution of the free base in acetonitrile (40 mL). Concentration in vacuo followed by trituration with THF and methanol provided the title compound as a white solid (2.2 g, 53%).

EXAMPLE 4

3-[[4-(3,4-dimethylphenoxy)phenyl]-sulfonyl]-N,2-dihydroxy-2-(hydroxymethyl) propanamide

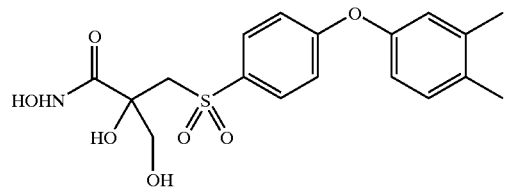

Part A: To a solution of 4-fluoroacetophenone (27.63 g, 0.20 mol) and 3,4-dimethylphenol (24.43 g, 0.20 mol) in dimethylacetamide (200 mL) was added $K_2CO_3$ (33.17 g, 0.24 mol) and the mixture was heated at reflux for 8 hours. After concentration of solvent, the residue was dissolved in ethyl acetate (400 mL) and washed with $H_2O$ (200 mL), 1N HCl (200 mL) and saturated NaCl (200 mL) and dried over $Na_2SO_4$. Recrystallization from hot ethyl acetate/hexanes provided the acetophenone as a solid (28.5 g, 59%). HPLC purity: 99%.

Part B: To a solution of the acetophenone of part A (26.04 g, 108.4 mmol) in methanol (590 mL) and $H_2O$(65 mL) was added Oxone® (133 g, 216.7 mmol). The mixture was heated at reflux for 5.5 hours and after cooling to ambient temperature, the excess Oxone® was removed by filtration and was washed with methanol. After concentration of solvent, the residue was dissolved in ethyl acetate (400 mL) and washed with $H_2O$ (300 mL) and dried over $Na_2SO_4$. Purification by chromatography (10% ethyl acetate/hexanes to 20% ethyl acetate/hexanes) provided the phenol as a solid (13.98 g, 60%). HPLC purity: >99%. MS(CI) $MH^+$ calculated for $C_{14}H_{14}O_2$: 215, found 215.

Part C: To a solution of KOH (8 g, 143 mmol) in H2O (85 mL), cooled to zero degrees C, was added the phenol of Part B (13.7 g, 64.0 mmol) followed by the dropwise addition of dimethylthiocarbamoyl chloride (10.6 g, 85.8 mmol) in THF (75 mL). The solution stirred for 4.5 hours at zero degrees C followed by extraction with toluene (2×125 mL). The organic layers were combined and dried over $MgSO_4$. Purification by chromatography (95:5 hexane/ethyl acetate with 1% triethylamine) provided the thiocarbamate as a white solid (10.9 g, 56%). HPLC purity: >99%.

Part D: The thiocarbamate of Part C (10.9 g, 53.6 mmol) was heated to 290° C. for 15 minutes. The compound was cooled to ambient temperature and dissolved into an 8:1 mixture of ethylene glycol/$H_2O$. Added to this solution was added KOH (9.0 g, 161 mmol) and the mixture was stirred for 1.5 hours. The mixture was poured over ice (125 g) and concentrated HCl (6 mL) was added. The mixture was extracted with chloroform (1×100 mL) and dichloromethane (2×60 mL) and the combined organic layers were dried over $MgSO_4$. Purification by chromatography (hexane) provided the thiophenol as a colorless liquid (4.0 g, 32%).

Part E: To a solution of the thiophenol of Part D (2.2 g, 9.48 mmol) and 2-(bromomethyl)acrylic acid (1.56 g, 9.45 mmol) in acetonitrile (40 mL) was added $K_2CO_3$ (2.6 g, 18.8 mmol). After stirring for 1 hour, the solvent was removed in vacuo and the residue was partitioned between ethyl acetate and 1N HCl. The organic layer was dried over $MgO_4$ and concentrated in vacuo. The crude solid was dissolved in methanol (100 mL) and $H_2O$ (8 mL) and Oxone® (16 g, 28.4 mmol) was added. After 90 minutes the reaction mixture was filtered to collect excess Oxone® and the filtrate was concentrated in vacuo. The residue was partitioned between ethyl acetate and $H_2O$ and the organic layer was washed with saturated NaCl and dried over $MgSO_4$. Concentration in vacuo provided the sulfone as a white solid (2.85 g, 86%).

Part F: To a solution of the sulfone of Part E (2.83 g, 8.1 mmol) and 4-methylmorpholine N-oxide (1.9 g, 16.2 mmol) in 8:1 acetone/$H_2O$ (45 mL) was added osmium tetroxide (2.5% in t-butanol, 5 mL, 0.4 mmol) and the solution stirred for 1.5 hours at ambient temperature. The solvent was removed in vacua and the residue was dissolved in ethyl acetate and acidified with 1N HCl. The aqueous layer was extracted with ethyl acetate twice and the combined organic layers were washed with $H_2O$ and saturated NaCl and dried over $MgSO_4$. Concentration in vacuo followed by trituration with ethyl ether provided the diol as an off white solid (2.5 g, 81%).

Part G: To a solution of the diol of Part F (2.4 g, 6.3 mmol) and N-hydroxybenzotriazole·$H_2O$ (1.1 g, 8.2 mmol) in DMF (25 mL) was added 1-(3-dimethylamino-propyl)3-ethylcarbodiimide hydrochloride(1.3 g, 6.9 mmol). After 1 hour of stirring at ambient temperature, $NH_2OH_{(aq)}$ (50%, 1.25 mL, 21.7 mmol) was added. After 40 minutes the solution was concentrated in vacuo and the residue was partitioned between ethyl acetate and $H_2O$. The organic layer was dried over $MgSO_4$. Trituration with a combination of ethyl ether, isopropanol, methanol and THF provided the title compound as a white solid (750 mg, 30%). HMS calculated for $C_{18}H_{21}NO_7S$: 396.1117, found 396.1125.

EXAMPLE 5

3-[[4-(3,4-dimethylphenoxy)phenyl]-sulfonyl]-N,2-dihydroxy-2-methylpropanamide

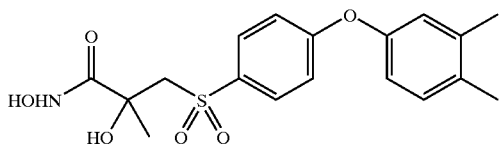

Part A: To a solution of 4-fluoroacetophenone (27.63 g, 0.20 mol) and 3,4-dimethylphenol (24.43 g, 0.20 mol) in dimethylacetamide (200 mL) was added $K_2CO_3$ (33.17 g, 0.24 mol) and the mixture was heated at reflux for 8 hours. After concentration of solvent the residue was dissolved in ethyl acetate (400 mL) and $H_2O$ (200 mL), washed with 1N HCl (200 mL) and saturated NaCl (200 mL) and dried over $Na_2SO_4$. Recrystallization from hot ethyl acetate/hexanes provided the acetophenone as a solid (28.5 g, 59%). HPLC purity: 99%.

Part B: To a solution of the acetophenone of part A (26.04 g, 108.4 mmol) in methanol (590 mL) and $H_2O$ (65 mL) was added Oxone® (133 g, 216.7 mmol). The mixture was heated at reflux for 5.5 hours and after cooling to ambient temperature, the excess Oxone® was removed by filtration and was washed with methanol. After concentration of the methanol the residue was dissolved in ethyl acetate (400 mL) and washed with $H_2O$ (300 mL) and dried over $Na_2SO_4$. Purification by chromatography (10% ethyl acetate/hexanes to 20% ethyl acetate/hexanes) provided the phenol as a solid (13.98 g, 60%). HPLC purity: >99%. MS(CI) $MH^+$ calculated for $C_{14}H_{14}O_2$: 215, found: 215.

Part C: To a solution of KOH (8 g, 143 mmol) in $H_2O$ (85 mL), cooled to zero degrees C, was added the phenol of Part B (13.7 g, 64.0 mmol) followed by the dropwise addition of dimethylthiocarbamoyl chloride (10.6 g, 85.8 mmol) in THF (75 mL). The solution stirred for 4.5 hours at zero degrees C followed by extraction with toluene (2×125 mL). The organic layers were combined and dried over $MgSO_4$. Purification by chromatography (95:5 hexane/ethyl acetate with 1% triethylamine) provided the thiocarbamate as a white solid (10.9 g, 56%). HPLC purity: >99%.

Part D: The thiocarbamate of Part C (10.9 g, 53.6 mmol) was heated to 290° C. for 15 minutes. The compound was cooled to ambient temperature and dissolved into an 8:1 mixture of ethylene glycol/$H_2O$. Added to this solution was KOH (9.0 g, 161 mmol) and the mixture stirred for 1.5 hours. The mixture was poured over ice (125 g) and concentrated HCl (6 mL) was added. The mixture was extracted with chloroform (1×100 mL) and dichloromethane (2×60 mL) and the combined organic layers were dried over $MgSO_4$. Purification by chromatography (hexane) provided the thiol as a colorless liquid (4.0 g, 32%).

Part E: To a solution of KOH (1.14 g, 20.4 mmol) in methanol (10 mL) cooled to zero degrees C was added methyl 2-methylglycidate (0.9 mL, 8.5 mmol). The solution was warmed and stirred for 30 minutes at ambient temperature. The solution was again cooled to zero degrees C and added to it was the thiol of Part D (1.78 g, 7.73 mmol). The solution stirred for 24 hours at ambient temperature. After concentration to remove solvent, the residue was dissolved into ethyl acetate and acidified with 1N HCl. The organic layer was washed with saturated NaCl and dried over $Na_2SO_4$. Concentration in vacuo provided the sulfide as a solid (3.2 g, quantitative yield). HPLC purity: 99%.

Part F: To a solution of the sulfide of Part E (2.6 g, 7.8 mmol) in THF (59 mL) and $H_2O$ (6 mL) was added Oxone® (14.4 g, 23.5 mmol) and the mixture stirred for 1 hour. The excess Oxone® was collected by filtration and washed with THF. The filtrate was concentrated and the residue was dissolved in ethyl acetate, washed with $H_2O$ and dried over $Na_2SO_4$. Concentration in vacuo provided the sulfone as a solid (2.83 g, quantitative yield). HPLC purity: 99%. MS(CI) $MH^+$ calculated for $C_{18}H_{20}O_6S$: 365, found 365.

Part G: To a solution of the acid of Part F (2.74 g, 7.52 mmol) and N-hydroxybenzotriazole·$H_2O$ (1.22 g, 9.02 mmol) in DMF (25 mL) was added 1-(3-dimethylamino-propyl)3-ethylcarbodiimide hydrochloride (1.59 g, 8.27 mmol). After stirring at ambient temperature for 1 hour, $NH_2OH$ (a) (50%, 1.3 mL, 22.56 mmol) was added. After 15 minutes the solvent was removed in vacuo and the residue was dissolved in ethyl acetate, washed with $H_2O$ and saturated NaCl, and dried over $Na_2SO_4$. Recrystallization with hot acetone/hexane provided the title compound as a white powder (1.35 g, 47%). HPLC purity: 99%. MS(CI) $MH^+$ calculated for $C_{18}H_{21}NO_6S$: 380, found 380.

EXAMPLE 6

N,2-dihydroxy-2-(methoxymethyl)-3-[(4-phenoxyphenyl)sulfonyl]propanamide

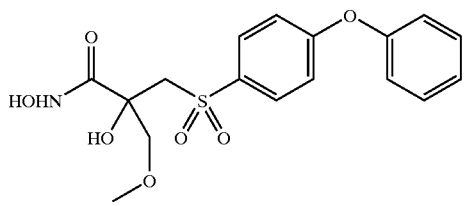

Part A: To a solution of methyl 2-(bromomethyl) acrylate (9.90 g, 55.3 mmol) and 4-(phenoxy)benzenethiol (11.7 g, 57.9 mmol) in acetonitrile (70 mL) was added $K_2CO_3$ (7.50 g, 54.3 mmol). After stirring at ambient temperature for 1 hour the solution was concentrated in vacuo to half volume and partitioned between ethyl acetate and $H_2O$. The organic layer was dried over $MgSO_4$. Concentration in vacuo provided a yellow liquid. A solution of the crude liquid in methanol (100 mL) was added to Oxone® (100 g) in a mixture of methanol (150 mL) and $H_2O$ (25 mL). After 1 hour, the solution was concentrated and partitioned between ethyl acetate and $H_2O$. The organic layer was washed with $H_2O$ and dried over $MgSO_4$. Concentration in vacuo provided a thick oil, and recrystallization with hot ethyl ether provided the sulfone as a white solid (13.3 g, 73%).

Part B: To a solution of 4-methylmorpholine N-oxide (10 g, 85 mmol) in 8:1 acetone/water (50 mL) was added osmium tetroxide (2.5% in t-butanol, 25%, 2.0 mmol) followed by the acrylate of Part A (13.3 g, 40.1 mmol) in 8:1 acetone/water (80 mL). After stirring at ambient temperature for 20 hours, $Na_2SO_3$ (5 g) was added and stirring continued for 1 hour. Concentration in vacuo was followed by partitioning between ethyl acetate and $H_2O$. The organic layer was washed with saturated NaCl. Elution through a silica pad (ethyl acetate) followed by concentration provided the diol as a white solid (15 g, quantatitive yield).

Part C: To a solution of the methyl ester of Part B (535 mg, 1.46 mmol) in DMF (20 mL), cooled to zero degrees C, was added NaH (66 mg, 4.7 mmol). After stirring for 5 minutes, iodomethane (505 mg, 8.14 mmol) was added. After stirring for 70 minutes, the solution was purified via flash chromatography (50/50 ethyl acetate/hexanes to 100 ethyl acetate) providing the methyl ether as a foam (262 mg, 47%).

Part D: To a solution of the methyl ester of Part C (260 mg, 0.68 mmol) in THF (1.5 mL) and methanol (1.5 mL) was added $NH_2OH_{(aq)}$ (50%, 1 mL, 13.6 mmol) and the solution stirred for 20 hours at ambient temperature. An additional 1.5 mL of $NH_2OH_{(aq)}$ were added and the solution stirred for 96 hours. The solution was partitioned between ethyl acetate and $H_2O$, the organic was dried over $MgSO_4$ and concentrated in vacua to give the title compound as a foam (20 mg, 8%).

EXAMPLE 7

α-[[[4-(3,4-dimethylphenoxy)-phenyl)-sulfonyl]methyl]-N-2-dihydroxy-4-morpholinepropanamide

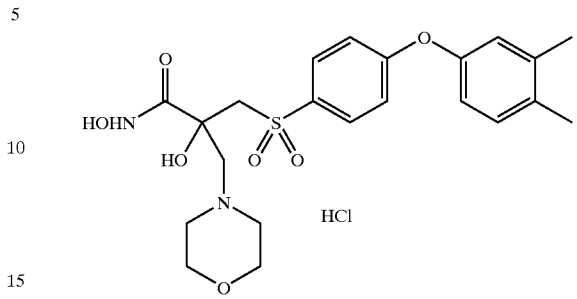

Part A: To a solution of 4-fluoroacetophenone (27.63 g, 0.20 mol) and 3,4-dimethylphenol (24.43 g, 0.20 mol) in dimethylacetamide (200 mL) was added $K_2CO_3$ (33.17 g, 0.24 mol) and the mixture heated at reflux for 8 hours. After concentration of solvent the residue was dissolved in ethyl acetate (400 mL) and $H_2O$ (200 mL), washed with 1N HCl (200 mL) and saturated NaCl (200 mL) and dried over $Na_2SO_4$. Recrystallization from hot ethyl acetate/hexanes provided the acetophenone as a solid (28.5 g, 59%). HPLC purity: 99%.

Part B: To a solution of the acetophenone of part A (26.04 g, 108.4 mmol) in methanol (590 mL) and $H_2O$ (65 mL) was added Oxone® (133 g, 216.7 mmol). The mixture was heated at reflux for 5.5 hours and after cooling to ambient temperature, the excess Oxone® was removed by filtration and was washed with methanol. After concentration of solvent, the residue was dissolved in ethyl acetate (400 mL) and washed with $H_2O$ (300 mL) and dried over $Na_2SO_4$. Purification by chromatography (10% ethyl acetate/hexanes to 20% ethyl acetate/hexanes) provided the phenol as a solid (13.98 g, 60%). HPLC purity: >99%. MS(CI) $MH^+$ calculated for $C_{14}H_{14}O_2$: 215, found: 215.

Part C: To a solution of KOH (8 g, 143 mmol) in $H_2O$ (85 mL), cooled to zero degrees C, was added the phenol of Part B (13.7 g, 64.0 mmol) followed by the dropwise addition of dimethylthiocarbamoyl chloride (10.6 g, 85.8 mmol) in THF (75 mL). The solution was stirred for 4.5 hours at zero degrees C followed by extraction with toluene (2×125 mL). The organic layers were combined and dried over $MgSO_4$. Purification by chromatography (95:5 hexane/ethyl acetate with 1% triethylamine) provided the thiocarbamate as a white solid (10.9 g, 56%). HPLC purity: >99%.

Part D: The thiocarbamate of Part C (10.9 g, 53.6 mmol) was heated to 290° C. for 15 minutes. The compound was cooled to ambient temperature and dissolved into an 8:1 mixture of ethylene glycol/$H_2O$. Added to this solution was KOH (9.0 g, 161 mmol) and the mixture was stirred for 1.5 hours. The mixture was poured over ice (125 g) and concentrated HCl (6 mL) was added. The mixture was extracted with chloroform (1×100 mL) and dichloromethane (2×60 mL) and the combined organic layers were dried over $MgSO_4$. Purification by chromatography (hexane) provided the thiophenol as a colorless liquid (4.0 g, 32%).

Part E: To a solution of the thiophenol of Part D (2.2 g, 9.48 mmol) and 2-(bromomethyl)acrylic acid (1.56 g, 9.45 mmol) in acetonitrile (40 mL) was added $K_2CO_3$ (2.6 g, 18.8 mmol). After stirring for 1 hour, the solvent was removed in vacuo and the residue was partitioned between ethyl acetate and 1N HCl. The organic layer was dried over $MgSO_4$ and concentrated in vacuo. The crude solid was dissolved in methanol (100 mL) and H₂O (8 mL) and Oxone® (16 g, 28.4 mmol) was added. After 90 minutes, the reaction mixture was filtered to collect excess Oxone® and the filtrate was concentrated in vacua. The residue was partitioned between ethyl acetate and H₂O, the organic layer was washed with saturated NaCl and dried over MgSO₄. Concentration in vacuo provided the sulfone as a white solid (2.85 g, 92%).

Part F: To a solution of the sulfone of Part E (45.0 g, 129.9 mmol) in methanol (600 mL) was added thionyl chloride (19 mL, 259.8 mmol) dropwise. The solution was heated at reflux for 3 hours. The solution was concentrated in vacua and the residue was partitioned between ethyl acetate and saturated NaHCO₃. The aqueous solution was extracted once with ethyl acetate and the organic layers were combined and washed with saturated NaCl and dried over MgSO₄. Concentration in vacua provided the methyl ester as a tan oil (45.8 g, 98%). Compound carried on to next step without additional purification. HPLC purity: 92%.

Part G: To a solution of 4-methylmorpholine N-oxide (29.3 g, 249.71 mmol) in 8:1 acetone/H₂O (100 mL) was added osmium tetroxide (2.5% in t-butanol, 15.65 mL, 1.25 mmol) followed by the dropwise addition of the methyl ester of Part F (45.0 g, 125 mmol) in 8:1 acetone/H₂O. The solution stirred for 1 hour at ambient temperature. To the mixture is added Na₂CO₃ (16 g) and stirring continued for 30 minutes. The solution was concentrated in vacuo and the residue was partitioned between ethyl acetate/H₂O. The aqueous layer was extracted once with ethyl acetate and the organic layers were combined, washed with brine, and dried over MgSO₄. Purification by chromatography (ethyl acetate/hexane) provided the diol as a white solid (41.6 g, 85).

Part H: To a solution of the diol of Part G (3.0 g, 7.61 mmol) in dichloromethane (38 mL) cooled to −71° C. was added pyridine (0.69 mL, 8.52 mmol) followed by the slow addition of triflic anhydride (1.4 mL, 7.99 mmol). The solution stirred at −71° C. for 25 minutes. Additional pyridine (69 mL, 8.52 mmol) and trifluoromethanesulfonic anhydride (1.4 mL, 7.99 mmol) were added and the solution stirred for 1 hour. The solution was partitioned between ethyl acetate and citric acid (5%). The organic layer was washed with saturated NaCl and dried over Na₂SO₄. Concentration in vacuo provided the triflate as an oil (4.27 g, quantitative yield).

Part I: To a solution of the triflate of Part H (4.27 g, 8.11 mmol) in THF (15 mL), cooled to zero degrees C, was added morpholine (2.1 mL, 24.33 mmol). The solution stirred at ambient temperature for 1.5 hours. The solvent was removed in vacuo and the residue was dissolved into ethyl acetate and washed with saturated NaHCO₃, saturated NaCl and dried over Na₂SO₄. After concentration, the residue was dissolved in acetonitrile and acidified with concentrated HCl. Trituration with ethyl ether provided the ethyl morpholine compound as a white solid (2.95 g, 73%).

Part J: To a solution of the ethyl morpholine of Part I (2.95 g, 5.89 mmol) in 1:1 THF/methanol (14 mL) was added NH₂OH$_{(aq)}$ (50%, 7 mL, 118 mmol). After stirring at ambient temperature for 20 hours additional NH₂OH$_{(aq)}$ (7 mL) was added and the solution stirred for an additional 24 hours. After concentration in vacuo the residue was dissolved into ethyl acetate and washed with saturated NaHCO₃, H₂O, and saturated NaCl and dried over Na₂SO₄. The solution was acidified with concentrated HCl and trituration with ethyl ether provided a crude solid. Recrystallization with hot THF and ethyl ether provided α-[[[4-(3,4-dimethylphenoxy)-phenyl]sulfonyl]methyl]-N-2 -dihydroxy-4-morpholine-propanamide as a white solid (1.5 g, 51%). HPLC purity: 98%. MS(CI) MH⁺ calculated for C₂₂H₂₈N₂O₇·HCl: 465, found: 465.

EXAMPLE 8

N,2-dihydroxy-3-[(4-methoxyphenyl) sulfonyl]propanamide

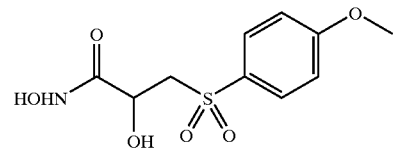

Part A: To a solution of β-chlorolactic acid (2.0 g, 16.1 mmol) in DMF (45 mL) was added 4-methoxy-benzenethiol (2.0 mL, 16.1 mmol) and K₂CO₃ (4.4 g, 31.8 mmol) and the solution was stirred for 1 hour at ambient temperature. The solution was concentrated in vacuo and the residue was partitioned between ethyl acetate and 1N HCl. The organic layer was dried over MgSO₄ and concentrated in vacuo. To a solution of the crude sulfide in methanol (100 mL) and H₂O (5 mL) was added Oxone® (30 g, 48.3 mmol) and the mixture was stirred for 18 hours at ambient temperature. The mixture was filtered and the filtrate was acidified to pH=7 with aqueous K₂CO₃. The solution was partitioned between ethyl acetate and H₂O and the organic layer was washed with saturated NaCl, dried over MgSO₄ and concentrated in vacuo. Chromatography (ethyl acetate/hexane) provided the sulfone methyl ester as a clear, colorless oil (2.3 g, 52%).

Part B: To a solution of the sulfone of part A (2.3 g, 8.4 mmol) in methanol (25 mL) and THF (25 mL) was added 50% aqueous hydroxylamine (5.7 mL, 84 mmol) and the solution was stirred for 1 hour. The solution was diluted with ethyl acetate and concentration in vacuo provided N,2-dihydroxy-3-[(4-methoxyphenyl)-sulfonyl]propanamide as a white powder (1.75 g, 76%). HPLC purity: >99%. HRMS calculated for C₁₀H₁₃NO₆S: 276.0542, found: 276.0546.

EXAMPLE 9

N,2-dihydroxy-3-[(4-phenoxyphenyl) sulfonyl]propanamide

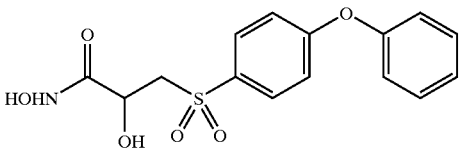

Part A: To a solution of β-chlorolactic acid (10.0 g, 80.3 mmol) in DMF (85 mL) was added 4-fluorothiophenol (10.3 g, 80.3 mmol) and K₂CO₃ (22 g, 16 mmol) and the solution was stirred for 1 hour at ambient temperature. The solution was concentrated in vacuo and the residue was partitioned between ethyl acetate and 1N HCl. The sulfide-containing organic layer was dried over MgSO₄ and concentrated in vacuo. To a solution of the crude sulfide in methanol (250 mL) and H₂O (100 mL) was added Oxone® (149 g, 240 mmol) and the mixture was stirred for 6 hours at ambient temperature. The mixture was filtered, the filtrate was concentrated and trituration with ethyl ether provided the sulfone as a white solid (19 g, 91%).

Part B: To a solution of the sulfone of part A (1.0 g, 4.3 mmol) in DMF (45 mL) was added phenol (633 mg, 6.45 mmol) and $K_2CO_3$ (1.8 g, 12.9 mmol) and the solution was heated at 60° C. for 18 hours. The solution was concentrated in vacuo and the residue was dissolved into methanol and HCl gas was bubbled into the solution to form the methyl ester. Concentration in vacua provided the methyl ester as a white solid (630 mg, 43%).

Part C: To a solution of the methyl ester of part B (630 mg, 1.9 mmol) in methanol (4 mL) and THF (4 mL) was added 50% aqueous hydroxylamine (1.4 mL, 19 mmol) and the solution stirred for 18 hours. The solution was concentrated in vacuo and the residue was partitioned between ethyl acetate and aqueous $KHSO_4$. The organic layer was washed with saturated NaCl and dried over $MgSO_4$. Chromatography (ethyl acetate/methanol) provided N,2-dihydroxy-3-[(4-phenoxyphenyl)sulfonyl]propanamide as white solid (250 mg, 40%). HPLC purity: >97%. HRMS calculated for $C_{15}H_{15}NO_6S$: 338.0698, found: 338.0678.

EXAMPLE 10

(R) N,2-dihydroxy-3-[(4-phenoxyphenyl)-sulfonyl]propanamide

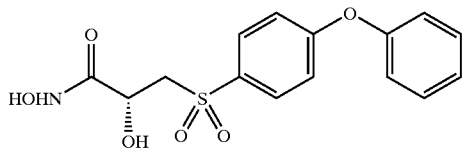

Part A: To a solution of D-serine (25.0 g, 237.9 mmol) in 6N HCl (300 mL) cooled to zero degrees C was added sodium nitrite (19.0 g, 275 mmol) and the solution was stirred for 3.5 hours. The solution was extracted with ethyl ether and the combined chloro compound-containing organic layers were dried over $Na_2SO_4$. Concentration in vacuo provided the chloro compound as a yellow oil (15.2 g, 51%).

Part B: To a solution of the chloro compound of part A (15.2 g, 122.1 mmol) in ethanol (75 mL) cooled to zero degrees C was added crushed KOH (13.7 g, 244.13 mmol). The solution stirred for 18 hours at ambient temperature. The reaction was filtered and the filtrate was concentrated in vacuo to provide the epoxide as a light yellow solid (11.9 g, 77%).

Part C: To a solution of 4-(phenoxy)benzenethiol (4.0 g, 19.8 mmol) in methanol (35 mL) cooled to zero degrees C was added the epoxide of part B (2.5 g, 19.8 mmol) followed by sodium methoxide (preformed with 500 mg sodium in 50 mL methanol). The solution was heated at 40° C. for 24 hours. The solution was concentrated in vacua and the residue was partitioned between ethyl acetate and 1N HCl. The organic layer was washed with saturated NaCl nd dried over $MgSO_4$. Concentration in vacuo provided he crude sulfide as a tan solid (5.7 g).

Part D: To a solution of the sulfide of part C (5.7 g, 19.7 mmol) in methanol (100 mL) was added thionyl chloride (2.9 mL, 39.3 mmol) and the solution was heated at reflux for 1 hour. The solution was concentrated in vacuo and the residue was partitioned between ethyl acetate and saturated $NaHCO_3$. The aqueous layer was extracted with ethyl acetate and the combined organic layers were washed with saturated NaCl and dried over $MgSO_4$. Chromatography (ethyl acetate/hexane) provided the methyl ester as a colorless oil (3.8 g, 63%).

Part E: To a solution of the sulfide of part D (3.76 g, 12.3 mmol) in methanol (90 mL) and $H_2O$ (10 mL) was added Oxone® (26.6 g, 43.2 mmol) and the solution was stirred for 18 hours at ambient temperature. The mixture was filtered and the filtrate was concentrated in vacuo. The residue was partitioned between ethyl acetate and $H_2O$. The aqueous layer was extracted with ethyl acetate and the combined organic layers were washed with saturated NaCl and dried over $MgSO_4$. Concentration in vacuo provided the sulfone as a white solid (3.9 g, 93%).

Part F: To a solution of the sulfone of part E (3.9 g, 11.6 mmol) in methanol (20 mL) and THF (20 mL) was added 50% aqueous hydroxylamine (14 mL). The solution was stirred for 18 hours at ambient temperature. The solution was concentrated in vacuo and recrystallization (acetone/$H_2O$) provided (R)-N,2-dihydroxy-3-[(4-phenoxyphenyl)sulfonyl]propanamide as a white solid (2.6 g, 67%). HPLC purity: 99%. HRMS calculated for $C_{15}H_{15}NO_6S$: 338.0698, found: 338.0673.

EXAMPLE 11

(S)-N,2-dihydroxy-3-[(4-phenoxyphenyl)-sulfonyl]propanamide

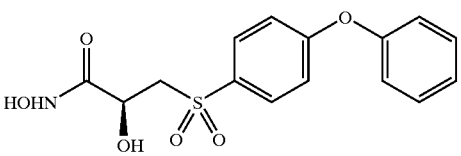

Part A: To a solution of L-serine (25.0 g, 237.9 mmol) in 6N HCl (300 mL) cooled to zero degrees C was added sodium nitrite (19.0 g, 275 mmol) and the solution was stirred for 3.5 hours. The solution was extracted with ethyl ether and the combined organic layers were dried over $Na_2SO_4$. Concentration in vacuo provided the chloro compound as a yellow oil (19.7 g, 67%).

Part B: To a solution of the chloro compound of part A (19.7 g, 160.6 mmol) in ethanol (50 mL) cooled to zero degrees C was added crushed KOH (14 g, 249.5 mmol). The solution stirred for 18 hours at ambient temperature. The reaction was filtered and the filtrate was concentrated in vacuo followed by trituration with ethyl ether provided the epoxide as a light yellow solid (14.1 g, 70%).

Part C: To a solution of 4-(phenoxy)benzenethiol (4.0 g, 19.8 mmol) in methanol (35 mL) cooled to 0° C. was added the epoxide of part B (3.1 g, 24.7 mmol) followed by sodium methoxide (preformed with 600 mg sodium in 50 mL methanol). The solution was heated at 40° C. for 24 hours. The solution was concentrated in vacuo and the residue was partitioned between ethyl acetate and 1N HCl. The organic layer was washed with saturated NaCl and dried over $MgSO_4$. Concentration in vacuo provided the crude sulfide as a tan solid (7.3 g, 86%).

Part D: To a solution of the sulfide of part C (5.7 g, 19.7 mmol) in methanol (100 mL) was added thionyl chloride (2.9 mL, 39.3 mmol) and the solution was heated at reflux for 1 hour. The solution was concentrated in vacuo and the residue was partitioned between ethyl acetate and saturated $NaHCO_3$. The aqueous layer was extracted with ethyl acetate and the combined organic layers were washed with saturated NaCl and dried over $MgSO_4$. Chromatography (ethyl acetate/hexane) provided the methyl ester as a colorless oil (4.1 g, 84%).

Part E: To a solution of the methyl ester of part D (4.1 g, 13.5 mmol) in methanol (100 mL) and H₂O (20 mL) was added Oxone® (29.0 g, 47.2 mmol) and the solution was stirred for 72 hours at ambient temperature. The mixture was filtered and the filtrate was concentrated in vacuo. The residue was partitioned between ethyl acetate and H₂O. The aqueous layer was extracted with ethyl acetate and the combined organic layers were washed with saturated NaCl and dried over MgSO₄. Concentration in vacuo provided the sulfone as a white solid (4.4 g, 98%).

Part F: To a solution of the sulfone of part E (3.9 g, 11.6 mmol) in methanol (20 mL) and THF (20 mL) was added 50% aqueous hydroxylamine (14 mL). The solution was stirred for 18 hours at ambient temperature. The solution was concentrated in vacuo and recrystallization (acetone/H₂O) provided (S)—N,2-dihydroxy-3-[(4-phenoxyphenyl)sulfonyl]propanamide as a white solid (3.0 g, 77%). HPLC purity: 97.6%. HRMS calculated for $C_{15}H_{15}NO_6S$: 338.0698, found: 338.0748.

EXAMPLE 12

N,2-dihydroxy-3-[[(4-(phenylthio)phenyl]-sulfonyl]propanamide

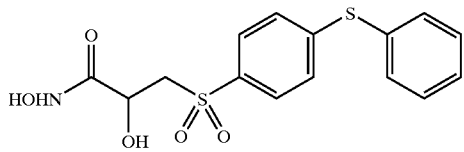

Part A: To a solution of β-chlorolactic acid (10.0 g, 80.3 mmol) in DMF (85 mL) was added 4-fluorothiophenol (10.3 g, 80.3 mmol) and K₂CO₃ (22 g, 16 mmol) and the solution was stirred for 1 hour at ambient temperature. The solution was concentrated in vacuo and the residue was partitioned between ethyl acetate and 1N KCl. The organic layer was dried over MgSO₄ and concentrated in vacuo. To a solution of the crude sulfide in methanol (250 mL) and H₂O (100 mL) was added Oxone® (149 g, 240 mmol) and the mixture was stirred for 6 hours at ambient temperature. The mixture was filtered, the filtrate was concentrated and trituration with ethyl ether provided the sulfone as a white solid (19 g, 91%).

Part B: To a solution of the sulfone of part A (7.4 g, 34.3 mmol) in DMF (70 mL) was added thiophenol (6.6 mL, 68.6 mmol) and K₂CO₃ (11.8 g, 85.5 mmol) and the solution was heated at 60° C. for 18 hours. The reaction was concentrated and the residue was partitioned between ethyl acetate and 1N HCl. The organic layer was dried over MgSO₄ and concentrated in vacuo. The crude acid was dissolved into methanol (250 mL) and was treated with thionyl chloride (3.0 mL, 41.2 mmol). The solution was stirred for 72 hours at ambient temperature. The solution was concentrated in vacuo and the residue was partitioned between ethyl acetate and H₂O. The organic layer was washed with saturated NaCl and dried over MgSO₄. Concentration in vacuo followed by trituration with ethyl provided the sulfone methyl ester as a white solid (5.9 g, 49%).

Part C: To a solution of the sulfone methyl ester of part B (2.1 g, 6.0 mmol) in methanol (20 ML) and THF (20 mL) was added 50% aqueous hydroxylamine (3.5 mL, 60 mmol) and the solution stirred for 18 hours at ambient temperature. Filtration of the resulting precipitate provided N,2-dihydroxy-3-[[4-(phenylthio)phenyl]-sulfonyl]propanamide as a white solid (1.4 g, 66%). HPLC purity: >98%. HRMS calculated for $C_{15}H_{15}NO_5S_2$: 354.0470, found: 354.0465.

EXAMPLE 13

N,2-dihydroxy-2-(hydroxymethyl)-3-[[4-(phenylthio)phenyl]sulfonyl]propanamide

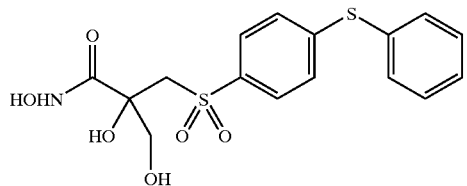

Part A: To a solution of 2-(bromomethyl)-acrylic acid (12.9 g, 78.0 mmol) and 4-fluorothiophenol (10.0 g, 78.0 mmol) in acetonitrile (400 mL) was added K₂CO₃ (21.6 g, 156 mmol). The solution was stirred for 1 hour at ambient temperature and then concentrated in vacuo. The residue was partitioned between ethyl acetate and 1N HCl. The organic layer was washed with saturated NaCl and dried over MgSO₄. Concentration in vacuo provided the sulfide as a yellow solid (16.2 g, 98%).

Part B: To a solution of the sulfide of part A (16.2 g, 76.4 mmol) in methanol (250 mL) and H₂O (50 mL) was added Oxone® (153 g, 250 mmol) and the solution was stirred for 20 hours at ambient temperature. The excess Oxone® was removed by filtration and the filtrate was concentrated in vacuo. The residue was partitioned between ethyl acetate and H₂O and the organic layer was washed with saturated NaCl and dried over MgSO₄. Concentration in vacuo provided the sulfone as a white solid (18.3 g, 96%).

Part C: To a solution of the sulfone of part B (18.3 g, 71.0 mmol) in methanol (250 mL) was added thionyl chloride (11.0 mL, 150 mmol) and the solution was heated at reflux for 3 hours. The solution was thereafter cooled and was stirred at ambient temperature for 18 hours. The solution was concentrated in vacuo and the residue was partitioned between ethyl acetate and saturated NaHCO₃. The aqueous solution was extracted once with ethyl acetate and the organic layers were combined and washed with saturated NaCl and dried over MgSO₄. Concentration in vacua provided the methyl ester as a tan oil (16.0 g, 80%).

Part D: To a solution of 4-methylmorpholine N-oxide (14.5 g, 123.9 mmol) in acetone/H₂O (8:1, 150 mL) was added osmium tetroxide (2.5 wt. % in 2-methyl-2-propanol) followed by the methyl ester of part C (16.0 g, 61.9 mmol) in acetone/H₂O. The solution was stirred for 18 hours at ambient temperature. To the reaction was added Na₂SO₃ (8 g) and the mixture was stirred for 30 minutes followed by concentration in vacuo. The residue was partitioned between ethyl acetate and H₂O and the organic layer was washed with saturated NaCl and dried over MgSO₄. Concentration in vacuo provided the diol as a white solid (16.3 g, 90%).

Part E: To a solution of thiophenol (700 mg, 6.84 mmol) in DMF (10 mL) was added K₂CO₃ (950 mg, 6.84) and the solution was stirred for 30 minutes. To this solution was added the diol of part D (1.0 g, 3.42 mmol) and the solution was heated to 70° C. for 2 hours and then for 18 hours at ambient temperature. The solution was concentrated in vacuo and the residue was partitioned between ethyl acetate and 1N HCl. The organic layer was washed with H₂O and saturated NaCl and dried over MgSO₄. Concentration in vacuo provided a mixture of ester and acid. The crude product was dissolved into acetic acid (15 mL) and concentrated HCl (15 mL) and heated at 70° C. for 3 hours. The solution was concentrated in vacua. Reverse phase chromatography (acetonitrile/H$_2$O) provided the acid as a white solid (740 mg, 57%).

Part F: To a solution of the acid of part E (740 mg, 2.01 mmol) in DMF (10 mL) was added N-hydroxybenzotriazole (330 mg, 2.41 mmol), 4-methymorpholine (0.70 mL, 6.03 mmol), 50% aqueous hydroxylamine (2.4 mL, 40.2 mmol) and EDC (420 mg, 2.21 mmol). After stirring for 1 hour and standing for 72 hours the solution was concentrated in vacuo. Reverse phase chromatography (acetonitrile/H$_2$O) followed by crystallization (acetone/ethanol) provided N,2-dihydroxy-2-(hydroxymethyl)-3-[[4-(phenylthio)-phenyl]sulfonyl]propanamide as white crystals (300 mg, 33%). HPLC purity: 98.7%. HRMS calculated for C$_{16}$H$_{17}$NO$_6$N$_2$: 384.0576, found 384.0578.

EXAMPLE 14

N-[4-[[2-hydroxy-3-(hydroxyamino)-2-methyl-3-oxopropyl]sulfonyl]phenyl]-pentylbenzamide

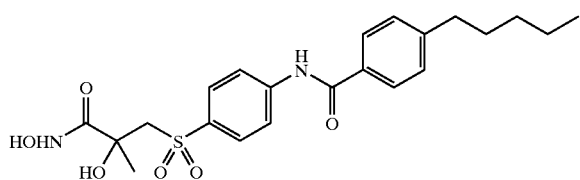

Part A: To a solution of 4-nitrothiophenol (80%, 15.518 g, 92.9 mmol) in methanol (200 mL) was added triethylamine (14.6 mL, 105 mmol) followed by chloroacetone (8.4 mL, 105 mmol). The solution stirred for 1 hour at ambient temperature. The solution was concentrated in vacuo and the residue was dissolved into ethyl acetate and washed with 5% KHSO$_4$, saturated NaHCO$_3$ and saturated NaCl and dried over Na$_2$SO$_4$. Chromatography (ethyl acetate/hexanes) provided the sulfide as an oil (16.6 g, 85%).

Part B: To a solution of the sulfide of part A (16.6 g, 78.4 mmol) in dichloromethane (150 mL) cooled to 4° C. was added trimethylsilyl cyanide (8.56 g, 86.3 mmol) and zinc iodide (1.8 g). The solution was stirred for 1 hour at 4° C. and for 18 hours at ambient temperature. The solution was partitioned between ethyl acetate and H$_2$O and washed with saturated NaCl and dried over Na$_2$SO$_4$. Concentration in vacuo provided the protected cyanohydrin as a yellow oil (23.7 g).

Part C: To a solution of the cyanohydrin of part B (23.7 g) in acetic acid (100 mL) was added 12N HCl and the solution was heated at reflux for 17 hours. After concentration in vacuo, trituration of the residue with ethyl ether provided the acid as a white solid (15.2 g, 75%, 2 steps).

Part D: To a solution of the acid of part C (15.2 g, 59 mmol) in methanol (270 mL) and H$_2$O (30 mL) was added Oxone® (112.4 g, 183 mmol) and the solution was stirred for 18 hours at ambient temperature. The solution was filtered to remove the insoluble salts and the filtrate was concentrated in vacuo. The residue was dissolved into ethyl acetate and washed with H$_2$O and dried over Na$_2$SO$_4$. Concentration in vacuo provided the sulfone as a solid (12.6 g, 74%).

Part E: To a solution of the sulfone of part D (12.6 g, 43.6 mmol) in methanol (200 mL) cooled to 0° C. was added thionyl chloride (6.35 mL, 87.1 mmol) dropwise. The solution was heated at reflux for 1 hour. The solution was cooled and concentrated in vacua. The residue was dissolved into ethyl acetate and washed with H$_2$O, and saturated NaCO$_3$, and dried over Na$_2$SO$_4$. Concentration in vacuo provided the methyl ester as a beige solid (12.7 g, 96%).

Part F: To a solution of the methyl ester of part E (12.6 g, 41.5 mmol) in THF (250 mL) under H$_2$ was added wet 10% Pd/C. The solution was stirred at ambient temperature for 18 hours. The mixture was filtered through a Celite pad and the filtrate was concentrated in vacua to provide the aniline compound as an off-white solid (11.1 g, 98%).

Part G: To a suspension of the aniline compound of part E (100 mg, 0.37 mmol) in dichloromethane (8 mL) was added pyridine (0.044 mL, 0.55 mmol) followed by 4-pentylbenzoyl chloride (0.093 mL, 0.44 mmol). The mixture was heated to 60° C. for 1 hour. To the solution was added polyamine resin (0.368 g, 1.1 mmol, 2.98 meq/g loading) and heating the solution was continued at 60° C. for 1 hour. The mixture was filtered and concentrated in vacuo to provide the amide as a white solid (167 mg, quantitative yield).

Part H: To a solution of the amide of part G (163 mg, 0.36 mmol) in THF (4 mL) and methanol (4 mL) was added 50% aqueous hydroxylamine (0.60 mL, 10.2 mmol). The solution was stirred for 96 hours at ambient temperature and for 24 hours at 40° C. The solution was concentrated and redissolved into THF (1.5 mL) and 50% aqueous hydroxylamine (1.5 mL). The solution was stirred for 24 hours and then concentrated. The residue was partitioned between ethyl acetate and H$_2$O, and the organic layer was washed with H$_2$O and saturated NaCl, and then dried over Na$_2$SO$_4$. Reverse phase chromatography (acetonitrile/H$_2$O) provided the hydroxamate, N-[4-[[2-hydroxy-3-(hydroxyamino)-2-methyl-3-oxopropyl]sulfonyl]phenyl]-pentylbenzamide, as a pink solid (103 mg, 63%). MS(CI) MH$^+$ calculated for C$_{22}$H$_{26}$N$_2$O$_6$S: 449, found: 449.

EXAMPLE 15

N,2-dihydroxy-2-methyl-3-[[4-[[(phenylamino) carbonyl]amino]phenyl]sulfonyl]propanamide

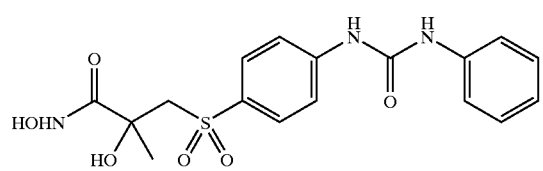

Part A: To a solution of the aniline compound of Example 14, part F (500 mg, 1.83 mmol) in dichloromethane (10 mL) was added phenyl isocyanate (436 mg, 3.66 mmol) and the solution was stirred for 20 hours at ambient temperature. The solution was concentrated in vacuo and the residue was dissolved into ethyl acetate and washed with H$_2$o and saturated NaCl and dried over Na$_2$SO$_4$. Concentration in vacuo provided the urea methyl ester as an oil (392 mg, 55%).

Part B: To a solution of the urea methyl ester of part A (392 mg, 1.0 mmol) was added 50% aqueous hydroxylamine (3.0 mL) and the solution stirred for 96 hours. The solution was diluted with ethyl acetate and washed with H$_2$O and saturated NaCl, and then dried over Na$_2$SO$_4$. Reverse phase chromatography (acetonitrile/H$_2$O) provided N,2-dihydroxy-2-methyl-3-[[4-[[(phenylamino)-carbonyl] amino]phenyl]sulfonyl]-propanamide as a pink solid (77 mg, 20%). MS(CI) MH$^+$ calculated for C$_{17}$H$_{19}$N$_3$O$_6$S: 394, found: 394.

EXAMPLE 16

N-[4-[[2-hydroxy-3-(hydroxyamino)-2-methyl-3-oxopropyl]sulfonyl]-phenyl]benzamide

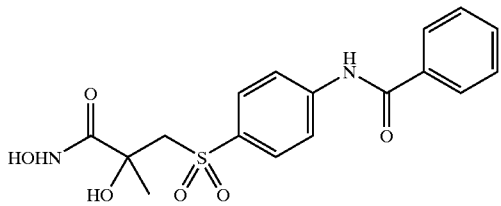

Part A: To a solution of the aniline of Example 14, part F (500 mg, 1.83 mmol) in 1,2-dichloroethane (20 mL) was added pyridine (0.22 mL, 2.7 mmol) followed by benzoyl chloride (0.25 mL, 2.2 mmol). The solution stirred at ambient temperature for 1 hour followed by the addition of polyamine resin (3.0 meq/g loading, 1.5 g, 4.5 mmol) and the stirring was continued for 1 hour. The mixture was filtered and the filtrate was concentrated in vacuo to provide the amide methyl ester as an off-white solid (688 mg, 99%).

Part B: To a solution of the amide methyl ster of part A (674 mg, 1.79 mmol) in THF (15 mL) was added 50% aqueous hydroxylamine (15 mL) and was stirred for 72 hours. The solution was concentrated and the residue was extracted with ethyl acetate and washed with saturated NaCl, and then dried over $Na_2SO_4$. Trituration with ethyl acetate and ethyl ether provided N-[4 [[2-hydroxy-3-(hydroxyamino)-2-methyl-3-oxopropyl]sulfonyl]phenyl] benzamide as a white solid (328 mg, 48%). MS(CI) $MH^+$ calculated for $C_{17}H_{15}N_2O_6S$: 379, found: 379.

EXAMPLE 17

N-[4-[[2-hydroxy-3-(hydroxyamino)-2-methyl-3-oxopropyl]sulfonyl]phenyl]-3-methylbutanamide

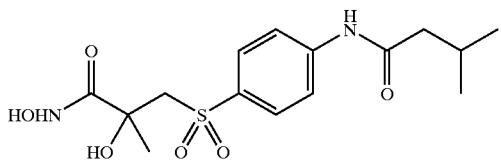

Part A: To a solution of the aniline of Example 14, part F (500 mg, 1.33 mmol) in 1,2-dichloroethane (20 mL) was added pyridine (0.22 mL, 2.7 mmol) followed by isovaleryl chloride (0.27 mL, 2.2 mmol). The solution stirred at ambient temperature for 1.5 hours followed by the addition of polyamine resin (3.0 meq/g loading, 1.5 g, 4.5 mmol) and the stirring continued for 1 hour. The mixture was filtered and the filtrate was concentrated in vacuo to provide the methyl ester amide as a yellow oil (746 mg, quantitative yield).

Part B: To a solution of the methyl ester amide of part A (736 mg, 1.83 mmol) in THF (10 mL) was added 50% aqueous hydroxylamine (10 mL), and the solution was stirred for 96 hours. The solution was concentrated and the residue was extracted with ethyl acetate, washed with saturated NaCl, and then dried over $Na_2SO_4$. Reverse phase chromatography (acetonitrile/$H_2O$) provided N-[4-[[2-hydroxy-3-(hydroxyamino)-2-methyl-3-oxopropyl] sulfonyl]phenyl]-3-methylbutanamide as a pink solid (247 mg, 38%). MS(CI) $MH^+$ calculated for $C_{15}H_{22}N_2O_6S$: 359, found: 359.

EXAMPLE 18

4-chloro-N-[4-[[2-hydroxy-3-(hydroxyamino)-2-methyl-3-oxopropyl]-sulfonyl]phenyl]-benzamide

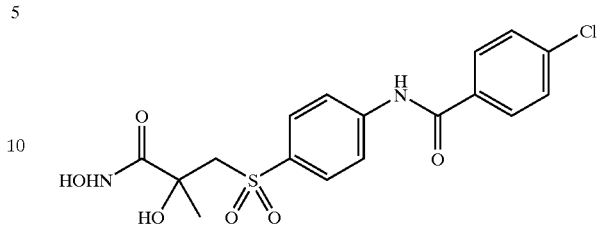

Part A: To a solution of the aniline of Example 14, part F (300 mg, 1.10 mmol) in 1,2-dichloroethane (10 mL) was added pyridine (0.133 mL, 1.65 mmol) followed by 4-chlorobenzoyl chloride (0.17 mL, 1.3 mmol). The solution stirred at ambient temperature for 1 hour. The resulting precipitate was triturated with ethyl ether and collected to provide the amide methyl ester as a white solid (368 mg, 81%).

Part B: To a solution of the amide methyl ester of part A (368 mg, 0.89 mmol) in THF (2 mL) and methanol (4 mL) was added 50% aqueous hydroxylamine (3 mL) and was stirred for 96 hours. The solution was concentrated and the residue was extracted with ethyl acetate and washed with saturated NaCl and dried over $Na_2SO_4$. Trituration with ethyl acetate provided 4-chloro-N-[4-[[2-hydroxy-3-(hydroxyamino)-2-methyl-3-oxopropyl[sulfonyl[phenyl[-benzamide as a white solid (126 mg, 34%). MS(CI) $MH^+$ calculated for $C_{17}H_{17}N_2O_6SCl$: 430, found: 430.

EXAMPLE 19

N,2-dihydroxy-2-methyl-3-[[4-[[[(2-methylphenyl)amino]carbonyl]-amino]phenyl]sulfonyl]propanamide

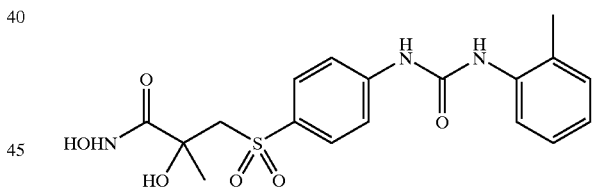

Part A: To a solution of the aniline of Example 14, part F (500 mg, 1.83 mmol) in 1,2-dichloroethane (15 mL) was added o-tolyl isocyanate (0.354 mL, 2.74 mmol). The solution was heated to 60° C. for 15 hours followed by the addition of polyamine resin (3.0 meq/g loading, 1.00 g, 3.00 mmol) and continued heating for 7 hours. The mixture was filtered and the filtrate was concentrated. Chromatography (ethyl acetate/hexane) provided the urea methyl ester as a pink solid (496 mg, 67%).

Part B: To a solution of the urea methyl ester of part A (496 mg, 1.22 mmol) in THF (12 mL) was added potassium trimethylsilanolate (188 mg, 1.46 mmol) and was stirred for 20 hours at ambient temperature. The solution was cooled to zero degrees C, diluted with $H_2O$ and acidified with 1N HCl (1.5 mL). The THF was removed. The aqueous layer was extracted with ethyl acetate, and the organic layer was washed with saturated NaCl and dried over $Na_2SO_4$. Concentration in vacuo provided the acid as a yellow solid (480 mg, quantitative yield).

Part C: To a solution of the acid of part B (480 mg, 1.22 mmol) in DMF (12 mL) was added N-hydroxy-benzotriazole (181 mg, 1.34 mmol) and 1-(3-dimethyl-aminopropyl)-3-ethylcarbodiimide hydrochloride (257 mg, 1.34 mmol). After 1 hour of stirring at ambient temperature 50% aqueous hydroxylamine (0.216 mL, 3.66 mmol) and 4-methylmorpholine (0.54 mL, 4.9 mmol) were added. After 30 minutes the DMF was removed and the residue was partitioned between ethyl acetate and $H_2O$. The organic layer was washed with saturated NaCl and dried over $Na_2SO_4$. Reverse phase chromatography provided N,2-dihydroxy-2-methyl-3-[[4-[[(2-methylphenyl)amino]carbonyl]amino]phenyl]-sulfonyl]propanamide as a pink solid (39 mg, 8%) MS(CI) $MH^+$ calculated for $C_{18}H_{21}N_3O_6S$: 408, found 408.

EXAMPLE 20

N,2-dihydroxy-2-methyl-3-[[4-[[[(3-methylphenyl)amino]carbonyl]-aminolphenyl]sulfonyl]propanamide

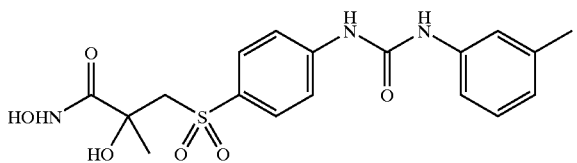

Part A: To a solution of the aniline of Example 14, part F (500 mg, 1.83 mmol) in 1,2-dichloroethane (15 mL) was added m-tolyl isocyanate (0.353 mL, 2.74 mmol). The solution was heated to 60° C. for 15 hours followed by the addition of polyamine resin (3.0 meq/g loading, 1.00 g, 3.00 mmol) and continued heating for 7 hours. The mixture was filtered and the filtrate was concentrated. Chromatography (ethyl acetate/hexane) provided the urea methyl ester as a pale yellow oil (346 mg, 47%).

Part B: To a solution of the urea methyl ester of part A (346 mg, 0.851 mmol) in THF (10 mL) was added potassium trimethylsilanolate (131 mg, 1.02 mmol) and was stirred for 18 hours at ambient temperature. The solution was cooled to zero degrees C, diluted with $H_2O$ and acidified with 1N HCl. The THF was removed. The aqueous layer was extracted with ethyl acetate and the organic layer was washed with saturated NaCl and dried over $Na_2SO_4$. Concentration in vacuo provided the acid as a pink solid (330 mg, 99%).

Part C: To a solution of the acid of part B (330 mg, 0.841 mmol) in DMF (8 mL) was added N-hydroxy-benzotriazole (125 mg, 0.925 mmol) and 1-(3-dimethyl-aminopropyl)-3-ethylcarbodiimide hydrochloride (177 mg, 0.925 mmol). After 1 hour of stirring at ambient temperature 50% aqueous hydroxylamine (0.149 mL, 2.52 mmol) and 4-methylmorpholine (0.37 mL, 3.7 mmol) were added. After 30 minutes the DMF was removed and the residue was partitioned between ethyl acetate and $H_2O$.

The organic layer was washed with saturated NaCl and dried over $Na_2SO_4$. Reverse phase chromatography provided N,2-dihydroxy-2-methyl-3-[[4-[[[(3-methylphenyl)amino]carbonyl]amino]phenyl]sulfonyl]-propanamide as a white solid (265 mg, 77%). MS(CI) $MH^+$ calculated for $C_{18}H_{22}N_3O_6S$: 408, found: 408.

EXAMPLE 21

N,2-dihydroxy-2-methyl-3-[[4-[[[(4-methylphenyl)amino]carbonyl]-amino]phenl]sulfonyl]propanamide

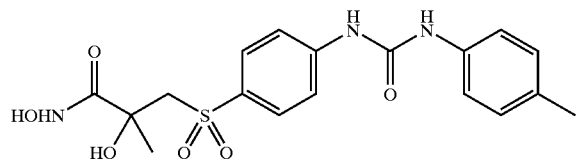

Part A: To a solution of the aniline of Example 14, part F (500 mg, 1.83 mmol) in THF (15 mL) was added p-tolyl isocyanate (0.461 mL; 3.66 mmol). The solution was stirred at ambient temperature for 72 hours. The solution was then diluted with dichloromethane (50 mL) and polyamine resin (3.0 meq/g loading, 2.50 g, 7.50 mmol) was added and the mixture stirred for 4 hours. The mixture was filtered and the filtrate was concentrated. Chromatography (ethyl acetate/hexane) provided the urea methyl ester as a white solid (554 mg, 74%).

Part B: To a solution of the urea methyl ester of part A (554 mg, 1.36 mmol) in THF (13 mL) was added potassium trimethylsilanolate (210 mg, 1.64 mmol) and the solution was stirred for 18 hours at ambient temperature. The solution was cooled to zero degrees C, diluted with $H_2O$ and acidified with 1N HCl. The THF was removed. The aqueous layer was extracted with ethyl acetate and the organic layer was washed with saturated NaCl and dried over $Na_2SO_4$. Concentration in vacuo provided the acid as an off-white solid (530 mg, 99%).

Part C: To a solution of the acid of part B (500 mg, 1.27 mmol) in DMF (13 mL) was added N-hydroxy-benzotriazole (189 mg, 1.40 mmol) and 1-(3-dimethyl-aminopropyl)-3-ethylcarbodiimide hydrochloride (268 mg, 1.40 mmol). After 1 hour of stirring at ambient temperature 50% aqueous hydroxylamine (0.282 mL, 3.81 mmol) and 4-methylmorpholine (0.56 mL, 5.1 mmol) were added. After 30 minutes the DMF was removed and the residue was partitioned between ethyl acetate and $H_2O$. The organic layer was washed with saturated NaCl and dried over $Na_2SO_4$. Reverse phase chromatography provided N,2-dihydroxy-2-methyl-3-[[4-[[[(4-methylphenyl)amino]carbonyl]amino]phenyl]sulfonyl]-propanamide as an off-white solid (202 mg, 39%). MS(CI) $MH^+$ calculated for $C_{18}H_{21}N_3O_6S$: 408, found 408.

EXAMPLE 22

6-chloro-N-[4-[[2-hydroxy-3-(hydroxyamino)-2-methyl-3-oxopropyl]-sulfonyl]phenyl]-3-pyridinecarboxamide

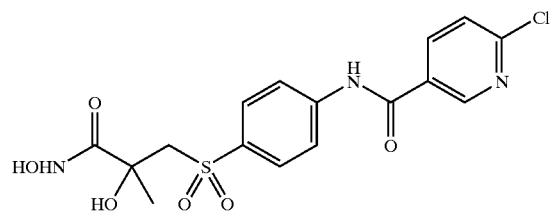

Part A: To a solution of the aniline of Example 14, part F (500 mg, 1.83 mmol) in 1,2-dichloroethane (10 mL) was added pyridine (0.22 mL, 2.7 mmol) followed by 6-chloronicotinyl chloride (383 mg, 2.2 mmol). The solution stirred at ambient temperature for 1 hour followed by the addition of polyamine resin (3.0 meq/g loading, 1.5 g, 4.5 mmol) and the stirring was continued for 1 hour. The mixture was filtered and the filtrate was concentrated in vacuo to provide the amide methyl ester as an off-white solid (750 mg, 99%).

Part B: To a solution of the amide methyl ester of part A (750 mg, 1.82 mmol) in THF (10 mL) was added 50% aqueous hydroxylamine (3 mL) and was stirred for 96 hours. The solution was concentrated, the residue was extracted with ethyl acetate, washed with saturated NaCl and dried over $Na_2SO_4$. Reverse phase chromatography (acetonitrile/$H_2O$) provided 6-chloro-N-[4-[[2-hydroxy-3-(hydroxyamino)-2-methyl-3-oxopropyl]-sulfonyl]phenyl]-3-pyridinecarboxamide as a white solid (29 mg, 4%). MS (CI) M-H calculated for $C_{16}H_{16}N_3O_6SCl$: 412, found: 412.

EXAMPLE 23

N-[4-[[2-hydroxy-3-(hydroxyamino)-3-oxopropyl]sulfonyl]phenyl]benzamide

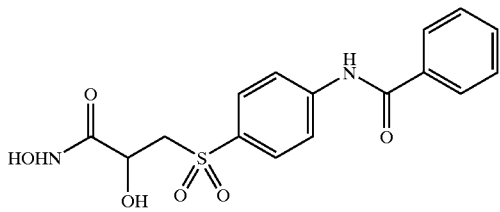

Part A: To a solution of β-chlorolactic acid (10.0 g, 80.3 mmol) in DMF (200 mL) was added $K_2CO_3$ (33.3 g, 240.96 mmol) and 4-aminothiophenol (11.60 g, 92.66 mmol). The solution was stirred for 20 hours at ambient temperature. The solution was concentrated in vacuo and the residue was dissolved into $H_2O$ and acidified with 6N HCl to pH=2.5. The resulting precipitate was collected by vacuum filtration and dried providing the acid sulfide as an off-white solid (12.4 g, 72%).

Part B: To a solution of the acid sulfide of part A (11.88 g, 55.71 mmol) in methanol (200 mL) cooled to zero degrees C was added thionyl chloride (12.2 mL, 167.13 mmol). The solution was heated at reflux for 2 hours followed by concentration in vacuo. The residue was dissolved into saturated $NaHCO_3$ and extracted with ethyl acetate. The organic layer was washed with saturated NaCl and dried over $Na_2SO_4$. Concentration in vacuo provided the methyl ester as a tan solid (11.47 g, 91%).

Part C: To a suspension of the methyl ester of part B (10.00 g, 44.0 mmol) in dichloromethane (100 mL) was added pyridine (5.34 mL, 66.00 mmol) and benzoyl chloride (5.62 mL, 48.4 mmol). The solution was stirred at ambient temperature for 20 hours. The solution was concentrated in vacua. The residue was partitioned between ethyl acetate and $H_2O$, and the organic layer was washed with $H_2O$ and saturated NaCl. Concentration in vacuo provided the amide sulfide as an off-white solid (14.56 g, quantitative yield).

Part D: To a solution of the amide sulfide of part C (3.00 g, 9.05 mmol) in THF (100 mL) and $H_2O$ (10 mL) was added Oxone® (10.0 g, 16.3 mmol). The solution stirred at zero degrees C for 2 hours. The mixture was filtered and the filtrate was concentrated to one-third volume. This solution was diluted with ethyl acetate, washed with $H_2O$ and saturated NaCl, and then dried over $Na_2SO_4$. Chromatography (ethyl acetate/hexane) provided the sulfone methyl ester as an off-white solid (2.68 g, 81).

Part E: To a solution of the sulfone methyl ester of part D (500 mg, 1.38 mmol) in THF (6 mL) was added 50% aqueous hydroxylamine (6 mL). The solution was stirred at ambient temperature for 8 hours. Trituration with THF provided N-[4-[[2-hydroxy-3-(hydroxyamino)-3-oxopropyl]sulfonyl]phenyl]benzamide as an off-white solid (393 mg, 78%). MS(CI) $MH^+$ calculated for $C_{16}H_{16}N_2O_6S$: 365, found: 365.

EXAMPLE 24

4-(heptyloxy)-N-[4-[[2-hydroxy-3-(hydroxyamino)-2-methyl-3-oxopropyl]-sulfonyl]phenyl]benzamide

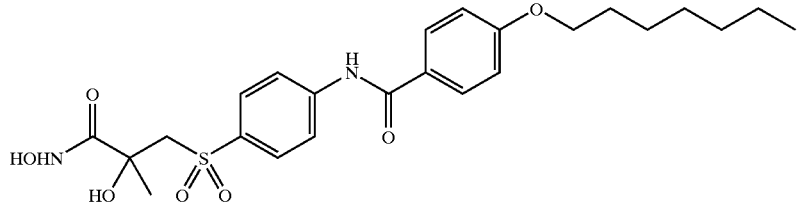

Part A: To a solution of the aniline compound of Example 14, part F (532 mg, 1.95 mmol) in THF (15 mL) was added triethylamine (1.09 mL, 7.8 mmol) and 4-heptyloxybenzoyl chloride (502 mg, 1.95 mmol) and the solution was refluxed for 1.5 hours. Chromatography (ethyl acetate/hexane) provided the amide methyl ester (605 mg, 63%).

Part B: To a solution of the amide methyl ester of part A (500 mg, 1.02 mmol) in THF (10 mL) and methanol (10 mL) was added 50% aqueous hydroxylamine (12 mL) and the solution stirred for 11 days at ambient temperature. The solvent was concentrated in vacuo. The residue was dissolved into ethyl acetate, washed with $H_2O$ and dried over $Na_2SO_4$. Crystallization (hexane) provided 4-(heptyloxy)-N-[4-[[2-hydroxy-3-(hydroxyamino)-2-methyl-3-oxopropyl]sulfonyl]phenyl]-benzamide as a white solid (215 mg, 43%). HRMS ($MH^+$) calculated for $C_{24}H_{32}N_2O_7S$: 493.2008, found: 493.2027.

EXAMPLE 25

4-butoxy-N-[4-[[2-hydroxy-3-(hydroxyamino)-2-methyl-3-oxopropyl]-sulfonyl]phenyl]benzamide

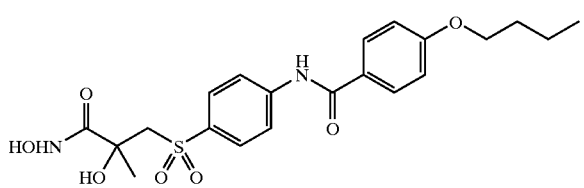

Part A: To a solution of the aniline compound of Example 14, part F (560 mg, 2.05 mmol) in THF (15 mL) was added triethylamine (1.14 mL, 8.2 mmol) and 4-butoxybenzoyl chloride (654 mg, 3.075 mmol) and the solution was refluxed for 5 hours. The solution was concentrated in vacuo, and trituration with ethyl ether provided the amide methyl ester as white solid (407 mg, 43%).

Part B: To a solution of the amide methyl ester of part A (400 mg, 0.89 mmol) in THF (10 mL) was added 50% aqueous hydroxylamine (10 mL) and the solution was stirred at ambient temperature for 72 hours. The solution was concentrated in vacuo. The residue was partitioned between ethyl acetate and $H_2O$, and the organic layer was dried over $Na_2SO_4$. Concentration in vacuo provided 4-butoxy-N-[4-[[2-hydroxy-3-(hydroxyamino)-2-methyl-3-oxopropyl]-sulfonyl]phenyl]-benzamide as a white solid (335 mg, 84%). HRMS (MH$^+$) calculated for $C_{21}H_{26}N_2O_7S$: 451.1539, found: 451.1540.

EXAMPLE 26

N-[4-[[2-hydroxy-3-(hydroxyamino)-2-methyl-3-oxopropyl]-sulfonyl]phenyl]-4-propylbenzamide

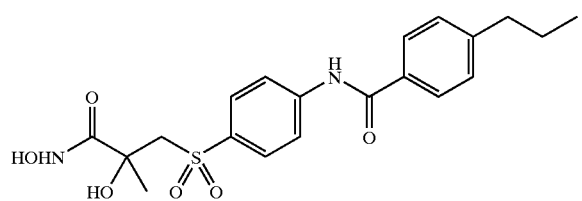

Part A: To a solution of the aniline compound of Example 14, part F (530 mg, 1.94 mmol) in THF (10 mL) was added triethylamine (1.08 mL, 7.76 mmol) followed by 4-propylbenzoyl chloride (532 mg, 2.91 mmol) and the solution was heated at reflux for 3 hours. The solution was concentrated in vacuo. The residue was dissolved into ethyl acetate, washed with $H_2O$ and dried over $Na_2SO_4$. Recrystallization (ethyl acetate/hexane) provided the amide methyl ester as white crystals (570 mg, 70%).

Part B: To a solution of the amide methyl ester of part A (560 mg, 1.3 mmol) in THF (10 mL) was added 50% hydroxylamine (10 mL) and the solution was stirred for 7 days. The solution was concentrated in vacuo and the residue was partitioned between ethyl acetate and $H_2O$. The organic was dried over $Na_2SO_4$. Concentration in vacuo provided N-[4-[[2-hydroxy-3-(hydroxyamino)-2-methyl-3-oxopropyl]-sulfonyl]phenyl]-4-propylbenzamide as a white solid (438 mg, 80%). HRMS (MH$^+$) calculated for $C_{20}H_{24}N_2O_6S$: 421.1433, found: 421.1396.

EXAMPLE 27

N-[4-[[2-hydroxy-3-(hydroxyamino)-2-methyl-3-oxopropyl]-sulfonyl]-phenyl]-3-methoxybenzamide

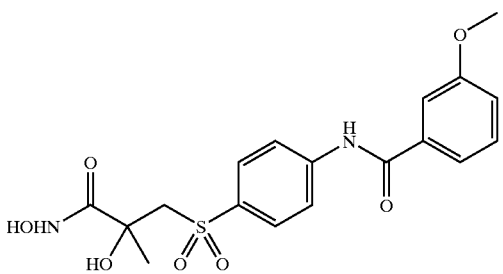

Part A: To a solution of the aniline compound of Example 14, part F (563 mg, 2.06 mmol) in THF (10 mL) was added triethylamine (1.0 mL, 7.19 mmol) followed by m-anisoyl chloride (0.434 mL, 3.09 mmol) and the solution was heated at reflux for 3 hours. The solution was concentrated in vacua. The residue was dissolved into ethyl acetate, washed with $H_2O$ and dried over $Na_2SO_4$. Recrystallization (ethyl acetate/hexane) provided the amide methyl ester as white crystals (539 mg, 64%).

Part B: To a solution of the amide methyl ester of part A (530 mg, 1.3 mmol) in THF (10 mL) was added 50% hydroxylamine (10 mL) and the solution was stirred for 7 days. The solution was concentrated in vacuo and the residue was partitioned between ethyl acetate and $H_2O$. Reverse phase chromatography (acetonitrile/$H_2O$) provided N-[4-[[2-hydroxy-3-(hydroxyamino)-2-methyl-3-oxopropyl]sulfonyl]phenyl]-3-methoxybenzamide as a white solid (190 mg, 36%). HRMS (MH$^+$) calculated for $C_{a18}H_{20}N_2O_7S$: 409.1069, found: 409.1093.

EXAMPLE 28

4-butyl-N-[4-[[2-hydroxy-3-(hydroxyamino)-2-methyl-3-oxopropyl]-sulfonyl]-phenyl]benzamide

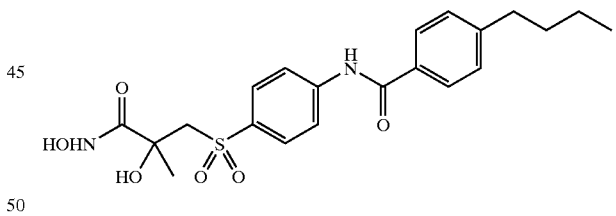

Part A: To a solution of the aniline compound of Example 14, part F (573 mg, 2.10 mmol) in THF (10 mL) was added triethylamine (1.3 mL, 9.3 mmol) followed by 4-butylbenzoylchloride (619 mg, 3.15 mmol) and the solution was heated at reflux for 4.5 hours. The solution was concentrated in vacuo. The residue was dissolved into ethyl acetate, washed with $_2O$ and dried over $Na_2SO_4$. Recrystallization (ethyl acetate/hexane) provided the amide methyl ester as a white solid (682 mg, 75%).

Part B: To a solution of the amide methyl ester of part A (682 mg, 1.6 mmol) in THF (10 mL) was added 50% hydroxylamine (10 mL) and the solution was stirred for 10 days. The solution was concentrated in vacuo, and the residue was partitioned between ethyl acetate and $H_2O$. Concentration in vacuo provided 4-butyl-N-[4-[[2-hydroxy-3-(hydroxyamino)-2-methyl-3-oxopropyl]-sulfonyl]phenyl]

benzamide as a white solid (522 mg, 75%). HRMS (MH$^+$) calculated for $C_{21}H_{26}N_2O_6S$: 435.1590, found: 435.1577.

EXAMPLE 29

3-fluoro-N-[4-[[2-hydroxy-3-(hydroxyamino)-2-methyl-3-oxopropyl]-sulfonyl]phenyl]benzamide

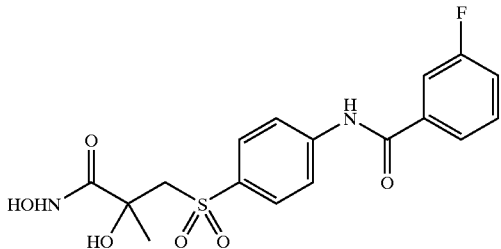

Part A: To a solution of the aniline compound of Example 14, part F (566 mg, 2.07 mmol) in THF (10 mL) was added triethylamine (1.0 mL, 7.2 mmol) followed by 3-fluorobenzoyl chloride (490 m.g, 3.1 mmol) and the solution was heated at reflux for 4.5 hours. The solution was concentrated in vacuo. The residue was dissolved into ethyl acetate, washed with $H_2O$ and dried over $Na_2SO_4$. Chromatography (ethyl acetate/hexane) provided the amide methyl estex as a white solid (460 mg, 56%).

Part B: To a solution of the amide methyl ester of part A (400 mg, 1.0 mmol) in THF (20 mL) and methanol (5 mL) was added 50% hydroxylamine (20 mL) and the solution was stirred for 20 hours. The solution was concentrated in vacua and the residue was partitioned between ethyl acetate and $H_2O$. Concentration in vacuo provided 3-fluoro-N-[4-[[2-hydroxy-3-(hydroxyamino)-2-methyl-3-oxopropyl]-sulfonyl]phenyl]benzamide as a white solid (363 mg, 91%). HRMS (MH$^+$) calculated for $C_{17}H_{17}N_2O_6SF$: 397.0870, found: 397.0864.

EXAMPLE 30

N-[4-[[2-hydroxy-3-(hydroxyamino)-2-methyl-3-oxopropyl]sulfonyl]-phenyl]-3-methylbenzamide

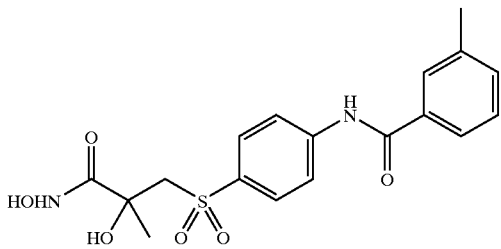

Part A: To a solution of the aniline compound of Example 14, part F (537 mg, 1.97 mmol) in THF (10 mL) was added triethylamine (1.0 mL, 7.2 mmol) followed by m-toluoyl chloride (0.39 mL, 2.9 mmol) and the solution was heated at reflux for 5 hours. The solution was concentrated in vacuo. The residue was dissolved into ethyl acetate, washed with $H_2O$ and dried over $Na_2SO_4$. Chromatography (ethyl acetate/hexane) provided the amide methyl ester as an oil (550 mg, 71%).

Part B: To a solution of the amide methyl ester of part A (500 mg, 1.3 mmol) in THF (10 mL)and methanol (5 mL) was added 50% hydroxylamine (20 mL) and the solution was stirred for 25 hours. The solution was concentrated in vacuo and the residue was partitioned between ethyl acetate and $H_2O$. Concentration in vacuo provided N-[4-[[2-hydroxy-3-(hydroxyamino)-2-methyl-3-oxopropyl] sulfonyl]phenyl]-3-methylbenzamide as a white solid (352 mg, 70%). HRMS (MH$^+$) calculated for $C_{18}H_{20}N_2O_6S$: 393.1120, found: 393.1127.

EXAMPLE 31

3-chloro-N-[4-[[2-hydroxy-3-(hydroxyamino)-2-methyl-3-oxopropyl]-sulfonyl]phenyl]benzamide

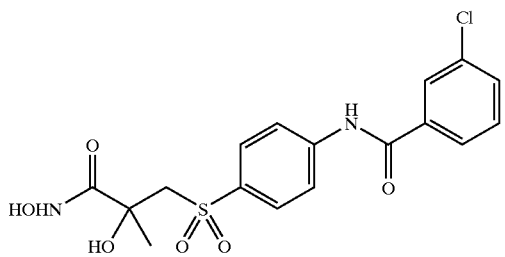

Part A: To a solution of the aniline compound of Example 14, part F (525 mg, 1.92 mmol) in THF (10 mL) was added triethylamine (1.0 mL, 7.2 mmol) followed by 3-chlorobenzoyl chloride (0.322 mL, 2.88 mmol) and the solution was heated at reflux for 5 hours. The solution was concentrated in vacuo. The residue was dissolved into ethyl acetate, washed with $H_2O$ and dried over $Na_2SO_4$. Crystallization (ethyl acetate/hexane) provided the amide methyl ester as a white solid (230 mg, 29%).

Part B: To a solution of the amide methyl ester of part A (230 mg, 0.56 mmol) in THF (5 mL)and methanol (5 mL) was added 50% hydroxylamine (10 mL) and the solution was stirred for 48 hours. The solution was concentrated in vacuo and t he residue was partitioned between ethyl acetate and $H_2O$. Concentration in vacuo provided 3-chloro-N-[4-[[2-hydroxy-3-(hydroxyamino)-2-methyl-3-oxopropyl]-sulfonyl]phenyl]benzamide as a white solid (160 mg, 70%). HRMS (MH$^+$) calculated for $C_{17}H_{17}N_2O_6S$: 430.0840, found: 430.0864.

EXAMPLE 32

3,4-difluoro-N-[4-[[2-hydroxy-3-(hydroxyamino)-2-methyl-3-oxoproyl]sulfonyl]phenyl]benzamide

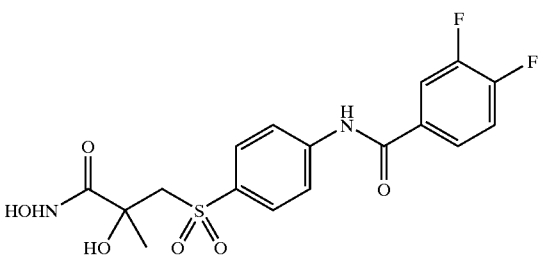

Part A: To a solution of the arilire compound of Example 14, part F (531 mg, 1.94 mmol) in THF (10 mL) was added triethylamine (1.0 mL, 7.2 mmol) followed by 3,4-difluorobenzoyl chloride (0.367 mL, 2.92 mmol) and the solution was heated at reflux for 18 hours. The solution was concentrated in vacua. The residue was dissolved into ethyl acetate, washed with $H_2O$ and dried over $Na_2SO_4$. Chromatography (ethyl acetate/hexane) provided the amide methyl ester as a white solid (360 mg, 45%).

Part B: To a solution of the amide methyl ester of part A (359 mg, 0.87 mmol) in THF (10 mL) and methanol (5 mL) was added 50% hydroxylamine (15 mL) and the solution was stirred for 20 hours. The solution was concentrated in vacuo and the residue was partitioned between ethyl acetate and H$_2$O. Reverse phase chromatography (acetonitrile/H$_2$O) provided 3,4-difluoro-N[4[[2-hydroxy-3-(hydroxyamino)-2-methyl-3-oxopropyl]sulfonyl]phenyl]benzamide as a white solid (165 mg, 46%). HRMS (MH$^+$) calculated for C$_{17}$H$_{16}$N$_2$O$_6$SF$_2$: 415.0775, found: 415.0778.

EXAMPLE 33

N-[4-[[2-hydroxy-3-hydroxyamino)-2-methyl-3-oxopropyl]-sulfonyl]-phenyl]-3-nitrobenzamide

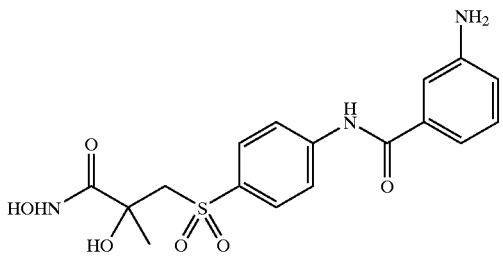

Part A: To a solution of the aniline compound of Example 17, part F (750 mg, 2.75 mmol) in THF (30 mL) was added triethylamine (1.32 mL, 9.6 mmol) followed by 3-nitrobenzoyl chloride (765 mg, 4.12 mmol) and the solution was heated at reflux for 6 hours. The solution was concentrated in vacuo. The residue was dissolved into ethyl acetate, washed with H$_2$O and dried over Na$_2$SO$_4$. Chromatography (ethyl acetate/hexane) provided the amide methyl ester as a white solid (109 mg, 9%).

Part B: To a solution of the amide methyl ester of part A (100 mg, 0.24 mmol) in methanol (20 mL) was added 50% hydroxylamine (20 mL) and the solution was stirred for 20 hours. The solution was concentrated in vacuo and the residue was partitioned between ethyl acetate and H$_2$O. Concentration in vacua provided N-[4-[[2-hydroxy-3-hydroxyamino)-2-methyl-3-oxopropyl)-sulfonyl]phenyl]-3-nitrobenzamide as a white solid (43 mg, 43%). HRMS (MH$^+$) calculated for C$_{17}$H$_{17}$N$_3$O$_8$S: 424.0815, found: 424.0827.

EXAMPLE 34

3-[(4-hydroxybutyl)amino]-N[4-[[2-hydroxy-3-hydroxyamino)-2-methyl-3-oxopropy]phenyl]benzamide

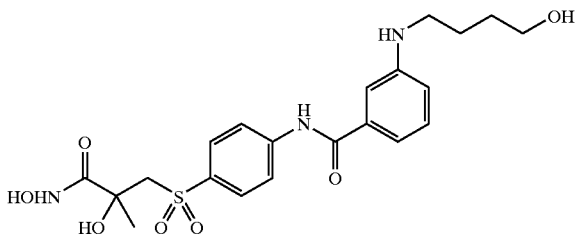

Part A: To a solution of the aniline compound of Example 14, part F (789 mg, 2.9 mmol) in THF (20 mL) was added triethylamine (3.0 mL, 21.6 mmol) followed by 3-nitrobenzoyl chloride (2.0 g, 10.8 mmol) and the solution was heated at reflux for 3.5 hours. The solution was concentrated in vacuo. The residue was dissolved into ethyl acetate, washed with H$_2$O and dried over Na$_2$SO$_4$. Chromatography (ethyl acetate/hexane/methanol) provided the nitro amide methyl ester as a white solid (313 mg, 25%).

Part-B: To a solution of 4% Pd/C (130 mg) in methanol under an atmosphere of N$_2$ was added the nitro amide methyl ester compound of part A (508 mg, 1.2 mmol) in THF (20 mL). The atmosphere was purged S times with H$_2$ at 50 psi. The solution was then filtered through Celite® to remove the catalyst. The filtrate was purified by chromatography (ethyl acetate/methanol) to provide the THF adduct amine methyl ester (240 mg, 43%).

Part C: To a solution of the THF adduct amine methyl ester of part B (230 mg, 0.49 mmol) in methanol (20 mL) was added 50% hydroxylamine (20 mL) and the solution was stirred for 20 hours. The solution was concentrated in vacuo and the residue was partitioned between ethyl acetate and H$_2$O. Concentration in vacuo provided 3-[(4-hydroxybutyl)aminol-N-[4-[[2-hydroxy-3-hydroxyamino)-2-methyl-3-oxopropyl]sulfonyl]phenyl]-benzamide as a white solid (105 mg, 46%). HRMS (MH$^+$) calculated for C$_{21}$H$_{27}$N$_3$O$_7$S: 466.1648, found: 466.1643.

EXAMPLE 35

3-amino-N-[4-[[2-hydroxy-3-(hydroxyamino)-2-methyl-3-oxopropyl]-sulfonyl]phenyl]benzamide

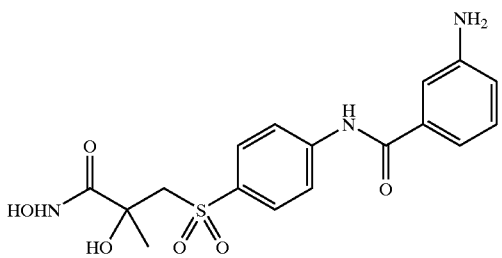

Part A: To a solution of the aniline compound of Example 14, part F (789 mg, 2.9 mmol) in THF (20 mL) was added triethylamine (3.0 mL, 21.6 mmol) followed by 3-nitrobenzoyl chloride (2.0 g, 10.8 mmol) and the solution was heated at reflux for 3.5 hours. The solution was concentrated in vacuo. The residue was dissolved into ethyl acetate, washed with H$_2$O and dried over Na$_2$SO$_4$. Chromatography (ethyl acetate/hexane/methanol) provided the nitro amide methyl ester as a white solid (313 mg, 25%).

Part B: To a solution of 4% Pd/C (200 mg) in methanol under an atmosphere of N$_2$ was added the nitro amide methyl ester compound of part A (600 mg, 1.4 mmol) in methanol (80 mL). The atmosphere was purged 5 times with H$_2$ at 50 psi. The solution was stirred overnight. The solution was then filtered through Celite® to remove the catalyst. The filtrate was purified by chromatography (ethyl acetate/methanol) to provide the aniline methyl ester (543 mg, 99%).

Part C: To a solution of the aniline methyl ester of part B (540 mg, 1.38 mmol) in methanol (5 mL) was added 50% hydroxylamine (5 mL) and the solution was stirred for 24 hours. The solution was concentrated in vacuo. Trituration (ethyl acetate/ethyl ether) provided 3-amino-N-[4-[[2-hydroxy-3-(hydroxyamino)-2-methyl-3-oxopropyl]- sulfonyl]phenyl]benzamide as a white solid (434 mg, 80%). HRMS (MH$^+$) calculated for $C_{17}H_{19}N_3O_6S$: 394.1073, found: 394.1070.

EXAMPLE 36

In Vitro Metalloprotease Inhibition

The compounds prepared in the manner described in Examples 1 to 9 were assayed for activity by an in vitro assay. Following the procedures of Knight et al., *FEBS Lett.* 296(3):263 (1992). Briefly, 4-aminophenylmercuric acetate (APMA) or trypsin activated MMPs were incubated with various concentrations of the inhibitor compound at room temperature for 5 minutes.

More specifically, recombinant human MMP-13 and MMP-1 enzymes were prepared in laboratories of the assignee. MMP-13 was expressed in baculovirus as a proenzyme, and purified first over a heparin agarose column and then over a chelating zinc chloride column. The proenzyme was activated by APMA for use in the assay. MMP-1 expressed in transfected HT-1080 cells was provided by Dr. Howard Welgus of Washington University, St. Louis, Mo. The enzyme was also activated using APMA and was then purified over a hydroxamic acid column.

The enzyme substrate is a methoxycoumarin-containing polypeptide having the following sequence:

MCA-ProLeuGlyLeuDpaAlaArgNH$^2$, wherein MCA is methoxycoumarin and Dpa is 3-(2,4-dinitrophenyl)-L-2,3-diaminopropionyl alanine. This substrate is commercially available from Baychem as product M-1895.

The buffer used for assays contained 100 mM Tris-HCl, 100 mM NaCl, 10 mM $CaCl_2$ and 0.05 percent polyethyleneglycol (23) lauryl ether at a pH value of 7.5. Assays were carried out at room temperature, and dimethyl sulfoxide (DMSO) at a final concentration of 1 percent was used to dissolve compound.

The assayed inhibitor compound in DMSO/buffer solution was compared to an equal amount of DMSO/buffer with no inhibitor as control using Microfluor™ White Plates (Dynatech). The inhibitor or control solution was maintained in the plate for 10 minutes and the substrate was added to provide a final concentration of 4 µM.

In the absence of inhibitor activity, a fluorogenic peptide was cleaved at the gly-leu peptide bond, separating the highly fluorogenic peptide from a 2,4-dinitrophenyl quencher, resulting in an increase of fluorescence intensity (excitation at 328 nm/emission at 415 nm). Inhibition was measured as a reduction in fluorescent intensity as a function of inhibitor concentration, using a Perkin Elmer L550 plate reader. The $IC_{50}$ values were calculated from those values. The results are set forth in the inhibition Table (Table 51) below, reported in terms of $IC_{50}$.

TABLE 51

| | $IC_{50}$ VALUES (in nM) | | | | | |
|---|---|---|---|---|---|---|
| Example | MMP-13 | MMP-1 | MMP-2 | MMP-3 | MMP-8 | MMP-9 |
| 1 | 1.1 | 1100 | 0.5 | 30 | 2.5 | 4.8 |
| 1A (S) | 0.75 | 1005 | 0.39 | | | 1.7 |
| 1B (R) | 21.5 | >10,000 | 11.0 | | | 328 |
| 2 | 1.2 | 470 | 1.0 | 44 | 4.1 | 7 |
| 3 | 3 | 6000 | 1.0 | 166 | 4 | 20 |
| 4 | 0.4 | 9000 | 0.4 | 48.5 | 4.5 | 12.4 |
| 5 | 1.3 | >10,000 | 2.4 | 26.8 | 2.5 | 3.4 |
| 6 | 30 | 8000 | 14.8 | | | |

TABLE 51-continued

| | $IC_{50}$ VALUES (in nM) | | | | | |
|---|---|---|---|---|---|---|
| Example | MMP-13 | MMP-1 | MMP-2 | MMP-3 | MMP-8 | MMP-9 |
| 7 | 2.1 | >10,000 | 2.0 | 51.8 | 4.0 | 13.0 |
| 8 | 200 | >10,000 | | | | |
| 9 | 0.2 | 3000 | 0.4 | | | 16.0 |
| 10 | 1.0 | 4000 | 0.4 | | | 18.0 |
| 11 | 5.0 | 7000 | 7 | | | 66.0 |
| 12 | 3.7 | >10,000 | 2.0 | | | 175 |
| 13 | 5.0 | >10,000 | 2.3 | | | 70.0 |
| 14 | 0.5 | >10,000 | <0.1 | | | |
| 15 | 3200 | >10,000 | 87 | | | |
| 16 | 110 | >10,000 | 0.8 | | | 1160 |
| 17 | 900 | >10,000 | 400 | | | |
| 18 | 13 | >10,000 | 0.5 | | | |
| 19 | 10,000 | >10,000 | 2600 | | | |
| 20 | 6600 | >10,000 | 300 | | | |
| 21 | 3600 | >10,000 | 34 | | | |
| 22 | 280 | >10,000 | 6.7 | | | |
| 23 | 220 | >10,000 | 2.8 | | | 1330 |
| 24 | <0.1 | >10,000 | <0.1 | | | |
| 25 | 1.2 | >10,000 | 0.2 | | | |
| 26 | 1.2 | >10,000 | 0.1 | | | |
| 27 | 666 | >10,000 | 10.0 | | | |
| 28 | 0.8 | >10,000 | <0.1 | | | |
| 29 | 80 | >10,000 | 1.8 | | | |
| 30 | 316 | >10,000 | 20 | | | |
| 31 | 600 | >10,000 | 37.2 | | | |
| 32 | 80 | >10,000 | 1.6 | | | |
| 33 | 1600 | >10,000 | 50 | | | |
| 34 | 1600 | >10,000 | 32.7 | | | |
| 35 | 290 | >10,000 | 6.7 | | | |

EXAMPLE 37

In Vivo Angiogenesis Assay

The study of angiogenesis depends on a reliable and reproducible model for the stimulation and inhibition of a neovascular response. The corneal micropocket assay provides such a model of angiogenesis in the cornea of a mouse. See, A Model of Angiogenesis in the Mouse Cornea; Kenyon,BM, et al., Investigative Ophthalmology & Visual Science, July 1996, Vol. 37, No. 8.

In this assay, uniformly sized Hydron™ pellets containing bFGF and sucralfate were prepared and surgically implanted into the stroma mouse cornea adjacent to the temporal limbus. The pellets were formed by making a suspension of 20 µL sterile saline containing 10 µg recombinant bFGF, 10 mg of sucralfate and 10 µL of 12 percent Hydron™ in ethanol. The slurry was then deposited on a 10×10 mm piece of sterile nylon mesh. After drying, the nylon fibers of the mesh were separated to release the pellets.

The corneal pocket was made by anesthetizing a 7 week old C57Bl/6 female mouse, then proptosing the eye with a jeweler's forceps. Using a dissecting microscope, a central, intrastromal linear keratotomy of approximately 0.6 mm in length was performed with a #15 surgical blade, parallel to the insertion of the lateral rectus muscle. Using a modified cataract knife, a lamellar micropocket was dissected toward the temporal limbus. The pocket was extended to within 1.0 mm of the temporal limbus. A single pellet was placed on the corneal surface at the base of the pocket with a jeweler's forceps. The pellet was then advanced to the temporal end of the pocket. Antibiotic ointment was then applied to the eye.

Mice were dosed on a daily basis for the duration of the assay. Dosing of the animals was based on bioavailability and overall potency of the compound. An exemplary dose is 50 mg/kg bid, po. Neovascularization of the corneal stroma begins at about day three and was permitted to continue under the influence of the assayed compound until day five. At day five, the degree of angiogenic inhibition was scored by viewing the neovascular progression with a slit lamp microscope.

The mice were anesthetized and the studied eye was once again proptosed. The maximum vessel length of neovascularization, extending from the limbal vascular plexus toward the pellet was measured. In addition, the contiguous circumferential zone of neovascularization was measured as clock hours, where 30 degrees of arc equals one clock hour. The area of angiogenesis was calculated as follows.

$$\text{area} = \frac{(0.4 \times \text{clock hours} \times 3.14 \times \text{vessel length (in mm)})}{2}$$

The studied mice were thereafter compared to control mice and the difference in the area of neovascularization was recorded. A contemplated compound typically exhibits about 25 to about 75 percent inhibition, whereas the vehicle control exhibits zero percent inhibition. The results of this assay for several inhibitor compounds are shown in Table 52, below.

TABLE 52

| Example | Percentage of Control |
|---|---|
| 1 | 51.9 |
| 1A (S) | 62.7 |
| 1B (R) | 49.3 |
| 2 | 53.4 |
| 3 | 77.4 |
| 4 | 65.2 |
| 5 | 57.8 |
| 9 | 61.1 |
| 16 | 41.6 |

From the foregoing, it will be observed that numerous modifications and variations can be carried out without departing from the true spirit and scope of the novel concepts of the present invention. It is to be understood that no limitation with respect to the specific example presented is intended or should be inferred. The disclosure is intended to cover by the appended claims all such modifications as fall within the scope of the claims.

What is claimed is:
1. A compound or a salt thereof, wherein:
the compound corresponds in structure to Formula I;

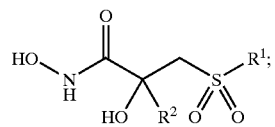

I $R^1$ is a substituted phenyl radical that:
has a length greater than about that of a hexyl group and less than about that of an eicosyl group, and
$R^2$ is selected from the group consisting of hydrogen, hydroxy, $C_1$–$C_4$-hydrocarbyl, hydroxy-$C_1$–$C_4$-hydrocarbyl, $C_1$–$C_4$-hydrocarbyloxy, halo-$C_1$–$C_4$-hydrocarbyl, $C_1$–$C_4$-hydrocarbyloxymethyl, aminomethyl, (N-$C_1$–$C_3$-hydrocarbyl)aminomethyl, (N,N-di-$C_1$–$C_3$-hydrocarbyl)aminomethyl, (N-morpholino)methyl, (N-pyrrolidino)methyl, and (N-thiomorpholino)methyl.

2. A compound or salt thereof according to claim 1, wherein $R^2$ is selected from the group consisting of hydrogen, hydroxy, hydroxymethyl, methoxymethyl, and (N-morpholmo)methyl.

3. A compound or salt thereof according to claim 1, wherein $R^2$ is selected from the group consisting of hydrogen, $C_1$–$C_4$ hydrocarbyl, hydroxy-$C_1$–$C_4$ hydrocarbyl, $C_1$–$C_4$ hydrocarbyloxy, halo-$C_1$–$C_4$ hydrocarbyl, $C_1$–$C_4$ hydrocarbyloxymethyl, aminomethyl, (N-$C_1$–$C_3$ hydrocarbyl)aminomethyl, (N,N-di-$C_1$–$C_3$ hydrocaxbyl) aminomethyl, (N-morpholino)methyl, (N-pyrrolidino) methyl, and (N-thiomorpholino)methyl.

4. A compound or salt thereof according to claim 3, wherein the compound corresponds structure to the following formula:

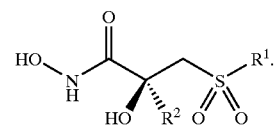

III

5. A pharmaceutical composition, wherein:
the pharmaceutical composition comprises a compound or a pharmaceutically acceptable salt thereof;
the compound corresponds in structure to Formula I:

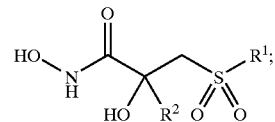

I $R^1$ is a substituted phenyl radical that:
has a length greater than about that of a hexyl group and less than about that of an eicosyl group, and
$R^2$ is selected from the group consisting of hydrogen, hydroxy, $C_1$–$C_4$-hydrocarbyl, hydroxy-$C_1$–$C_4$-hydrocarbyl, $C_1$–$C_4$-hydrocarbyloxy, halo-$C_1$–$C_4$-hydrocarbyl, $C_1$–$C_4$-hydrocarbyloxymethyl, aminomethyl, (N-$C_1$–$C_3$-hydrocarbyl)aminomethyl, (N,N-di-$C_1$–$C_3$-hydrocarbyl)aminomethyl, (N-morpholino)methyl, (N-pyrrolidino)methyl, and (N-thiomorpholino)methyl.

6. A pharmaceutical composition according to claim 5, wherein $R^2$ is selected from the group consisting of hydrogen, $C_1$–$C_4$ hydrocarbyl, hydroxy-$C_1$–$C_4$ hydrocarbyl, $C_1$–$C_4$ hydrocarbyloxy, halo-$C_1$–$C_4$ hydrocarbyl, $C_1$–$C_4$ hydrocarbyloxymethyl, arninomethyl, (N-$C_1$–$C_3$ hydrocarbyl)anunomethyl, (N,N-di-$C_1$–$C_3$ hydrocarbyl) aminomethyl, (N-morpbolino)methyl, (N-pyrrolidino) methyl, and (N-thiomorpholino)methyl.

7. A method for treating a host animal having a condition associated with pathological matrix metalloprotease activity, wherein:
the method comprises administering a compound or a pharmaceutically acceptable salt thereof in an MMP enzyme-inhibiting effective amount to a mammalian host having such a condition;

the compound corresponds in structure to Formula I:

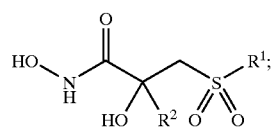

R$^1$ is a substituted phenyl radical that:
has a length greater than about that of a hexyl group and less than about that of an eicosyl group, and R$^2$ is selected from the group consisting of hydrogen, hydroxy, C$_1$–C$_4$ hydrocarbyl, hydroxy-C$_1$–C$_4$-hydrocarbyl, C$_1$–C$_4$-hydrocarbyloxy, halo-C$_1$–C$_4$-hydrocarbyl, C$_1$–C$_4$-hydrocarbyloxymethyl, aminomethyl, (N-C$_1$–C$_3$-hydrocarbyl)aminomethyl, (N,N-di-C$_1$–C$_3$-hydrocarbyl)aminomethyl, (N-morpholino)methyl, (N-pyrrolidino)methyl, and (N-thiomorpholino)methyl.

8. The method according to claim 7 wherein said R$^1$ radical is PhR$^3$ in which Ph is phenyl substituted with R$^3$ at the 4-position, and said R$^3$ substituent is benzamido, nicotinainido, isonicotinamido, picolinamido or ureidophenyl in which said R$^3$ substituent is optionally substituted at its own meta- or para-position or both with a moiety selected from the group consisting of a halogen, a nitro, a C$_1$–C$_8$ hydrocarbyl, a C$^1$–C$^7$ hydrocarbyloxy, an amino and an amino-C$_2$–C$_4$-hydroxyalkyl group.

9. The method according to claim 7 wherein said R$^1$ radical has a length greater than that of an octyl group and less than that of a stearyl group.

10. The method according to claim 7 wherein said compound corresponds to Formula II:

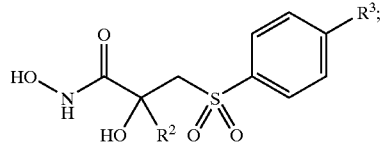

wherein R$^2$ is hydrogen, C$^1$–C$^4$ hydrocarbyl, hydroxy-C$_1$–C$_4$hydrocarbyl, C$^1$–C$^4$ hydrocarbyloxy, halo-C$^1$–C$^4$ hydrocarbyl, C$^1$–C$^4$ hydrocarbyloxymethyl, aminomethyl, (N-C$_1$–C$_3$ hydrocarbyl)aminomethyl, (N,N-di-C$_1$–C$_3$ hydrocarbyl)aminomethyl, (N-morpholino)methyl, (N-pyrrolidino)methyl, or (N-thiomorpholino)methyl; and R$_3$ is a phenyl, phenoxy, anilino, thiophenoxy, phenylazo, benzamido, nicotinamido, isonicotinanudo, picolinamido or ureidophenyl group.

11. The method according to claim 7 wherein said R$^3$ is a phenyl, phenoxy, anilino or thiophenoxy group that is itself optionally substituted at meta or para position or both with a moiety that is selected from the group consisting of a halogen, a C$_1$–C$_9$ hydrocarbyloxy group, a C$_1$–C$_{10}$ hydrocarbyl group, a di-C$_1$–C$_9$ hydrocarbylamino group, a carboxyl C$_1$–C$_8$ hydrocarbyl group, a C$_1$–C$_4$ hydrocarbyloxy carbonyl C$_1$–C$_4$ hydrocarbyl group, a C$_1$–C$_4$ hydrocarbyloxycarbonyl C$_1$–C$_4$ hydrocarbyl group, and a carboxamido C$_1$–C$_8$ ghydrocarbyl group, or is substituted at the meta- and para-positions by two methyl groups or by a C$_1$–C$_2$ alkylenedioxy group.

12. The method according to claim 7 wherein said R$^3$ is a phenoxy or thiophenoxy group that is unsubstituted.

13. The method according to claim 7 wherein said R$^3$ substituent is a benzamido, nicotinamnido, isonicotinarnido, picolinamido or ureidophenyl group in which said R$^3$ substituent is optionally substituted at its own meta- or para-position with a moiety selected from the group consisting of a halogen, a nitro, a C$_1$–C$_8$ hydrocarbyl, a C$_1$–C$_7$ hydrocarbyloxy, an amino and an amino-C$_2$–C$_4$-hydroxyalkyl group.

14. A method according 7, wherein R$^2$ is selected from the group consisting of hydrogen, C$_1$–C$_4$ hydrocarbyl, hydroxy-C$_1$–C$_4$ hydrocarbyl, C$_1$–C$_4$ hydrocarbyloxy, halo-C$_1$–C$_4$ hydrocarbyl, C$_1$–C$_4$ hydrocarbyloxymethyl, aminomethyl, (N-C$_1$–C$_3$ hydrocarbyl)aminomethyl, (N,N-di-C$_1$–C$_3$ hydrocarbyl)aminomethyl, (N-morpholino)methyl, (N-pyrrolidino)methyl, and (N-thiomorpholino)methyl.

15. A method according to claim 7, wherein R$^2$ is selected from the group consisting of hydrogen, hydroxy, hydroxymethyl, methoxymethyl, and (N-morpholino)methyl.

16. The method according to claim 7 wherein said R$^2$ substituent is methyl, hydroxymethyl, methoxymethyl or (N-morpholino)methyl group.

17. The method according to claim 7 wherein said compound is an enantiomer whose stereoconfiguration is as shown in Formulas III or IV

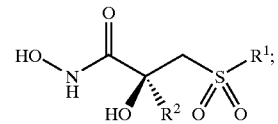

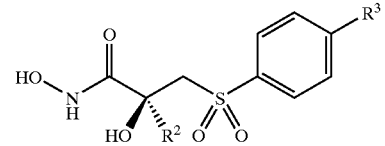

18. A method according to claim 14, wherein the compound corresponds in structure to the following formula:

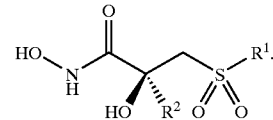

19. The method according to claim 7 wherein said compound is administered a plurality of times.

* * * * *